US005583000A

United States Patent [19]
Ortiz de Montellano et al.

[11] Patent Number: 5,583,000
[45] Date of Patent: Dec. 10, 1996

[54] PROTEASE-BINDING COMPOUNDS AND METHODS OF USE

[75] Inventors: Paul R. Ortiz de Montellano, San Francisco; Irwin D. Kuntz, Greenbrae; Charles S. Craik, San Francisco, all of Calif.; Paul S. Furth, Waltham; Juan C. Alvarez, Chelmsford, both of Mass.; Patricia S. Caldera, San Francisco, Calif.; Dianne L. DeCamp, Durham, N.C.; Lilia M. Babé; James De Voss, both of San Francisco, Calif.; Rafael Salto, Granada, Spain; Zhihua Sui, Piscataway, N.J.

[73] Assignee: The Regents of the University of California, Oakland, Calif.

[21] Appl. No.: 122,792

[22] Filed: Sep. 16, 1993

Related U.S. Application Data

[63] Continuation-in-part of Ser. No. 753,878, Sep. 3, 1991, abandoned.
[51] Int. Cl.$^6$ .................... G01N 33/573; A61K 31/445; A61K 31/44; A61K 31/47
[52] U.S. Cl. .................. 435/7.4; 435/5; 435/7.71; 435/7.72; 435/238; 435/184; 435/240.2; 514/314; 514/317; 514/440; 514/431; 514/289; 514/358; 546/168; 546/192; 546/207; 546/229
[58] Field of Search .................. 435/5, 184, 244, 435/240.2, 7.4, 7.71, 18, 7.72, 238; 546/207, 229, 192, 168, 237, 240, 340, 347, 75; 514/317, 314, 440, 431, 289, 358; 549/30, 35, 369, 20, 11

[56] References Cited

U.S. PATENT DOCUMENTS

| | | | |
|---|---|---|---|
| 4,880,779 | 11/1989 | Gallaher | 514/15 |
| 4,916,122 | 4/1990 | Chu et al. | 514/50 |
| 5,095,021 | 3/1992 | Zipplies et al. | 514/327 |

OTHER PUBLICATIONS

Furth et al (1991) "Inhibition of HIV Protease with Non-Peptide Derivatives of Haloperidol", Fourth Chemical Congress of north America, NY, NY, USA, Aug. 25–30, 1991, Abstr.
De Camp et al, "Structure–Based Inhibition of HIV-1 Protease Activity And Viral Infectivity", in *Structure and Function of the Aspartic Proteinases*, Dunn, ed., published 1991 by Plenum Press, pp. 489–492.
L. Ratner, et al. "Complete nucleotide sequence of the AIDS virus, HTLV–III," Nature 323:277–284 (1985).
T. J. McQuade, et al. "A Synthetic HIV–1 Protease Inhibitor with Antiviral Activity Arrests HIV–Like Particle Maturation," Science 247:454–457 (1990).
H. P. Schnebli and N. J. Braun, "Proteinase inhibitors as drugs," (1986) Elsevier Science Publishers BV.
J. J. Blumenstein, et al. "Synthetic Non–Peptide Inhibitors of HIV Protease," Biochem. and Biophys. Res. Comm. 163:980–987 (1989).

K. Moelling, et al. "In vitro inhibition of HIV–1 proteinase by cerulenin," FEBS Letters 261:373–377 (1990).
N. A. Roberts, et al. "Rational Design of Peptide–Based HIV Proteinase Inhibitors," Science 248:358–361 (1990).
R. Pal, et al. "Processing of the structural proteins of human immunodeficiency virus type 1 in the presence of monensin and cerulein," Proc. Natl. Acad. Sci. 85:9283–9286 (1988).
W. G. Farmerie, et al. "Expression and Processing of the AIDS Virus Reverse Transcriptase in *Escherichia coli*," Science 236:305–308 (1987).
C. Debouck, et al. "Human immunodeficiency virus protease expressed in *Escherichia coli* exhibits autoprocessing and specific maturation of the gag precursor," Proc. Natl. Acad. Sci. 84:8903–8906 (1987).
N. E. Kohl, et al. "Active human immunodeficiency virus protease is required for viral infectivity," Proc. Natl. Acad. Sci. 85:4686–4690 (1988).
M. A. Navia, et al. "Three-dimensional structure of aspartyl protease from human immunodeficiency virus HIV–1," Nature 337:615–620 (1989).
R. Lapatto, et al. "X–ray analysis of HIV–1 proteinase at 2.7 Å resolution confirms structural homology among retroviral enzymes," Nature 342:299–302 (1989).
A. Wlodawer, et al. "Conserved Folding in Retroviral Proteases: Crystal Structure of a Synthetic HIV–1 Protease," Science 245:616–621 (1989).
S. Seelmeier, et al. "Human immunodeficiency virus has an aspartic–type protease that can be inhibited by pepstatin A," Proc. Natl. Acad. Sci. 85:6612–6616 (1988).
P. L. Darke, et al. "Human Immunodeficiency Virus Protease," J. Bio. Chem. 264:2307–2312 (1989).
T. D. Meek, et al. "Human immunodeficiency virus 1 protease expressed in *Escherichia coli* behaves as a dimeric aspartic protease," Proc. Natl. Acad. Sci. 86:1841–1845 (1989).
L. H. Pearl and W. R. Taylor, "A structural model for the retroviral proteases," Nature 329:351–354 (1987).
A. G. Tomasselli, et al. "Substrate Analogue Inhibition and Active Site Titration of Purified Recombinant HIV–1 Protease," Biochemistry 29:264–269 (1990).
T. D. Meek, et al. "Inhibition of HIV–1 protease in infected T–lymphocytes by synthetic peptide analogues," Nature 343:90–92 (1990).
S. Pichuantes, et al. "Recombinant HIV2 Protease Processes HIV1 Pr53$^{gag}$ and Analogous Junction Peptides in Vitro," J. Bio. Chem. 265:13890–13898 (1990).

(List continued on next page.)

*Primary Examiner*—Kay K. A. Kim
*Attorney, Agent, or Firm*—Townsend and Townsend and Crew LLP

[57] ABSTRACT

Non-peptide, protease-binding compounds are described as useful in the detection, labelling, and inhibition of retroviral proteases. Aryl piperidinyl derivatives and other compounds related in structure have been found to be HIV-1 and HIV-2 protease-binding compounds.

106 Claims, 15 Drawing Sheets

OTHER PUBLICATIONS

R. L. DesJarlais, et al. "Structure–based design of nonpeptide inhibitors specific for the human immunodeficiency virus 1 protease," Proc. Natl. Acad. Sci 87:6644–6648 (1990).

M. L. Moore, et al. "Peptide Substrates and Inhibitors of the HIV–1 Protease," Biochem. and Biophys. Res. Comm. 159:420–425 (1989).

T. Maniatis, et al. "Molecular Cloning, A Laboratory Manual," (Cold Spring Harbor Press NY (1982).

L. Babe' et al., "HIV1 Protease: Bacterial Expression, Purification and Characterization," Protein and Pharm. Eng. pp. 71–88 (1990).

G. B. Dreyer, et al., "Inhibition of human immunodeficiency virus 1 protease in vitro: Rational design of substrate analogue inhibitors," Proc. Natl. Acad. Sci. USA vol. 86 pp. 9752–9756 (Dec. 1989).

H. Toh, et al., "Close structural resemblance between putative polymerase of a *Drosophila* transposable genetic element 17.6 and pol gene product of Moloney murine leukaemia virus" EMBO J. vol. 4 5:1267–1272 (1985).

M. D. Power, et al., "Nucleotide Sequence of SRV–1, a Type D Simian Acquired Immune Deficiency Syndrome Retrovirus," Science 231:1567–1572 (Mar. 1986).

AIDS Research and Reference Reagent Program Catalog (Jan. 1991 Catalog) NIH Pub. No. 91–1536.

Fig. IIa
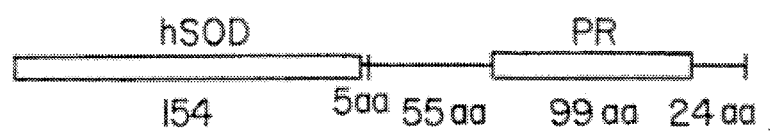
Fig. IIb
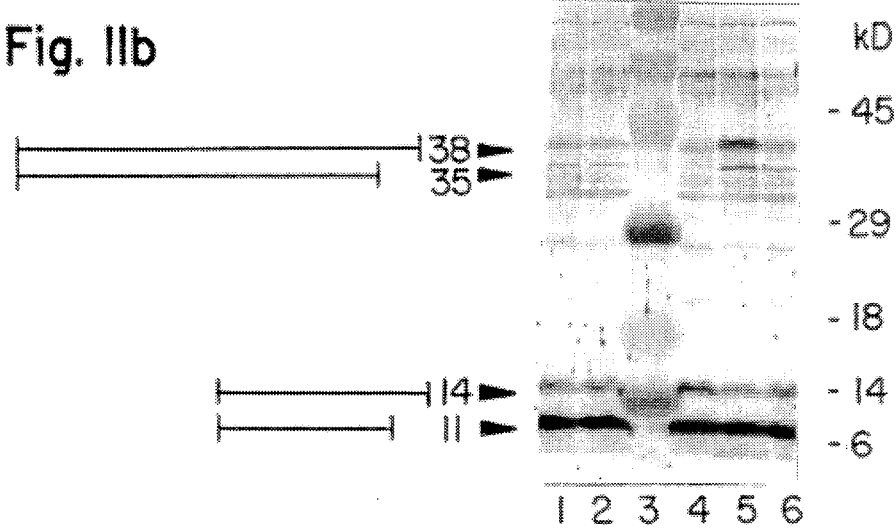
Fig. IIc
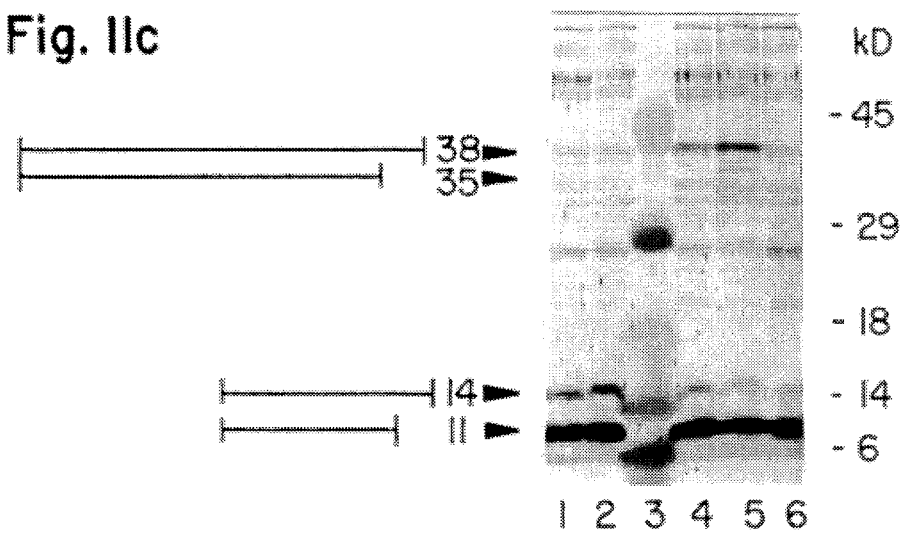

PROTEASE-BINDING COMPOUNDS AND METHODS OF USE

GOVERNMENT RIGHTS

This invention was made with Government support under Gram Nos. NIGMS-39552, GM-31497, GM-07175, GM-29072 and GM-13369, awarded by the National Institutes of Health, and DARPA Contract No. N00014-86-K0757, awarded by the Office of Naval Research. The Government has certain rights in this invention.

CROSS REFERENCE TO RELATED APPLICATION

This application is a continuation-in-part of co-pending application Ser. No. 07/753,878, filed Sep. 3, 1991, now abandoned.

FIELD OF THE INVENTION

The present invention resides in the field of substances which bind to proteases, and the use of these substances in various analytical, diagnostic and therapeutic methods based on this binding capability.

BACKGROUND OF THE INVENTION

An ever-increasing number of viruses are being identified as the source of human disease. The better known diseases caused by viruses include chicken pox, measles, mumps, influenza, hepatitis, poliomyelitis, rabies, and now, of course, acquired immunodeficiency syndrome (AIDS). Them are, however, many more virus-related diseases. Indeed, viral infections are estimated to be responsible for more than sixty percent of human sickness occurring in developing countries.

In contrast to the success achieved by the use of antibiotics in the treatment of bacterial infections, efforts to treat viral infections have been largely ineffective. When individuals become infected, modem medicine can do little but ease the symptoms. Viral epidemics have only been avoided by treatment of uninfected individuals with vaccines.

The effort to treat viral infection has been hampered largely by the unique structural and functional characteristics of viruses. A retrovirus is essentially nucleic acid surrounded by a lipid-protein envelope. A virus invades a host cell and uses the host cell's machinery to replicate itself. The latter characteristic makes it especially difficult to find drugs which kill the virus and leave the host unharmed.

With a more detailed understanding of viral function, more sophisticated and promising approaches to treatment have been suggested. One approach has come from the recognition that the viral envelope proteins may be involved in binding to the host cell and, ultimately, penetration of the virus into the host cell. This approach involves the use of competing proteins or parts of proteins to block the binding or "fusion" event. An example of this approach can be found in U.S. Pat. No. 4,880,779 which describes inhibitory peptides to block retroviral fusion. Another approach has come from the recognition that some viruses use unique polymerases to replicate nucleic acid. This approach involves the use of competing, nucleotide derivatives to bind to the polymerase and stop replication. An example of this approach can be found in U.S. Pat. No. 4,916,122 which describes the use of synthetic deoxyuridine derivatives to block retroviral nucleic acid replication.

Another approach has emerged from a more in-depth understanding of the viral organization. For example, a complete sequencing of the AIDS virus genome indicates that the human immunodeficiency virus (HIV) genome exhibits the same overall gag-pol-env organization as other retroviruses. See L. Ratner, et al., Nature 313:277 (1985). The viral genes are initially translated into large precursor molecules that are subsequently processed into smaller, functional proteins by an enzyme known as HIV protease. See W. G. Farmerie, et al., Science 236:305 (1987). Since the processing by the protease is essential to the virus, it was suggested that inhibition of the protease could block virus maturation. See C. Debouck, et al., Proc. Nat. Acad. Sci. 84:8903 (1987), and N. E. Kohl, et al., Proc. Nat. Acad. Sci. 85:4686 (1988).

The type of compound that might inhibit retroviral proteases was suggested by the finding that a conserved sequence, Asp-Thr-Gly, of retroviral proteases is conserved in the active sites of aspartic proteases. See H. Toh, et al., Nature 315:691 (1985), and M. D. Power, et al., Science 231:1567 (1986). Indeed, detailed modelling as well as X-ray analysis indicates that retroviral enzymes could be examples of ancestral dimeric aspartic proteases. See L. H. Pear and W. R. Taylor, Nature 329:351 (1987); M. A. Navia, et al., Nature 337:615 (1989); R. Lapatto, et al., Nature 342:299 (1989); and A. Wlodawer, et al., Science 245:616 (1989).

Pepstatin A is a classic inhibitor of aspartic proteases. When tested for inhibition of HIV protease, pepstatin A was found to partially inhibit protein processing. See S. Seelmeier, et al., Proc. Nat. Acad. Sci. 85:6612 (1988); and P. Darke, et at., J. Biol. Chem. 264:2307 (1989). On the other hand, typical serine protease inhibitors have been shown not to inhibit HIV protease. See T. D. Meek, et al., Proc. Nat. Acad. Sci. 86:1841 (1989). This was strong evidence that the HIV protease was an aspartic protease.

Given the nature of the HIV protease, the most immediate approach to inhibiting the enzyme was to identify and design peptide substrates and peptide analogues that would act as inhibitors of the enzyme. A number of such substrates have been described. See M. L. Moore, et al., Biochem. Biophys. Res. Comm. 159:420 (1989); G. B. Dreyer, et al., Proc. Nat. Acad. Sci. 86:9752 (1989); T. D. Meek, et al., Nature 343:90 (1990); and A. G, Tomasselli, et al., Biochemistry 29:264 (1990).

Non-hydrolyzable peptide analogue substrates have also been described. N. A. Roberts, et al., Science 248:358 (1990) examine a family of related peptide inhibitors having non-hydrolyzable inserts. Similarly, T. J. McQuade, et al., Science 247:454, report on a variety of peptide inhibitors containing a hydroxyethylene isostere as a nonhydrolyzable, synthetic replacement for amino acids.

Peptide inhibitors are less than fully satisfactory as pharmacologic agents. As reported by H. P. Schnebli and N. J. Braun, Proteinase Inhibitors (Elsevier Science Publishers, 1986), many such inhibitors are readily degraded in vivo, and some do not penetrate cell membranes. For these reasons, most known peptide inhibitors require unreasonably high concentrations.

A handful of non-peptide inhibitors of HIV protease have been studied. Cerulenin, an antifungal antibiotic, is an example of a non-peptide inhibitor of HIV protease. See R. Pal, et al., Proc. Nat. Acad. Sci. 85:9283 (1988); J. J. Blumenstein, et al., Biochem. Biophys. Res. Comm. 163:980 (1989); and K. Moelling, et al., FEBS Letters 261:373 (1990). Unfortunately, cerulenin exhibits pronounced cytotoxicity.

SUMMARY OF THE INVENTION

The present invention relates to non-peptide protease-binding compounds and to various uses of these compounds, both therapeutic and diagnostic, based on their protease-binding properties. These methods include use of the compounds for detecting and quantitating the presence of retroviral proteases in a biological sample for analytical or diagnostic purposes, and use of the compounds for inhibiting the ability of proteases, and particularly vital proteases, to process proteins in living cells.

In accordance with the present invention, aryl piperidinyl derivatives and other compounds with related or similar structures have been found to be useful protease-binding compounds. Furthermore, many of these compounds, particularly those containing epoxy moieties, ynones (i.e., acetylenic ketones) and α,β-unsaturated ketones (i.e., olefinic ketones or enones), have been found to be bind covalently to HIV protease, thereby achieving an irreversible effect. Many of these compounds have also been found to be potent, non-peptide inhibitors of HIV aspartic proteases. Compounds within the scope of the present invention fall within several formulas, both specific and generic. These are as follows.

FORMULA I:

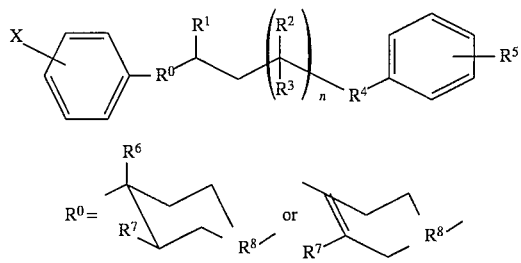

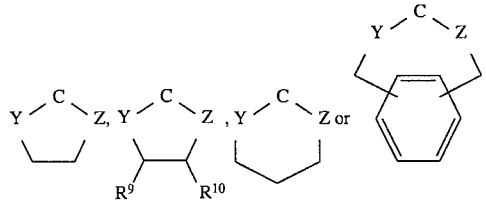

($R^6$ is H, OH, $CH_2OH$ or $OC(O)CH_3$; $R^7$ is H or OH; and $R^8$ is N, $N^+$—$O^-$, $N^+(Hal^-)$—$CH_3$, $N^+(Hal^-)$—$CH_2CH_2Ph$ or C—OH)

$R^1$=H or Ph $R^2$=H, $CH_3$, CH=$CH_2$, $CH_2$—CH=$CH_2$, or $CH_2$—C≡CH $R^3$=H, $CH_3$, CH=$CH_2$, $CH_2$—CH=$CH_2$, or $CH_2$—C≡CH $R^4$=$CH_2$, C=$CH_2$, CHOH, C=O, C=N—OH, C=N—$NH_2$, C=N—NH—$C_2H_5OH$, C(OH)—Ph, C(OH)—Bz, C(OH)—$CH_2SCH_3$, C(OH)—CH=$CH_2$,

(Y and Z are each O or S and may be the same or different; $R^9$ and $R^{10}$ are each H or $C_1$-$C_3$ alkyl and may be the same or different)

$R^5$=H, halogen, phenyl, or pyridyl

X=H or halogen n=zero or 1

(Hal=halogen, Ph=phenyl, and Bz=benzyl)

FORMULA II:

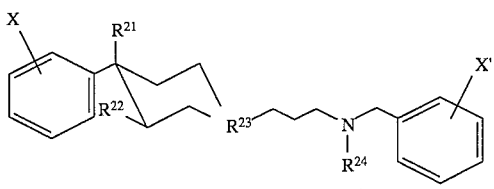

$R^{21}$=H, OH, $CH_2OH$ or $OC(O)CH_3$ $R^{22}$=H or OH $R^{23}$=N, $N^+$—$O^-$, $N^+(Hal^-)$—$CH_3$, $N^+(Hal^-)$—$CH_2CH_2Ph$ or C—OH $R^{24}$=H, $C_1$-$C_3$ alkyl, $C_2$-$C_4$ alkoxyalkyl, phenyl-($C_1$-$C_3$ alkyl), or phenyl -($C_1$-$C_3$ alkyl)-carbonyl X=H or halogen X'=H or phenyl

FORMULA III:

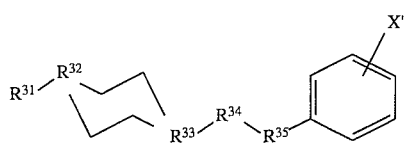

$R^{31}$=phenyl, benzyl, halophenyl or halobenzyl $R^{32}$=N or CHOH $R^{33}$=CHOH when $R^{32}$ is N, and $R^{33}$=N or $N^+$—$O^-$ when $R^{32}$ is CHOH $R^{34}$=$C_1$-$C_3$ alkyl, CH=CH, $CH_2$—CH=CH, CH≡CH, $CH_2$—CH≡CH or C(=CH)—S—($C_1$-$C_3$ alkyl)—OH $R^{35}$=$CH_2$CHOH, C=O or

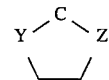

($R^{36}$ is O or S)

X'=H, phenyl or halogen

FORMULA IV:

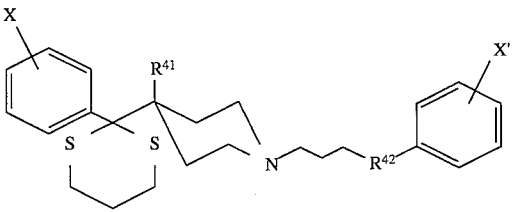

$R^{41}$=H or OH $R^{42}$=C=O or

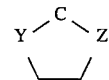

(Y and Z are O or S)

X and X' are each H or halogen and may be the same or different

FORMULA V:

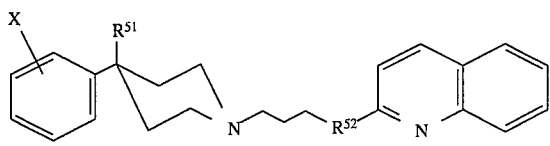

$R^{51}$=H or OH $R^{52}$=C=O or C(OH)—Ph (Ph is phenyl)

X=H or halogen

FORMULA VI:

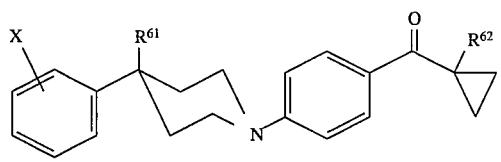

$R^{61}$=H or OH $R^{62}$=H, $C_1$-$C_6$ alkyl, $C_3$-$C_6$ alkenyl, $C_3$-$C_6$ alkynyl, hydroxy-($C_1$-$C_6$ alkyl), hydroxy-($C_3$-$C_6$ alkenyl) or hydroxy-($C_3C_6$ alkynyl)

X=H or halogen

Additional compounds within the scope of this invention are:

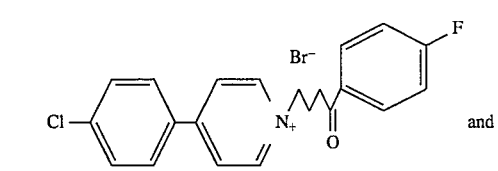

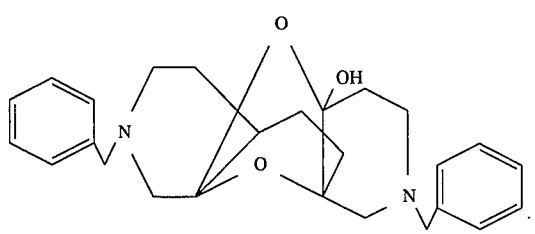

Within the scope of Formulas I through VI, certain embodiments are preferred. In Formula I, one preferred subclass is that in which $R^0$=

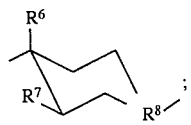

$R^1$=$R^2$=$R^3$=H; and n=1. Within this subclass, further preferred structures are those in which $R^6$=OH; $R^7$=H; $R^8$=N; and $R^4$ = C(OH)—Ph, C(OH)—Bz,

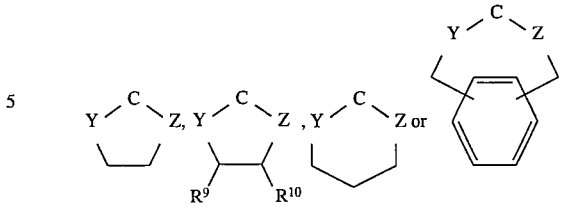

Also preferred are those in which X is p-chloro, and those in which $R^5$ is p-fluoro. An additional subgroup of interest are those in which

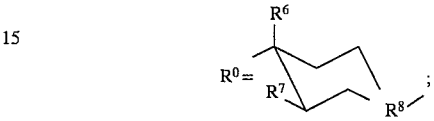

$R^2$ is $CH_2$—C≡CH; $R^3$ is H or $CH_2$—C≡CH; and n is 1.

In Formula II, a preferred subclass is one in which $R^{21}$=OH, $R^{22}$=H, and $R^{23}$=N, with a more preferred group within this subclass defined by the additional limitation of X=p-chloro. Further preferred groups are those defined by the additional limitation that $R^{24}$=$C_2$-$C_4$ alkoxyalkyl, phenyl-($C_1$-$C_3$ alkyl) or phenyl-($C_1$-$C_3$ alkyl)-carbonyl, with phenyl-($C_1$-$C_3$ alkyl) and phenyl-($C_1 14 C_3$ alkyl)-carbonyl even more preferred.

In Formula III, one preferred subclass is that defined by $R^{31}$=benzyl; $R^{32}$=N; $R^{33}$=CHOH; $R^{34}$=$CH_2CH_2$, CH=CH or CH≡CH; $R^{35}$=$CH_2$CHOH or

where $R^{36}$=O; and X'=H. Another preferred subclass is that defined by $R^{31}$=phenyl or halophenyl; $R^{32}$=CHOH; $R^{33}$=N or $N^+$—O; $R^{34}$=$CH_2$—CH=CH, $CH_2$—CH≡CH or C(=CH)—S—($C_1$-$C_3$ alkyl)—OH; and $R^{35}$=C=O or

in which $R^{36}$=O.

In Formula IV, a preferred subclass is that defined by $R^{41}$=OH; X=p-chloro; and X'=p-fluoro, and a further preferred subclass is that defined by Y and Z both being S.

In Formula V, a preferred subclass is that defined by $R^{51}$=OH and X=H.

In Formula VI, a preferred subclass is that deemed by $R^{61}$=OH and X=p-chloro. A further preferred subclass is that deemed by $R^{62}$=H, $CH_2CH_2CH_2$CH=$CH_2$ or $CH_2$C≡CC$H_2$OH.

By virtue of their ability to bind to proteases, these compounds are useful in a variety of ways.

For those compounds in which the binding involves the formation of a covalent bond, the result is a complex which serves as a labelled form of the protease. The label may be the increase in molecular weight which results from the covalent attachment of the protease-binding compound. Alternatively, the label may be a signal-generating moiety attached to or integrated into the structure of the protease-binding compound. Examples of such moieties are enzymes, fluorophores, chemophores, high-affinity groups and radioactive (isotopically labeled) atoms. A single complex may contain a single label or multiple labels of either the same or different types. Labelling in accordance with this invention may be performed on proteases regardless of their environment, in vivo or in vitro. Labelling may thus extend to proteases present in tissues and cells, and in particular, in lymphocytes. The labelling will generally be followed by an appropriate detection technique, such as autoradiography or any of the wide variety of techniques known to those skilled in the art.

As one application of labelling in accordance with this invention, the protease-binding compounds of this invention can be used as mechanistic probes of retrovital proteases in topologic assays of compounds for which the presence and nature of a protease binding site is to be determined. A topologic assay, for example, will be performed by combining the following materials in a reaction vessel:

(a) a labelled version of one or more of the compounds of the above formulas whose protease binding site is known, (b) one or more retrovital proteases, and (c) a test compound whose protease binding site is to be determined. The amount of binding of the first protease-binding compound to the proteases is then determined and compared with the amount of such binding which occurs in the absence of the test compound.

In addition to labelling applications, the protease-binding compounds may be administered for purposes of inhibiting protein processing by retrovital proteases, thereby preventing the proteases from hydrolyzing a peptide substrate.

Other features, applications, advantages and embodiments of the invention will be evident from the descriptions which follow.

BRIEF DESCRIPTION OF THE DRAWINGS

FIG. 11a schematically shows the autoprocessing of HIV-1 protease. FIGS. 11b and 11c are gel photographs showing the electrophoresis of the results of HIV-1 processing in the presence of various inhibitors.

DETACHED DESCRIPTION OF THE INVENTION AND PREFERRED EMBODIMENTS

Figure 1:
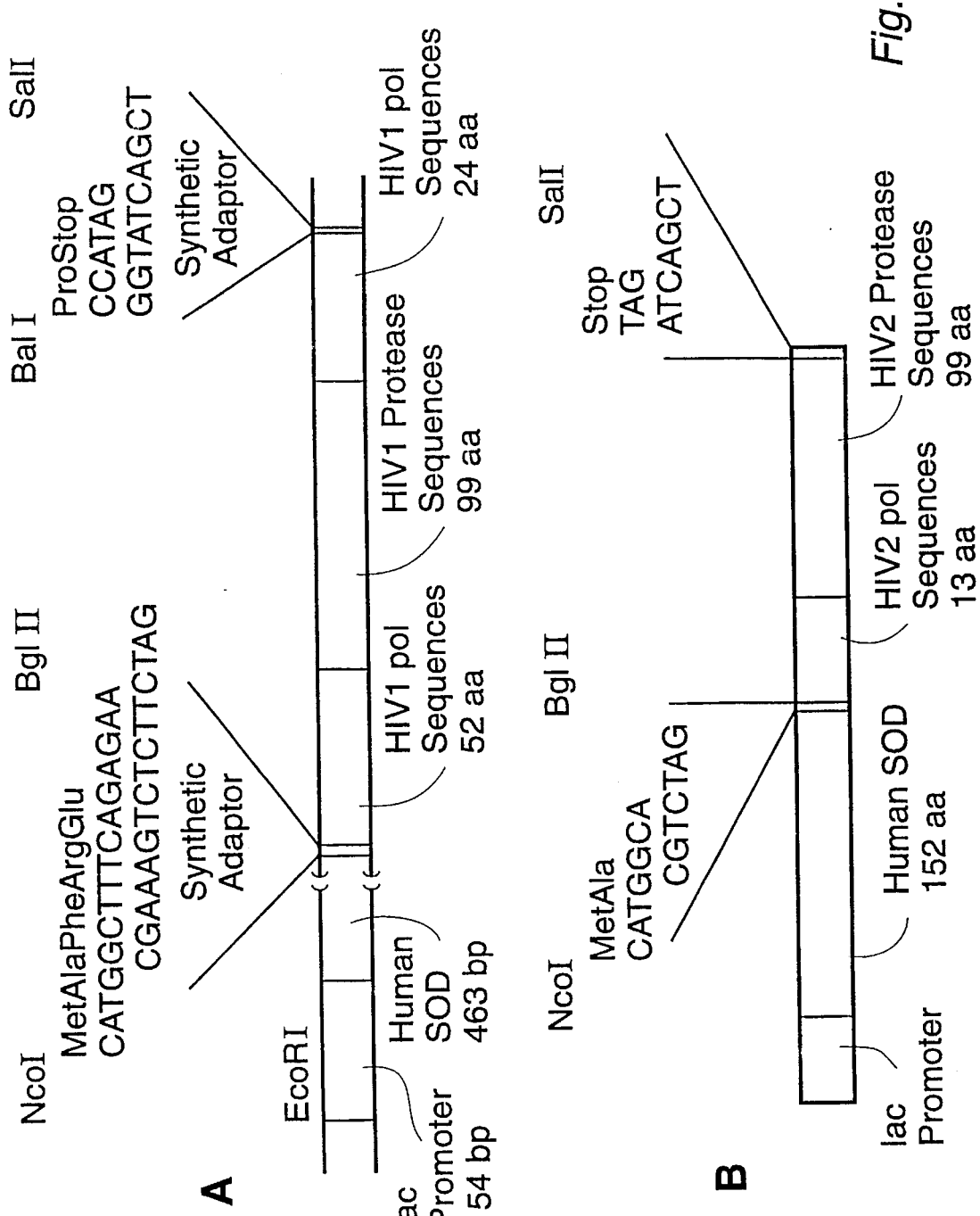
FIGS. 1A and 1B set forth expression vectors for the expression of HIV-1 protease (FIG. 1A) and HIV-2 protease (FIG. 1B).

The present invention relates to i) non-peptide protease-binding compounds, ii) methods for binding new and known non-peptide compounds to proteases, iii) methods for detecting protease inhibition, and iv) methods for using non-peptide protease-binding compounds to inhibit proteases, and in particular, viral proteases.

1. Non-peptide Protease Binding Compounds

Traditionally, the search for pharmacologic compounds capable of interacting with a particular biomolecule has involved random screening. More recently, however, the knowledge of specific characteristics of the biomolecule have been used as a starting point.

The binding compounds of the present invention have been developed using computer analysis of the three-dimensional structure of HIV-1 protease. See R. L. DesJarlais, et al., *Proc. Nat. Acad. Sci.* 87:6644 (1990). Using a set of coordinates for the protease, a computer program, and a compound database, putative protease-binding compounds were identified based on a simple function of interatomic distances. The primary candidate was found to be the aryl piperidinyl halobutyrophenone, bromoperidol.

An analog of this lead compound is the known antipsychotic, 4-[4-(p-chlorophenyl)-4-hydroxy-piperidinol-]4'-fluorobutyrophenone ("haloperidol"). To explore variations of the molecular formula, a series of synthetic compounds of related structure was made. The formulas for these compounds are shown in Table 1. The compounds in this table and throughout this specification are referred to by code numbers, which are used for convenience only, and are strictly arbitrary for purposes of this invention.

TABLE 1
Protease Binding Compounds
| Compound Code No. | Formula |
|---|---|
| UCSF1 | 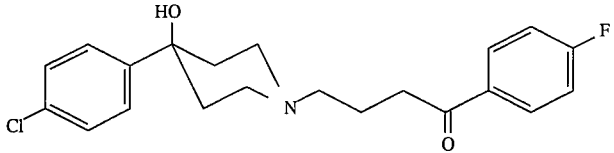 |
| UCSF2 | 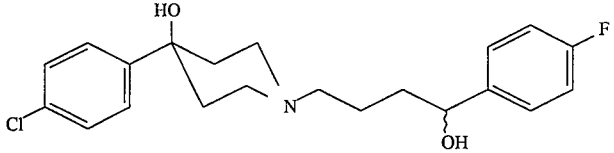 |
| UCSF3 | 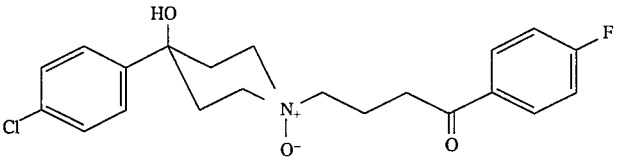 |
| UCSF4 | 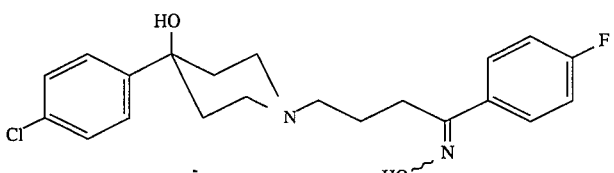 |
| UCSF5 | 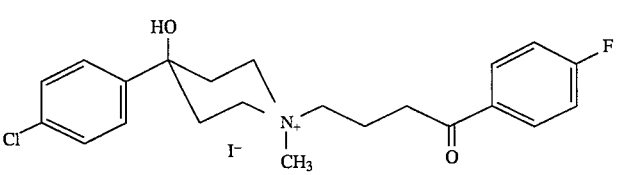 |
| UCSF6 | 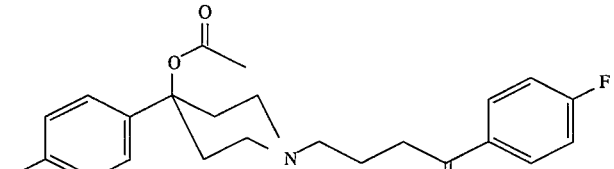 |
| UCSF7 | 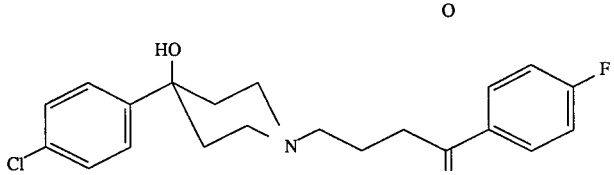 |
| UCSF8 | 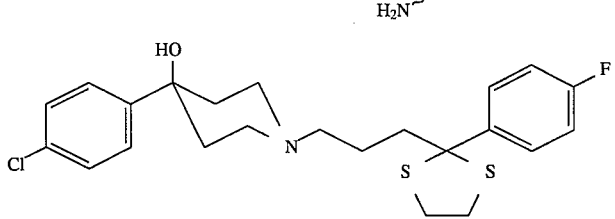 |

TABLE 1-continued

Protease Binding Compounds

| Compound Code No. | Formula |
|---|---|
| UCSF10 | |
| UCSF11 | |
| UCSF12 | |
| UCSF13 | (mixture of UCSF12 and UCSF64) |
| UCSF14 | |
| UCSF15 | |
| UCSF16 | |
| UCSF17 | |

TABLE 1-continued
Protease Binding Compounds
| Compound Code No. | Formula |
|---|---|
| UCSF18 | 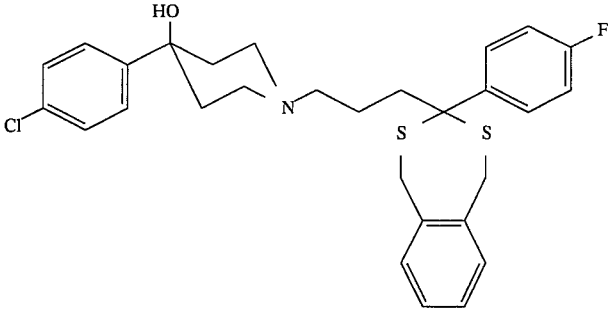 |
| UCSF19 | 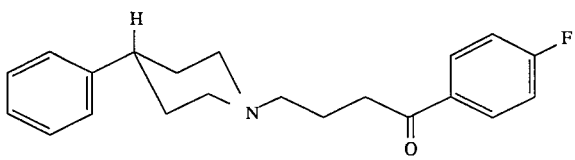 |
| UCSF20 | 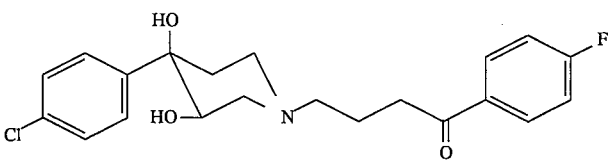 |
| UCSF21 | 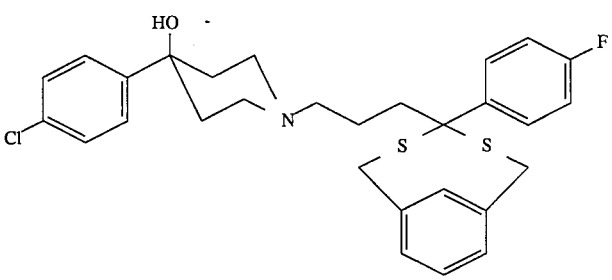 |
| UCSF22 | 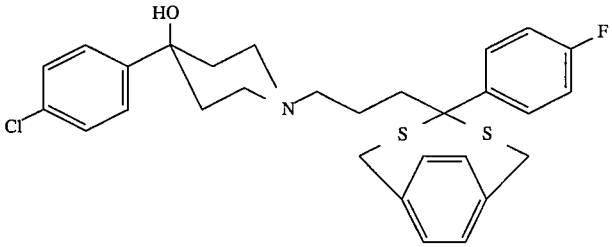 |
| UCSF23 | 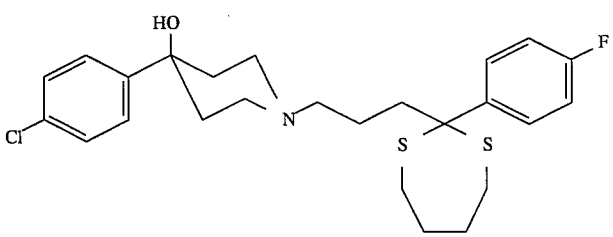 |

TABLE 1-continued
Protease Binding Compounds
| Compound Code No. | Formula |
|---|---|
| UCSF24 | 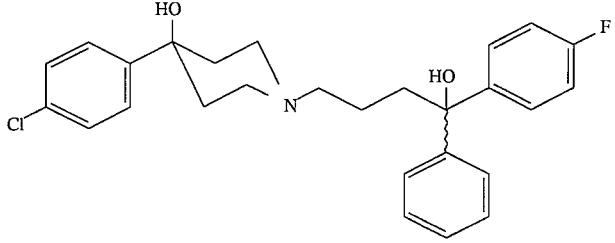 |
| UCSF25 | 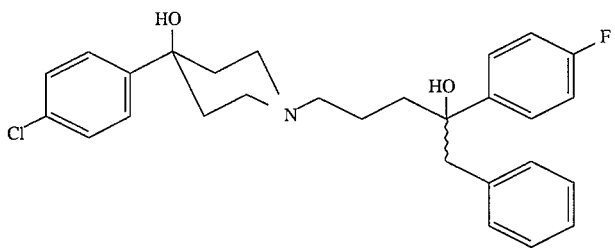 |
| UCSF27 | 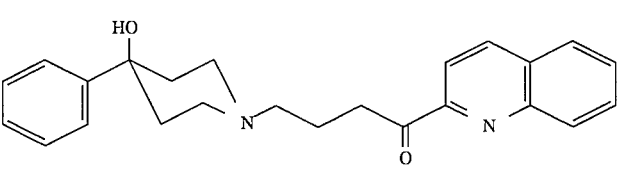 |
| UCSF28 | 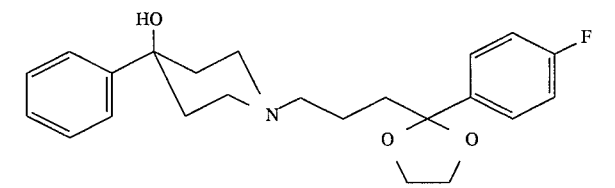 |
| UCSF29 | 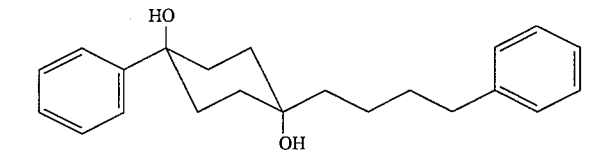 |
| UCSF30 | 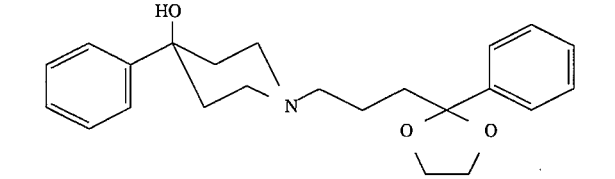 |
| UCSF31 | 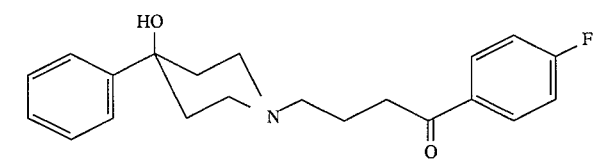 |

TABLE 1-continued

Protease Binding Compounds

| Compound Code No. | Formula |
|---|---|
| UCSF32 | |
| UCSF33 | |
| UCSF34 | |
| UCSF35 | |
| UCSF36 | |
| UCSF37 | |
| UCSF39 | |

TABLE 1-continued

Protease Binding Compounds

| Compound Code No. | Formula |
|---|---|
| UCSF40 | |
| UCSF41 | |
| UCSF42 | |
| UCSF43 | |
| UCSF44 | |
| UCSF45 | |
| UCSF46 | |

TABLE 1-continued

Protease Binding Compounds

| Compound Code No. | Formula |
|---|---|
| UCSF47 | |
| UCSF48 | |
| UCSF49 | |
| UCSF50 | |
| UCSF51 | |
| UCSF52 | |
| UCSF53 | |

TABLE 1-continued

Protease Binding Compounds

| Compound Code No. | Formula |
|---|---|
| UCSF54 | |
| UCSF55 | |
| UCSF56 | |
| UCSF57 | |
| UCSF58 | |
| UCSF59 | |
| UCSF60 | |

TABLE 1-continued
Protease Binding Compounds
| Compound Code No. | Formula |
|---|---|
| UCSF61 | 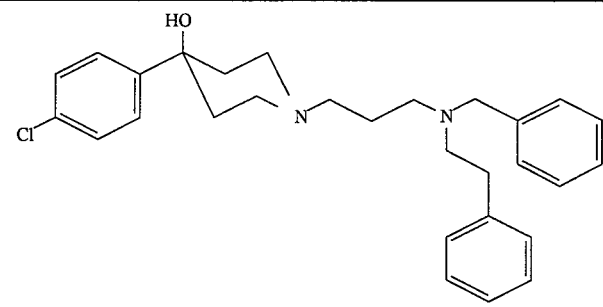 |
| UCSF62 | 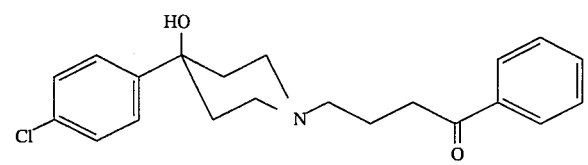 |
| UCSF63 | 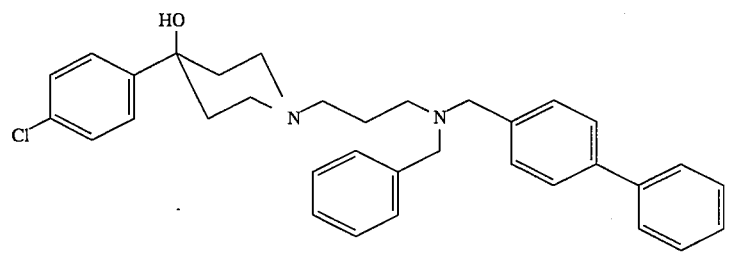 |
| UCSF64 | 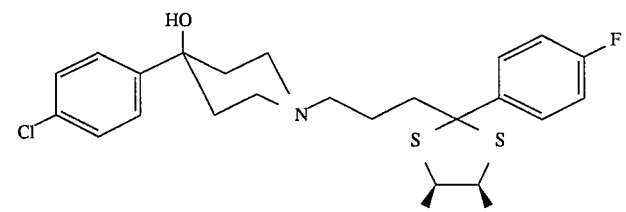 |
| UCSF65 | 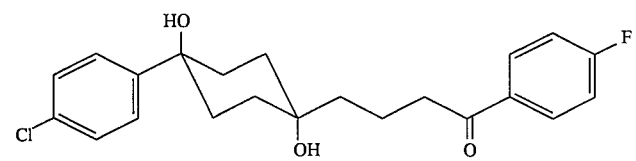 |
| UCSF66 | 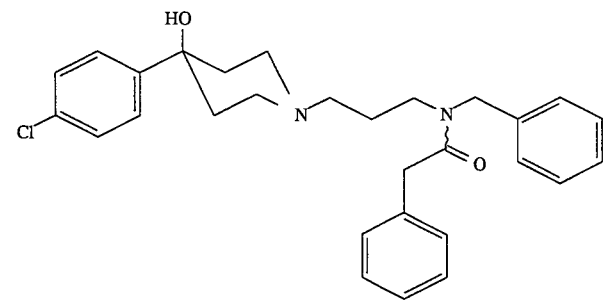 |

TABLE 1-continued

Protease Binding Compounds

| Compound Code No. | Formula |
|---|---|
| UCSF67 | |
| UCSF68 | |
| UCSF69 | |
| UCSF70 | |
| UCSF71 | |
| UCSF72 | |
| UCSF73 | |

TABLE 1-continued

Protease Binding Compounds

| Compound Code No. | Formula |
|---|---|
| UCSF74 | (structure) |
| UCSF75 | (structure) |
| UCSF76 | (structure) |
| UCSF77 | (structure) |
| UCSF78 | (structure) |
| UCSF79 | (structure) |
| UCSF80 | (structure) |

TABLE 1-continued
Protease Binding Compounds
| Compound Code No. | Formula |
|---|---|
| UCSF81 | 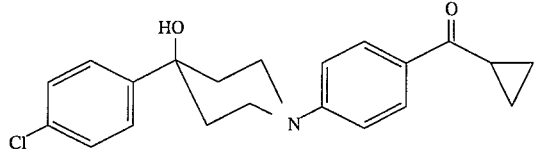 |
| UCSF82 | 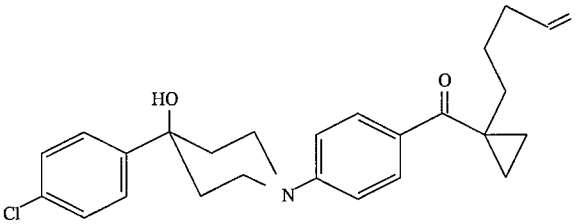 |
| UCSF83 | 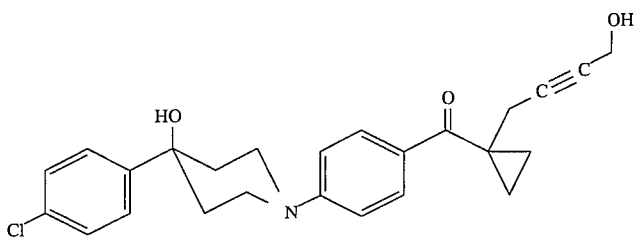 |
| UCSF84 | 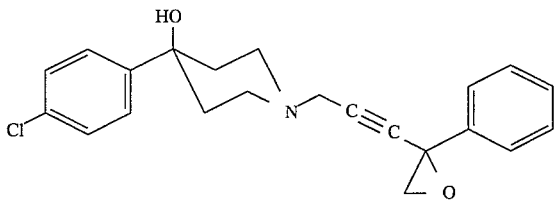 |
| UCSF86 | 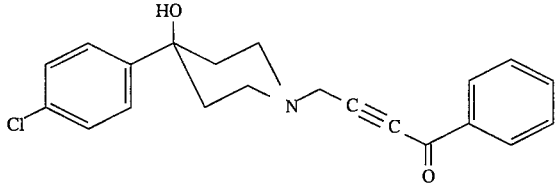 |
| UCSF142 | 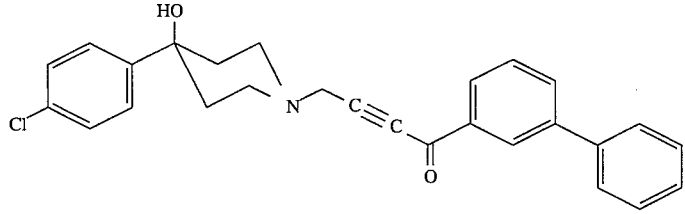 |
| UCSF231 | 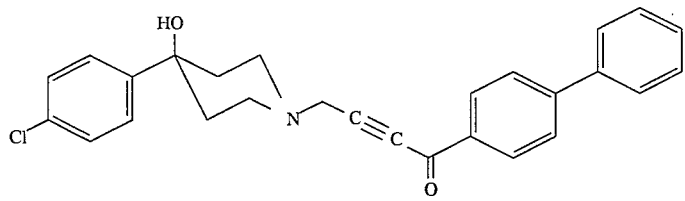 |

TABLE 1-continued

Protease Binding Compounds

| Compound Code No. | Formula |
|---|---|
| UCSF115 | 4-chlorophenyl-4-hydroxypiperidine linked via N-oxide to CH=CH-C(=O)-4-fluorophenyl |
| UCSF191 | 4-chlorophenyl-4-hydroxypiperidine linked via N to CH=CH-C(=O)-4-fluorophenyl |
| UCSF178 | 4-chlorophenyl-4-hydroxypiperidine linked via N-CH2-C(S-CH2CH2-OH)=CH-C(=O)-phenyl |

Compounds UCSF11 and UCSF17 are butyrophenones. Compounds UCSF1-UCSF10, UCSF12-UCSF16, UCSF18-UCSF28, UCSF30-UCSF40, UCSF42-UCSF44, UCSF46-UCSF53, UCSF55-UCSF64, and UCSF66-UCSF84 are aryl piperidinyl derivatives. Within this group, UCSF1, UCSF3, UCSF5, UCSF6, UCSF15, UCSF19, UCSF20, UCSF31, UCSF34, UCSF43, UCSF44, UCSF50, UCSF60, UCSF62, UCSF68, UCSF69, and UCSF74 are butyrophenones, including compounds UCSF1, UCSF3, UCSF5, UCSF6, UCSF15, UCSF19, UCSF20, UCSF31, UCSF50, UCSF60, UCSF68, UCSF69, and UCSF74 which are halobutyrophenones. Compounds UCSF70 and UCSF84 are aryl piperidinyl epoxides.

Compounds UCSF29, UCSF41, UCSF45, UCSF54 and UCSF65 are cyclohexanol derivatives, including compounds UCSF41, UCSF54 and UCSF65 which are chlorophenylcyclohexanol derivatives. Compounds UCSF45 and UCSF65 are butyrophenones, including compound UCSF65 which is a halobutyrophenone.

Compounds UCSF86, UCSF142 and UCSF231 contain ynone moieties, and compounds UCSF115, UCSF178 and UCSF191 contain α,β-unsaturated ketons. These three subsets of compounds are among those which bind covalently to HIV-1 and HIV-2 proteases.

2. Binding Methods

Binding of the above-named compounds is in part a function of solubility. The compounds generally exhibit a low solubility in aqueous media. To enhance the solubility of these compounds in aqueous solutions, the invention contemplates the use of a co-solvent. The preferred co-solvent is dimethylsulfoxide (DMSO). The concentration range of DMSO is between 0.1% and 10%, with a preferred range of between 0.5% and 5%.

Binding is also a function of compound concentration. Where only in vitro binding to the protease is desired, millimolar concentrations of the above-named compounds can be used. However, where cytotoxicity is a concern, generally micromolar concentrations must be used (see section iv below for a more extensive discussion of cytotoxicity).

Particular attention to binding reaction conditions is important with epoxide compounds within the scope of this invention. Because of the tendency of epoxides to undergo acid catalyzed hydrolysis, the binding of these derivatives should be done under conditions that favor the reaction with the protease such as, for example, under conditions of high pH.

The present invention contemplates using the above-named compounds to label proteases. In one case, the protease can be "labelled" by virtue of an increase in molecular weight due to covalent binding of the compound. The increase in molecular weight can be detected by any sizing technique, such as HPLC, SDS-PAGE, and mass spectroscopy.

The present invention also contemplates labelling methods which involve attaching to the compounds or integrating into their structure at least one moiety capable of detection, either by signal emission or by specific binding. Moieties such as these are generally intended to facilitate the detection of the protease or of molecules bound to the protease. Examples of types of moieties useful for this purpose are enzymes, fluorophores, high-affinity conjugates, chemophores and radioactive atoms (radioisotopes). Examples of enzymes are alkaline phosphatase, β-galactosidase and glucose oxidase. An example of an affinity conjugate system is the biotin-avidin system. An example of a fluorophore is fluorescein. An example of a chemophore is luminol. Examples of radiolabels are $^3H$, $^{14}C$, $^{231}I$ and $^{125}I$. Other examples can be used as well.

As indicated above, single or multiple labels can be present in a single complex, with multiple labels being the same or different. In the use of the invention for facilitating the detection of protease, preferred labels are tritium $^3H$ and $^4C$. A preferred label for facilitating the detection of molecules bound to the compounds is biotin.

The present invention contemplates using labelled analogs of the compounds disclosed herein to label retroviral proteases in tissues and cells, including lymphocytes. This type of labelling is a measure of viral infectivity and can be used diagnostically to detect disease.

Quantitation of protease by this in vivo labelling technique can be performed in many ways known to the art, including methods using tritiated analogs of the compounds and autoradiography of treated cells on microscope slides. In addition, there are a number of automated detection systems described for fluorescent staining that also can be employed. See, for example, Resnick, et al., U.S. Pat. Nos. 4,125,828 and 4,207,554, hereby incorporated herein by reference.

The present invention also contemplates the in vitro use of the compounds disclosed herein as topologic and mechanistic probes of retroviral proteases. In one embodiment, the topologic assay utilizes labelled compounds whose protease binding sites are known.

As noted earlier, the compounds of the present invention were developed using computer analysis of the known, three-dimensional structure of HIV-1 protease. See R. L. DesJarlais, et al., *Proc. Nat. Acad. Sci.* 87:6644 (1990). The binding site of each compound was identified based on docking and interatomic distance measurements.

The known protease-binding sites of the compounds of the invention allow the compounds to be used in the determination of binding sites for other (peptide and non-peptide) compounds. In one embodiment, a compound of this invention is used in a competition assay with a second protease-binding compound whose protease binding site is to be tested. The compounds of this invention can be added to the protease together or in any sequential order. Where the compound is labelled, it is preferred that the second protease-binding compound be added first to allow it to block (if possible) the binding site. Similarly, where the second protease-binding compound is labelled, it is preferred that the compounds of this invention be added first.

Compounds of this invention that bind covalently are particularly useful in topologic assays. The covalent binding permits the inclusion of stringent washing steps to reduce background label.

The present invention also contemplates binding methods to immobilize protease. In one embodiment, the present invention contemplates using a protease-binding compound of the invention that will bind non-covalently to HIV protease to immobilize the protease on a solid support. Such a method is useful in the purification of the protease.

3. Protease Inhibition Assays

Typical in vitro protease assays measure a change in the hydrolysis of a peptide substrate. For HIV-1 protease, the peptide substrate is usually the decapeptide Ala-Thr-Leu-Asn-Phe-Pro-Ile-Ser-Pro-Trp (SEQ ID No. :1) corresponding to the HIV-1 carboxy-terminal auto-processing site (underlined residues correspond to the cleavage site). The reaction is allowed to proceed for a specific time and the reaction products are separated and quantitated to determine the extent to which the decapeptide is cleaved into two pentapeptides.

Such an assay is useful to detect potential pharmacologic compounds that inhibit the protease. However, it has been found in accordance with the present invention, that greater sensitivity of this assay is achieved by increasing the salt concentration in the buffered media. In one embodiment, a significantly greater sensitivity is achieved using an assay buffer containing 1M NaCl. Using this higher salt concentration, the present invention allows for the determination of the concentration of inhibiting compound that will result in 50% inhibition of protease reactivity, i.e., the compound's "$IC_{50}$" (see Table 2).

TABLE 2

| Compound | $IC_{50}$ (μM) | | |
|---|---|---|---|
| Code No. | 0.2M NaCl | 0.5M NaCl | 1.0M NaCl |
| UCSF1 | 440 | 330 | 125 |
| UCSF8 | 73 | 32 | 15 |
| UCSF29 | 1400 | 625 | 128 |
| UCSF42 | 375 | 80 | 30 |
| UCSF48 | 500 | 260 | 7 |

The present invention also contemplates novel in vivo assays to measure protease activity and protease inhibition. In one embodiment, the present invention contemplates an inhibition assay using bacterial cells expressing HIV protease. Where the inhibitors inhibit protein processing, an increase in the production of intermediate proteins can be detected and quantitated. The assay is useful to screen for inhibiting pharmacologic agents, including the compounds disclosed herein.

Bacterial expression of HIV-1 protease has been described. See C. Debouck, et al., *Proc. Nat. Acad. Sci.* 84:8903 (1987); N. E. Kohl, et al., *Proc. Nat. Acad. Sci.* 85:4686 (1988); and P. Darke, et al., *J. Biol. Chem.* 264:2307 (1989). However, inhibition of the protease has uniformly been assayed in vitro by collecting and/or purifying the protease from the supernatants of bacterial cell lysates.

The bacterial cell inhibition assay of the present invention measures inhibition of HIV protease by directly introducing the inhibitor to the bacterial cells in vivo. See R. L. DesJarlais, et al., *Proc. Nat. Acad. Sci.* 87:6644 (1990). In this manner, the bacterial cell inhibition assay of the present invention detects changes in protein expression as a function of protease inhibition.

The bacterial cell inhibition assay of the present invention is not limited by the particular expression vector or the specific bacterial cell line. Numerous expression systems are well known in the art. See T. Maniatis, et al., *Molecular Cloning, A Laboratory Manual* (Cold Spring Harbor Press, New York 1982). Furthermore, a number of HIV protease expression systems are described. For example, the pPRT expression system can be used with *E. coli*. See N. E. Kohl, et al., *Proc. Nat. Acad. Sci.* 85:4686 (1988), and P. Darke, et al., *J. Biol. Chem.* 264:2307 (1989). Alternatively, the pAS expression system can be utilized with *E. coli*. See C. Debouck, et al., *Proc. Nat. Acad. Sci.* 84:8903 (1987). Similarly, the pBR322 expression system can be employed with *E. coli*. A. G. Tomasselli, et al., *Biochemistry* 29:264 (1990).

Complete expression systems are available through the AIDS Research and Reference Reagent Program (ARRRP). For example, bacteria transformed with the pHRT25 vector have been contributed by Dr. Coif (see the January 1991 ARRRP Catalog, p. 107). In addition, numerous suitable bacterial cell lines are available commercially, such as for example from Bethesda Research Laboratories.

The system for HIV-1 and HIV-2 protease expression in bacterial cells used in the inhibition assay of the present invention is shown in FIG. 1A and FIG. 1B, respectively. This system utilizes plasmid pSOD/PR179 to express the protease of HIV-1 as a fusion protein with human superoxide dismutase (hSOD). See L. Babé, et al., *Protein and Pharmaceutical Engineering* (Wiley-Liss, Inc. 1990) (pages 71–88). See also S. Pichuantes, et al., *J. Biol. Chem.* 265:13890 (1990). To make this construct, the 522 base pair Bgl II/Bal I DNA restriction fragment of the pol gene of the ARV-2 SF2 strain was ligated to the Nco I/Sal I-digested vector pSODCF2 using synthetic adapters. The synthetic oligonucleotides added to the 5' end of the HIV-1 DNA fragment regenerated an NcoI restriction site, encoded a Met, an Ala and three residues of the pol gene product (PheArgGlu) (SEQ ID No.: 2), and regenerated the Bgl II restriction site. The synthetic adapter added at the 3' end of the viral DNA fragment regenerated a Bal I restriction site, encoded an additional Pro residue of the pol gene and a termination codon and regenerated the Sal I restriction site. The resulting plasmid pSOD/PR179 encodes hSOD (153 residues) fused to amino acids 5 (Asp) to 179 (Trp) of the pol region which includes the putative viral protease. The carboxyl-terminal Asn and the termination codon of hSOD were replaced by Met and Ala.

To assay for protease inhibition in vivo, cultures of E. coli strain D1210 (obtained from BRL) harboring plasmid pSOD/PR179 are grown to $OD_{650}=0.4$ at which time isopropyl β-thiogalacytopyranoside (IPTG) is added for induction. Aliquots of the cultures are then mixed with potential protease inhibitors. The aliquots are then further cultured for sampling at different time intervals (for example, at 15, 30, 60, and 120 minutes). The samples are pelleted by centrifugation and processed to isolate cell protein. Isolated protein is then loaded onto a polyacrylamide gel and subjected to electrophoresis. The gels are then immunoblotted and probed with antibodies to the HIV protease.

The hSOD-protease polyprotein consists of the 154 amino acids of hSOD, followed by 5 amino acids encoded by a synthetic linker, the 55 N-terminal amino acids of the pol reading frame (amino acids 2–56), the 99 amino acids of the protease, and finally the first 24 amino acids of the reverse transcriptase (amino acids 156–180). This 38-kDa fusion protein contains the naturally occurring protease-specific cleavage sites at the N terminus of the protease and at the protease-reverse transcriptase junctions.

Where autoprocessing by the protease is uninhibited the 11-kDa mature protease is detected. On the other hand, where autoprocessing is inhibited, polypeptides corresponding to processing intermediates are observed (38 and 35-kDa) in larger amounts as compared to untreated samples.

Another method of assaying for protease inhibition in vivo involves the use of an HIV vector system designed to produce replication-defective virions (Page, et al., Virol. 64:5270 (1990)), and measurements of the effect of the test compounds on capsid polyprotein processing as well as on viral infectivity in vivo. Virions are produced by co-tansfection of COS-7 cells with two expression vectors, one consisting of the HIV proviral genome where the gp160 envelope sequences are replaced by the guanidyl phosphate ribotransferase (gpt) gene, and the other containing the gp160 sequences. The transfected cells are then treated with a test compound for short periods of time, and the level of infectious particles in the culture supernatant and the level of capsid protein processing are determined. Quantitation of infectious particles in the culture supernatant and the level of capsid protein processing are determined. Quantitation of infectious particles in the culture supernatant is achieved by adsorption of HeLa cells that express human CD4 and subsequent selection for gpt-expressing infected cells. The drug-resistant colonies are counted and reduction in infectivity is interpreted as a measure of the protease inhibition when accompanied by a concomitant reduction in viral polyprotein processing.

4. Protease Inhibition

Evaluation of the compounds of this invention for in vivo inhibition must first begin with an assessment of cytotoxicity. Only then can changes in protein processing due to cell death be sorted out from changes due to specific protease inhibition. Furthermore, using the $IC_{50}$ value determined for a compound (see above), the cytotoxicity determination allows for a calculation of a therapeutic index.

Various assays can be used to determine the toxicity of the compounds on cells in culture. For example, the MTT assay measures mitochondrial metabolic activity, while the $^3[H]$ thymidine incorporation assay measures replication competency, and the trypan blue exclusion measures cell membrane integrity. The results obtained for the three different assays when testing compound UCSF1 (see Table 1 ) show that UCSF1 is toxic.

TABLE 3

| | Percent Cell Viability | | | | |
|---|---|---|---|---|---|
| Inhibitor Concentration (μM) | MTT Assay; 4 h; COS-7 | MTT Assay; 24 h; COS-7 | MTT Assay; 72 h; HUT-78 | $^3[H]$ Thymidine Incorporation; 72 h; HUT-78 | Tryptan Blue; 72 h; HUT-78 |
| 0 | 100 | 100 | 100 | 100 | 100 |
| 200 | 62 | 34 | 0.00 | 3 | 0 |
| 500 | 46 | 21 | 0 | 2 | 0 |

Note that comparable levels of toxicity are observed for human T-lymphocyte (HUT-78) cells, which are generally used in HIV infectivity assays, monkey kidney cells (COS-7) used in out-transfection assays, and in human epitheloid/ lymphocytic hybrid cells (HeLa/T4) used in the infectivity assay of the present invention (see below).

The MTT stain assay is a standard viability assay used to obtain $LD_{50}$ values for all the compounds of the present invention, The tetrazolium salt MTT (3-(4,5-dimethylthiazol-2-yl)2,5-diphenyltetrazolium bromide) is cleaved by dehydrogenases in active mitochondria of living cells to yield a change in color from yellow to purple. The $LD_{50}$ is defined as the concentration that reduces viability by 50% during the experimental incubation period. The MTT assay works well on all the cells tested, it is quantitative, a large number of samples can be assayed at once, and there is no need for radioisotopes.

The potential therapeutic index ($LD_{50}/IC_{50}$) can be calculated to determine what concentrations could be tried in the in vivo assays. The values are generally low (See Table 4), since many compounds of this type are toxic above or near the in vitro $IC_{50}$ concentrations.

TABLE 4

| Compound UCode No. | $LD_{50}$ ($\mu$M, 6 h) | HIV-1 Protease $IC_{50}$ ($\mu$M) 1M NaCl | HIV-1 Protease Therapeutic Index ($LD_{50}/IC_{50}$) | HIV-2 Protease $IC_{50}$ ($\mu$M) 1M NaCl | Solubility ($\mu$M) |
|---|---|---|---|---|---|
| UCSF1 | 500 | 125 | 4 | 140 | >500 |
| UCSF2 |  | 200 | 0.5 | 700 | >250 |
| UCSF3 | >500 | 100 | >2.5 | 135 | <250 |
| UCSF4 |  | 100 | 0.7 | 116 | >250 |
| UCSF5 | >500 | 79 | >6.3 | >1000 | >250 |
| UCSF6 | 250 | 725 | 0.3 | 533 | >250 |
| UCSF7 |  | 100 | 0.9 | 200 | >250 |
| UCSF8 | 60 | 15 | 4 | 100 | >250 |
| UCSF10 | 30 | 15 | 2 | 88 | <100 |
| UCSF11 | 250 | 750 | 0.3 | 310 | <250 |
| UCSF12 | 35 | 350 | 0.5 | 50 | <250 |
| UCSF13 | 10 | 10 | 1 | 24 | <250 |
| UCSF14 | 500 | 50 | 10 | 90 | 500 |
| UCSF15 | ND | 150 | 0.3 | 250 | >250 |
| UCSF16 | 150 | 75 | 2 | 238 | >250 |
| UCSF17 | 500 | 1200 | 0.4 | ND | >250 |
| UCSF18 | 35 | 25 | 1.4 | 10 | >250 |
| UCSF19 | ND | 250 | ND | 323 | ND |
| UCSF20 | ND | 675 | 0.26 | ND | >250 |
| UCSF21 | >500 | 25 | >20(10) | 75 | <250 |
| UCSF22 | >500 | 100 | 5(0.5) | 54 | <50 |
| UCSF23 | 25 | 20 | 1.25 | 71 | >250 |
| UCSF24 | 25 | 62 | 0.4 | ND | >200 |
| UCSF25 | 20 | 87 | 0.2 | 75 | ND |
| UCSF27 | 400 | 198 | 2(1) | ND | <200 |
| UCSF28 | >500 | 410 | 1.2 | ND | >500 |
| UCSF29 | 160 | 128 | 1.2 | ND | >250 |
| UCSF30 | >250 | 265 | 1 | 500 | >250 |
| UCSF31 | >250 | 230 | >1.1 | 495 | >250 |
| UCSF32 | 25 | 60 | 0.4 | 80 | ND |
| UCSF33 | 10 | 7 | 1.4 | 7 | <50 |
| UCSF34 | >500 | 400 | >1.25 | 288 | >500 |
| UCSF35 | >500 | 650 | >0.8 | ND | >500 |
| UCSF36 | 50 | 32 | 1.4 | 53 | <50 |
| UCSF37 | 50 | 39 | 1.3 | 34 | <200 |
| UCSF39 | 90 | 75 | 1.2 | 135 | >500 |
| UCSF40 | 100 | 80 | 1.25 | 200 | <100 |
| UCSF41 | 90 | 160 | 0.6 | ND | >500 |
| UCSF42 | 160 | 30 | 5.3 | 67 | 500 |
| UCSF43 | 350 | 50 | 7(1) | 27 | >500 |
| UCSF44 | 200 | 35 | 5.7(0.7) | 43 | <25 |
| UCSF45 | ND | >1000 | ND | ND | ND |
| UCSF46 | 20 | 30 | 0.7 | 34 | >500 |
| UCSF47 | 15 | 90 | 0.2 | 1.5 | >500 |
| UCSF48 | ND | 7 | ND | 10 | ND |
| UCSF49 | 120 | 100 | 1.2 | 180 | <50 |
| UCSF50 | 90 | 100 | 0.9–0.6 | 126 | >500 |
| UCSF51 | 45 | 40 | 1.1–0.5 | 68 | <250 |
| UCSF52 | 10 | 20 | 0.5 | 19 | <250 |
| UCSF53 | 500 | >2500 | <0.2–0.1 | ND | <50 |
| UCSF54 | 190 | 2500 | <0.08 | ND | >500 |
| UCSF55 | 60 (4 h) | 2500 | <0.02 | >2500 | >500 |
| UCSF56 | 20 (4 h) | 20 | 1–0.5 | 11 | <500 |
| UCSF57 | 25 (4 h) | 10 | 2.5–1.5 | 14 | <500 |
| UCSF58 | 110 (4 h) | 300 | <0.3 | 290 | >500 |
| UCSF59 | 45 (4 h) | 8 | 5.6–2.5 | 7 | <500 |
| UCSF60 | >500 (4 h) | 2500 | >0.2 | >2500 | >500 |
| UCSF61 | 40 | 220 | 0.2–0.4 | 230 | <500 |
| UCSF62 | 380 | 100 | 3.8–2.6 | 40 | <250 |
| UCSF63 | 25 | 18 | 1.4–0.3 | 15 | >500 |
| UCSF64 | 25 | 16 | 1.6–0.3 | 29 | <50 |
| UCSF65 | 250 | ND | ND | ND | <100 |
| UCSF66 | 25 | 70 | 0.3 | 48 | <250 |
| UCSF67 | >25 | 80 | 0.3 | 10 | >25 |
| UCSF68 | 100 | 105 | 1–0.5 | 48 | <500 |
| UCSF69 | 220 | 50 | 4.4–0.8 | 60 | <100 |
| UCSF70 | 120 | 750 | 0.16–0.07 | 350 | >500 |
| UCSF71 | 500 | >2500 | <0.2–0.1 | 2000 | <200 |
| UCSF72 | 260 | 750 | 0.3–0.1 | ND | >500 |
| UCSF73 | 360 | 100 | 3.6–0.8 | 188 | <500 |
| UCSF74 | ND | ND | ND | ND | ND |
| UCSF75 | 200 | 50 | 4–0.2 | 13 | <50 |

TABLE 4-continued

| Compound UCode No. | LD$_{50}$ (µM, 6 h) | HIV-1 Protease | | HIV-2 Protease IC$_{50}$ (µM) 1M NaCl | Solubility (µM) |
|---|---|---|---|---|---|
| | | IC$_{50}$ (µM) 1M NaCl | Therapeutic Index (LD$_{50}$/IC$_{50}$) | | |
| UCSF76 | 440 | 1650 | 0.27–0.1 | ND | >500 |
| UCSF77 | 500 | 2500 | 0.2–0.1 | 500 | >500 |
| UCSF78 | 35 | 39 | 0.9–0.5 | 167 | >500 |
| UCSF79 | 35 | 30 | 1–0.3 | 68 | >250 |
| UCSF80 | 40 | 33 | 1.2–0.5 | 58 | >250 |
| UCSF81 | >250 | 200 | >1.25 | 1000 | >250 |
| UCSF82 | >250 | 100 | 2.5–1.5 | 800 | <100 |
| UCSF83 | >250 | 15 | 17–7 | 78 | >250 |
| UCSF84 | 100–165 | 150 | 1.1–0.3 | | >250 |
| UCSF86 | 15–20 | 20 | 0.7–0.5 | | >60 |
| UCSF115 | 250 | 30 | 8–6.5 | | 250 |
| UCSF142 | 35 | 63 | 0.56 | | 100 |
| UCSF178 | >250 | 140 | >1.8–0.5 | | 150 |
| UCSF191 | 22 | 80 | 0.3–0.1 | | >150 |
| UCSF231 | 10 | 100 | <0.1 | | ND |

These results indicate that in vivo inhibition measurements can only be done for very short periods of time (4 to 6 hours) in order to limit their toxicity.

EXPERIMENTAL

The following examples serve to illustrate certain preferred embodiments and aspects of the present invention and are not to be construed as limiting the scope thereof.

In these examples, the following abbreviations are used:

| | |
|---|---|
| Ag | antigen |
| amu | atomic mass units |
| Aldrich | Aldrich Chemical Co., Milwaukee, Wisconsin |
| Analtech | Analtech, Newark, Delaware |
| BACHEM | BACHEM Bioscience Inc., Phildelphia, Pennsylvania |
| bp | base pairs |
| BRL | Bethesda Research Laboratories, Gaithersburg, Maryland |
| °C. | degrees Centigrade |
| CDCl$_3$ | deuterochloroform |
| Ci | Curies |
| CI | chemical ionization (mass spectrometry) |
| cm | centimeters |
| DEAE | O-diethylaminoethyl |
| DMSO | dimethyl sulfoxide |
| DNEN | Du Pont - New England Nuclear, Wilmington, Delaware |
| DTT | dithiothreitol |
| EDTA | ethylenediaminetetraacetic acid |
| EI | electron ionization (mass spectrometry) |
| ELISA | enzyme-linked immunosorbent assay |
| eq | equivalents |
| GSA | guanidinated bovine serum albumin |
| HEPES | N-2-hydroxyethylpiperazine-N'-2-ethanesulfonic acid |
| HIV | human immunodeficiency virus |
| HPLC | high performance liquid chromatography |
| hSOD | human superoxide dismutase |
| IPTG | isopropyl β-D-thiogalactopyranoside |
| kD | kilodaltons |
| L | liters |
| LSIMS | liquid secondary ionization mass spectrometry |
| M | molar |
| mA | milliamperes |
| m/e | ion mass |
| mL | milliliters |
| mm | millimeters |
| mmol | millimoles |
| mp | melting point |
| mS | milliSieberts |
| MS | mass spectrometry: spectra obtained on a Kratos MS50 instrument, Kratos Analytical, Manchester, England |
| MTT | 3-(4,5-dimethylthiazol-2-yl)-2,5-diphenyltetrazolium bromide |
| MW | molecular weight |
| nLe | norleucine |
| PAA | pepstatin A agarose |
| PBS | phosphate-buffered saline |
| PMSF | phenylmethylsulfonyl fluoride |
| µg | micrograms |
| µL | microliters |
| µM | micromolar |
| µm | micrometers |
| µmol | micromoles |
| nmol | nanomoles |
| nm | manometers |
| NMR | nuclear magnetic resonance: spectra obtained on a 300 MHz Fourier Transform Spectrometer |
| OD | optical density |
| RPM | revolutions per minute |
| PAGE | polyacrylamide gel electrophoresis |
| PBS | phosphate-buffered saline |
| SDS | sodium dodecyl sulfate |
| Sigma | Sigma Chemical Co., St. Louis, Missouri |
| TCA | trichloroacetic acid |
| THF | tetrahydrofuran |
| TLC | thin layer chromatography |
| V | volts |
| W | watts |

Recombinant Protein Preparations. Recombinant HIV-1 protease was expressed and purified from *E. coli* strain D1210 using the pSOD/PR179 expression vector (FIG. 1A). The plasmid was constructed as described above.

HIV-2 protease was expressed in *Saccharomyces cerevisiae* strain AB110 from the plasmid pHIV2PR115 (FIG. 1B). The construction of the recombinant plasmids for the expression of the HIV-2 protease was as follows. A synthetic HIV-2 protease gene was first constructed using a 360-bp Xba I - Sal I DNA fragment produced by 17 overlapping synthetic oligonucleotides of 18, 27, and 45 nucleotides in length. The Xba I, Bgl II, and Sal I restriction sites were included to facilitate subcloning of the final construction. The BstE II and Hpa II restriction sites present in the coding region of the 99-amino acid protease were introduced to permit dissection of the gene.

To create the bacterial expression plasmid pSOD/HIV2PR113, a 339-bp synthetic Bgl II-Sal I DNA fragment encoding the 99-amino acids HIV-2 protease and containing 13 additional residues at its NH$_2$ terminus was cloned into the plasmid pSOD/PR179. The resulting plasmid encodes a hSOD/HIV-2 protease hybrid precursor whose expression is under the control of the tac promoter.

Purification of HIV Protease. In some cases the protease was purified by reverse-phase HPLC, and the homogeneous proteins were then refolded as described by A. G. Tomasselli, et al., *Biochemistry* 29:264 (1990), and stored at −20° C.

In other cases, the protease was purified by ammonium sulfate precipitation, affinity chromatography on pepstatin-agarose (Sigma), followed by DEAE-Sepharose and, for HIV-1, S-Sepharose (Pharmacia). The bacterial cells were lysed with lysis buffer (50 mM Tris-HCl, pH 7.5; 10% v/v glycerol; 5 mM EDTA; 2mM PMSF) by resuspending cells in 6 volumes of lysis buffer at 4° C. for 3 hours. The mixture was sonicated twice for 15 minutes, then centrifuged for 1 hour (13,000 RPM in a Sorvall GSA). Aliquots were then mixed with 1% (on a weight basis of cells) of profamine sulfate (10% solution in water) and stirred for 15 minutes at room temperature. Stirring was then continued at 4° C. for 45 minutes, followed by centrifuging for 1 hour (42,000 RPM at 4°). The preparation was then mixed with 57.5% ammonium sulfate and stirred overnight (4° C.). Again the preparation was centrifuged (1 hour, 13,000 RPM in GSA at 4° C.). The resulting pellet was dissolved in 2 volumes of PAA Wash (50 mM HEPES, pH 7.5; 1 mM EDTA) and stirred for 1 hour (4° C.).

The material was then loaded onto a 15-mL column of pepstatin-agarose (equilibrated in PAA Wash; no salt) at a rate of 2 mL/minute. The column was then washed with PAA Wash (with 0.4M ammonium surfate), followed by a gradient wash (0.4M to 1M ammonium sulfate in PAA Wash). The column was then washed once more with PAA Wash (15 mL). The purified material was then eluted with PAA Elution Buffer (250 mM Na-ε-aminocaproate, pH 10.5; 5% glycerol (volume basis); 5% ethylene glycol (volume basis); 1 mM EDTA). The active elutions were pooled, the pH adjusted to 10.5 and the conductance adjusted to 1.8 mS. The sample was then loaded onto a 25-mL DEAE-Sepharose column (equilibrated in PAA Elution Buffer) at a rate of 1 mL/minute. The column was then washed with DEAE-Sepharose Wash Buffer (250 mM Na-ε-amino-caproate, pH 10.5; 1 mM EDTA) (50 mL). The protease was then eluted with PAA Wash (100 mL).

For HIV-2, adequate purification was achieved in this manner, as confirmed by the electrophoresis gel. For HIV-1, adequate purification was achieved by supplementing this procedure with an additional elution on S-Sepharose.

HIV-1 protease can also be purified by loading the processed cell lysates directly on DEAE-Sepharose followed by S-Sepharose chromatography and affinity chromatography on pepstatin-agarose (i.e., without ammonium sulfate precipitation). This has been found to give good purity and excellent yield.

Regardless of the manner in which the protease was purified, the active fractions were pooled and either lyophilized or frozen. These fractions served as stock protease for in vitro inhibition assays.

Enzyme Concentrations. The concentrations of the enzymes were established by titration with the substrate-based inhibitor Val-Ser-Gln-Asn-Leu-ψ[CH(OH)CH$_2$]-Val-Ile-Val. (SEQ ID No.: 3) Stock solutions of HIV-1 and HIV-2 proteases had specific activities on a decapeptide substrate of 23.9 μmol.min$^{-1}$.mg$^{-1}$ and 0.5 μmol.min$^{-1}$.mg$^{-1}$, respectively. Recombinant human renin had a specific activity of 400 Goldblatt units/mg.

Both HIV-1 and HIV-2 proteases were assayed against the decapeptide, Ala-Thr-Leu-Asn-Phe-Pro-Ile-Ser-Pro-Trp (SEQ ID No.: 1), corresponding to the HIV-1 C-terminal autoprocessing site (where underlined residues are cleavage sites). The decapeptide was synthesized by conventional solid-state methods. Reactions were carried out and fractionated by HPLC. Conversion of the decapeptide to the two pentapeptides was quantitated by integration of the peak areas and comparison to product standard curves.

Pepsin assay. Porcine pepsin from Sigma ($2 \times 10^{-3}$ mg/mL) with a specific activity of 0.38 μmol.min$^{-1}$.mg$^{-1}$, was incubated for 1 hour at 37° C. with various concentrations of Ala-Thr-Leu-Asn-Phe-Pro-Ile-Ser-Pro-Trp (SEQ ID No.: 1) in 0.1M sodium acetate (pH 4.7) containing 4 mm EDTA and 5% (vol/vol) dimethyl sulfoxide (DMSO). Pepsin also specifically cleaves the Phe-Pro peptide bond. Enzyme velocity was determined for 0.1 mL reaction volumes using HPLC.

Renin assay. Recombinant human renin (1 μg/mL) was assayed with 150 μM porcine angiotensinogen-(1–14) (Sigma) in 0.1 mL of 0.1M sodium phosphate (pH 6.1) containing 10 mM EDTA and 5% DMSO. After a 15-minute incubation at 37° C., the reaction was quenched. Hydrolysis products (Leu-Val-Tyr-Ser (SEQ ID No.: 4) and angiotensin I, Asp-Arg-Val-Tyr-Ile-His-Pro-Phe-His-Leu) (SEQ ID No.: 5) were separated using HPLC with the absorbance monitored at 220 nm. The peak area of angiotensin I was integrated and compared to a standard curve of human angiotensin I (Sigma).

Inhibitor assays. Stock solutions of compounds of this invention at 50 mM were prepared in 100% DMSO. Compounds were added to buffer solutions containing additional DMSO to give a final concentration of 5%. Control reaction mixtures contained 5% DMSO only. Enzymes were preincubated with inhibitor for 5 minutes at 25° C., followed by addition of substrate to initiate the reaction.

Enzymatic Inhibition. The effect of the compounds on HIV-1 protease hydrolytic activity was examined with various concentrations of the decapeptide substrate. Each data point was done in triplicate and initial enzyme rates were fit to the Michaelis-Menten equation using a nonlinear regression program ("Enzfitter" from Biosoft). Under the indicated assay conditions, the $K_m$ for the decapeptide substrate was $2.5 \pm 0.44$ mM, $V_{max}$ was $213.9 \pm 2.3$ μmol•min$^{-1}$•mg$^{-1}$, and $k_{cat}$ was 514 min$^{-1}$. The Dixon plot yielded a $K_i$ of $100 \pm 20$ μM. The appearance of the Dixon plot is comparable to that obtained with the transition state analogue, pepstatin, that inhibits HIV-1 protease in a partially noncompetitive fashion (data not shown). The HIV-2 enzyme exhibited a similar Dixon plot with a $K_i$ of ≈100 μM (data not shown).

The effect of the compounds on other aspartyl proteases was evaluated. The expected specificity of the compounds for the active site of the viral protease was confirmed by their inability to inhibit human renin at concentrations as high as 5 mM (data not shown). Pepsin was 55% inhibited by 1 mM UCSF 1.

Polyprotein Processing in Bacteria. *E. coli* strain D1210 harboring plasmid pSOD/PR179 (see above) was grown at 37° C. in Luria broth containing ampicillin (100 μg/mL). Cultures were grown to OD$_{650}$=0.4 at which time IPTG was added to a final concentration of 200 μM for induction and 5 mL samples of the cultures were removed. The compounds were dissolved in DMSO to 50 mg/mL. The appropriate volumes of these stock solutions were added within 5 minutes of induction to achieve a final concentration of 50 µM. The cultures were returned to the orbital shaker at 37° C. and 1 mL samples were collected at 15, 30, 60, and 120 minutes. The $OD_{650}$ Of each culture was determined and equivalent concentrations of cells (0.2 unit at $OD_{650}$) were pelleted by centrifugation. The cell pellets were resuspended in 30 µL of 1x Laemmli sample buffer, heated at 95° C. for 10 minutes, and passed repeatedly through a syringe needle to shear the chromosomal DNA, and the sample was clarified by centrifugation. The supernatant was then loaded onto a 12.5–17.5% gradient polyacrylamide gel containing SDS and subjected to electrophoresis. The gels were immunoblotted and probed with antibodies to the HIV-1 protease.

Gels and Immunoblotting. Gel electrophoresis was performed on either 15 or 17.5% SDS-polyacrylamide discontinuous gels. In most cases, protein samples were first precipitated by the addition of 1/10th volume of 100% (w/v) TCA containing 5 mg/mL sodium deoxycholate. After incubating for 1 hour at 0° C., the sample was centrifuged and the pellet was washed with cold acetone, re-centrifuged and dried in a Savant Speed-Vac. The proteins were redissolved in 10 mM Tris-HCl pH 7.5, sample buffer was added and, after heating for 5 minutes at 95° C., the samples were loaded on SDS-polyacrylamide gels. Proteins were visualized on acrylamide gels by either Coomassie blue or silver staining of the acrylamide gels. For immunoblotting, separated proteins were transferred electrophoretically to nitrocellulose paper (0.45 µm pore size, Schleicher and Schuell) in buffer containing 20% methanol, 150 mM glycine and 20 mM Tris-HCl, pH 8.3. The nitrocellulose sheets (blots) were incubated in PBS containing 0.1% Triton X-100 and 1% dry milk (Carnation) for 30 minutes. The blots were then incubated in antibody-containing sera (either rabbit polyclonal sera against the protease diluted 1:500, or pooled sera from patients diluted 1:200) diluted in blot buffer for 30 minutes. After three separate 5-minute washes in PBS with 0.1% Triton X-100, the blots were incubated with horseradish peroxidase anti-IgG antibodies (either goat anti-rabbit or goat anti-human) for 30 minutes. Following three separate 5-minute washes, color was developed by incubating the blots in a solution of hydrogen peroxide and 4-chloronaphthol in methanol. All the reactions were performed at 37° C. For references, a prestained marker mix, containing proteins ranging from 3 to 43 kD (Gibco-BRL), was run in parallel.

Rabbit polyclonal antibodies were raised against concentrated culture supernatant from yeast cells expressing and secreting an HIV-1 polypeptide encompassing the 78 C-terminal amino acids of the protease and the 37 N-terminal residues of the reverse transcriptase.

Cytotoxicity. The MTT assay was performed as follows:

The cells were seeded in 96-well plates and grown overnight to near 50% confluency. A serial dilution (1 to 500 µM) of each compound in culture media was prepared and 250 µL/well was added in duplicate. The cells were allowed to grow for various periods of time (6, 24, 48 hours) and any precipitation of compounds in the wells was noted. The assay was performed by removing 200 µL of the culture media and adding 25 µL of MTT solution (2 mg/mL in phosphate buffered saline (PBS)). This was incubated for 4 hours at 37° C. and live cells began to turn purple while the solution remained yellow. To quench the reaction and solubilize the reaction product, 160 µL of acidified isopropanol (4 mL 1N HCl for 96 mL alcohol) were added and the resulting mixture was mixed vigorously to dissolve purple crystals. Absorbance was determined at 550–570 nm on an ELISA plate reader within 0.5–2 hours. The average of the observed absorbantes versus the concentration of compound added was then plotted. To obtain the $LD_{50}$ values for each compound, the concentration at which the absorbance is haft of that for the untreated cells was determined.

Trypan blue exclusion was performed as follows:

A 1:1 dilution of commercially available 0.4% trypan blue with PBS was prepared. The resulting solution was mixed with an equal volume of the cell suspension to be tested. Since dead cells absorb the dye and turn blue, the white and blue cells were counted in a hemocytometer to determine the percentage of viable cells.

$^3$H-Thymidine incorporation was performed as follows:

The cells were grown in 96-well plates for the desired period of time in the presence or absence of the various compounds. Media containing 1 µCi/50 µL/well using $^3$H-thymidine of 20 Ci/mmol specific activity were then prepared. The media and label were then added to the cells and incubated at 37° C. for 4–6 hours. For adherent cells such as COS-7, the medium was removed, and the cells were washed with PBS and trypsinized. The cells were transfered to paper filter discs with a multichannel cell harvester, then rinsed with PBS and dried. The discs were transfered to vials and 1 mL of scintillation fluid was added. The full tritium range was counted and the average cpm for triplicate samples was determined.

EXAMPLE 1

The compound selected for preliminary tests was UCSF1 (see Table 1). Haloperidol differs from bromoperidol in that it bears a chlorine rather than a bromine substituent on one of the two phenyl rings. The small difference in the size of these two substituents (van der Waals radius: Cl, 1.8 Å; Br, 1.95 Å) is well within the tolerance limits of the search procedures.

Commercial haloperidol (Sigma) was recrystallized from diethyl ether/CHCl$_3$, 4:1 (volume basis), and the recrystallized material was shown to be pure by its melting point (mp 148.2°–149° C.; lit. 148.0°–149.4° C.) (29), by NMR, and by elemental analysis. The purified material was used for all biological work even though little difference was found between the recrystallized and commercial samples.

EXAMPLE 2

The hydroxy derivative of UCSF1 was obtained by reduction of haloperidol with lithium aluminum hydride in diethyl ether/tetrahydrofuran (3:1, volume basis) was crystallized from hexane/methylene chloride (4:1, volume basis) filtration through silica gel (mp 121°–122.5° C.). The $^1$H NMR, infrared, mass spectrum, and elemental analysis of the crystalline product are consistent with the assigned structure.

EXAMPLE 3

For the synthesis of 4-[4-(p-chlorophenyl)-4-hydroxy-N-oxopiperidinyl]-4'-fluorobutyrophenone (UCSF3), m-chloroperbenzoic acid (100 mg) was added to a cooled (ice bath), stirred solution of haloperidol (106 mg) in 10 mL dry (distilled from CaH$_2$) CH$_2$Cl$_2$. After 30 minutes, the reaction was filtered to remove a white precipitate. Evaporation of the solvent gave a white solid (105 mg) that was redissolved in a minimal amount of CH$_2$Cl$_2$ and refiltered to remove undissolved material. The N-oxide was thus obtained as a white solid (78 mg, 71% yield): $R_f$=0.00 in 100% ethyl acetate; mp 113.0°–119.0° C. (decompose). The identity of the product was confirmed as that of 4-[4-(p-chlorophenyl)-4-hydroxy-N-oxopiperidinyl]-4'-fluorobutyrophenone by IR, proton NMR, LSIMS and elemental analysis.

EXAMPLE 4

For the synthesis of 4-[4-(p-chlorophenyl)-4-hydroxypiperidinyl]-4'-fluorobutyrophenone oxime (UCSF4), hydroxylamine hydrochloride (35 mg) and solid $Na_2CO_3$ (35 mg) were added to a solution of haloperidol (52 mg) in 3 mL of methanol. The resulting mixture was stirred at room temperature for 3 days, at which point thin layer chromatography indicated the reaction was complete. Removal of the solvent at a rotary evaporator gave a solid residue. The residue was taken up in a minimal amount of $CH_2Cl_2$ and was purified by column chromatography on 3.5 g of silica gel with ethyl acetate as the eluting solvent. The oxime was obtained as a white solid (48 mg, 89% yield): $R_f=0.09$ in 100% ethyl acetate; mp 130.0°–131.0° C. The identity of the product was confirmed as that of 4-[4-(p-chlorophenyl)-4-hydroxypiperidinyl]-4'-fluorobutyrophenone oxime by IR, proton NMR, LSIMS and elemental analysis.

EXAMPLE 5

For the synthesis of 4-[4-(p-chlorophenyl)-4-hydroxy-N-methylpiperidinyl]-4'-fluorobutyrophenone (UCSF5), iodomethane (35 μL) was added to a solution of haloperidol (102 mg) in 5 mL absolute ethanol and 3 mL dry diethyl ether and the mixture was stirred at room temperature for 2 days. The solution was concentrated to dryness with rotary evaporation and the residue was washed with diethyl ether, giving 125 mg (84% yield) of white solid, $R_f=0.00$ in 100% ethyl acetate; mp 192°–194° C. (decompose). The identity of the product was confirmed as that of 4-[4-(p-chlorophenyl)-4-hydroxy-N-methylpiperidinyl]-4'-fluorobutyrophenone by IR, proton NMR, LSIMS and elemental analysis.

EXAMPLE 6

For the synthesis of 4-[4-(p-chlorophenyl)-4-acetoxypiperidinyl]-4'-fluorobutyrophenone (UCSF6), acetic anhydride (3 mL) and 4-dimethylaminopyridine (45 mg) were added to a suspension of haloperidol (100 mg) in 15 mL of $CH_2Cl_2$. The suspension became a clear solution after 15–30 minutes. The solution was stirred for a further 5 days. The mixture was then taken to dryness on a rotary evaporator and the residue was purified by silica gel chromatography (13 g silica gel, 25% ethyl acetate-hexane to 100% ethyl acetate), giving the acetate (100 mg) in 90% yield: $R_f=0.43$ in 100% ethyl acetate; mp 93.0°–96.0° C. The identity of the product was confirmed as that of 4-[4-(p-chlorophenyl)-4-acetoxypiperidinyl]-4'-fluorobutyrophenone by IR, proton NMR, EI and elemental analysis.

EXAMPLE 7

For the synthesis of 4-[4-(p-chlorophenyl)-4-hydroxypiperidinyl]-4'-fluorobutyrophenone hydrazone (UCSF7), hydrazine (100 μL) was added to a suspension of haloperidol (100 mg) in 15 mL of methanol followed by concentrated HCl (7 drops) and $Na_2CO_3$. The mixture was stirred at room temperature for 3 days before the solvent was removed under vacuum. The residue, taken up in a minimal amount of $CH_2Cl_2$, was purified by flash column chromatography on 4.3 g of silica gel with ethyl acetate as the eluting solvent. The hydrazone was obtained as a white solid (170 mg) in 81% yield: $R_f=0.07$ in 100% ethyl acetate; mp 151.0°–153.0° C. The identity of the product was confirmed as that of 4-[4-(p-chlorophenyl)-4-hydroxypiperidinyl]-4'-fluorobutyrophenone hydrazone by IR, proton NMR, EI and elemental analysis.

EXAMPLE 8

For the synthesis of (1,2-ethanethioacetal)-4-(4-(p-chlorophenyl)-4-hydroxypiperidinyl)-4'-fluorobutyrophenone (UCSF8), 500 μL of boron trifluoride etherate was added dropwise to a stirred suspension of haloperidol (200 mg) and 100 μL of 1,2-ethanedithiol in 10 mL of methanol. The clear solution was stirred at room temperature in a sealed flask for 2 days. The solution was poured into 30 mL of saturated aqueous $NaHCO_3$ and the mixture was extracted with 60 mL of diethyl ether. The ether layer was washed with 30 mL of saturated aqueous NaCl and was then dried over anhydrous sodium sulfate. Solvent removal gave an oil that was dissolved in a minimum amount of $CH_2Cl_2$ and purified by flash column chromatography on 6 g of silica gel. The column was eluted with 15% to 50% ethyl acetate in hexane. The thioketal was obtained as a white solid (240 mg) in 99% yield: $R_f=0.17$ in 50% ethyl acetate in hexanes; mp 101.0°–102.5° C. The identity of the product was confirmed as that of (1,2-ethanethioacetal)-4-(4-(p-chlorophenyl)-4-hydroxypiperidinyl[-4'-fluorobutyrophenone by IR, proton NMR, EI and elemental analysis.

EXAMPLE 9

For the synthesis of (1,3-propanethioacetal)-4-[4-(p-chlorophenyl)-4-hydroxypiperidinyl]-4'-fluorobutyrophenone (UCSF10), 750 μL of boron trifluoride etherate was added dropwise to a stirred suspension of haloperidol (300 mg) and 175 μL of 1,3-propanedithiol in 15 mL of methanol. The homogeneous solution was stirred at room temperature in a sealed flask for 2 days. The solution was then poured into 30 mL of saturated aqueous $NaHCO_3$ and the mixture was extracted with 60 mL of diethyl ether. The ether layer was washed with 30 mL of saturated aqueous NaCl, dried over anhydrous sodium sulfate, and concentrated under vacuum to an oil that solidified with time. This residue was dissolved in $CH_2Cl_2$ and was purified by flash chromatography (8 g silica gel, 25% to 50% ethyl acetate in hexane). The thioketal was obtained as a white solid (328 mg) in 88% yield: $R_f=0.48$ in 100% ethyl acetate; mp 112.0°–113.0° C. The identity of the product was confirmed as that of (1,3-propanethioacetal)-4-[4-(p-chlorophenyl)-4-hydroxypiperidinyl]-4'-fluorobutyrophenone by IR, proton NMR, EI and elemental analysis.

EXAMPLE 10

For the synthesis of 4-[4-(p-chlorophenyl)]-N-[4-(4'-fluorobutyrophenone)]-1,2,5,6-tetrahydropyridine (UCSF11), a solution of haloperidol (2.0 mmol) in 15 mL of acetic acid plus 8 mL of hydrochloric acid was refluxed for 3 hours. The cooled solution was poured in ice-water. This cold solution was then basified slowly by adding sodium hydroxide pellets. A precipitate formed which was washed with cold water. The white powder shows only one spot on TLC and was isolated in 98% yield. Part of this material was recrystallized from ether-hexane. The crude product and the recrystallized material have the same melting point (100°–101° C.). The identity of the product was confirmed as that of 4-[4-(p-chlorophenyl)-N-(4-(4'-fluorobutyrophenone)]-1,2,5,6-tetrahydropyridine by proton NMR, mass spectrometry, and elemental analysis.

EXAMPLE 11

For the synthesis of (trans-2,3-butanethioacetal)-4-[4-(p-chlorophenyl)-4-hydroxypiperidinyl]-4'-fluorobutyro-phenone (UCSF12), 1.7 mL of boron trifluoride etherate was added dropwise to a stirred suspension of haloperidol (300 mg) and 150 μL of 2,3-butanedithiol in 15 mL of methanol. The homogeneous solution was stirred at room temperature for 3 days and was then poured into 40 mL of saturated aqueous $NaHCO_3$. Extraction with 45 mL of diethyl ether gave an organic layer that was washed with 30 mL of saturated aqueous NaCl and dried over anhydrous sodium sulfate before the solvent was removed at a rotary evaporator. The residue, taken up in a minimal amount of $CH_2Cl_2$, was purified by flash chromatography on 10 g of silica gel (25% ethyl acetate). The less polar product (56 mg) was isolated pure in 15% yield: $R_f=0.53$ in 100% ethyl acetate; mp 108.5°–109.5° C. The identity of the product was confirmed as that of (trans-2,3-butanethioacetal)-4-[4-(p-chlorophenyl)-4-hydroxypiperidinyl]-4'-fluorobutyro-phenone by IR, proton NMR, EI, and elemental analysis,

EXAMPLE 12

For the synthesis of 4-[4-(p-chlorophenyl)-4-hydroxy-[N-(2-phenyl)ethyl]piperidinyl]-4'-fluorobutyrophenone (UCSF15), 2-bromoethylbenzene (800 μL) was added to 300 mg of haloperidol in 15 mL of methanol and 5 mL of THF. This mixture was refluxed under argon for 7 days. Removal of the solvent on a rotary evaporator gave a pink solid-liquid mixture that was stirred with 25 mL of $CH_2Cl_2$ for 4 hours. Filtration and thorough washing with $CH_2Cl_2$ gave a white solid (301 mg, 67% yield): mp 196°–199° C. The identity of the product was confirmed as that of 4-[4-(p-chlorophenyl)-4-hydroxy-[N-(2-phenyl)ethyl]piperidinyl]-4'-fluorobutyrophenone by IR, proton NMR and LSIMS.

EXAMPLE 13

For the synthesis of (1,2-ethyloxoacetal)-4-[4-(p-chlorophenyl)-4-hydroxypiperidinyl]-4'-fluorobutyrophenone (UCSF16), haloperidol (400 mg), pyridinium p-toluenesulfonate (300 mg), and ethylene glycol (2 mL) were refluxed in 60 mL of toluene under argon for 5 days. The mixture was diluted with 40 mL of diethyl ether and was washed first with saturated aqueous $NaHCO_3$ (40 mL) and then with saturated aqueous NaCl (30 mL). Solvent removal at a rotary evaporator gave 502 mg of a white solid that was recrystallized from diethyl ether. A white crystalline solid (342 mg, 76% yield) was thus obtained: $R_f=0.09$ in 100% ethyl acetate; mp 110°–120.5° C. The identity of the product was confirmed as that of (1,2-ethyloxoacetal)-4-(4-(p-chlorophenyl)-4-hydroxypiperidinyl]-4'-fluorobutyrophenone by IR, proton NMR, CI, and elemental analysis.

EXAMPLE 14

The compound identified above as UCSF17 was prepared from 4-[4-(p-chlorophenyl)]-N-[4-(4'-fluorobutyrophenone)]-1,2,5,6-tetrahydropyridine (UCSF11) by dissolving 250 mg (0.97 mmol) of the latter in 25 mL of THF and 6.0 mL of water, cooling the resulting solution to 5° C. in an ice-water bath, and slowly adding 178 mg (1.0 mmol) of N-bromosuccinamide with stirring. A yellow color developed in the solution, and the bath was removed. Stirring was allowed to continue overnight at room temperature. The solution was then concentrated, and a yellow precipitate formed. The precipitate was filtered, and water was added to the residual solution, which was then extracted first with ether and then with chloroform. The extracts were washed with brine and dried over sodium sulfate. The solvents were evaporated to form additional yellow crystals. The combined product weighed 160 mg (38% yield), mp 64°–65° C. Its identity was established as that of 4-[4-(p-chlorophenyl)]-N-[4-(4'-fluorobutyrophenone)]pyridinium bromide by proton NMR.

EXAMPLE 15

For the synthesis of (1,2-benzene-dimethanethioacetal)-4-[4-(p-chlorophenyl)-4-hydroxypiperidinyl]-4'-fluorobutyrophenone (UCSF18), 1 mL of boron triifluoride etherate was added dropwise to a stirred suspension of haloperidol (300 mg) and o-xylene-α,α'-dithiol (200 mg) in 10 mL of methanol. The clear solution was stirred at room temperature in a sealed flask for 4 days. The solution was poured into 30 mL of saturated aqueous $NaHCO_3$ and the mixture was extracted with 60 mL of diethyl ether. The ether was washed with 30 mL of saturated NaCl solution and was dried over anhydrous sodium sulfate. Removal of the solvent on a rotary evaporator gave a white solid that, dissolved in a minimum of $CH_2Cl_2$, was then purified by flash chromatography on 9.5 g of silica gel. The column was eluted with 25% to 50% ethyl acetate in hexane. The thioketal was obtained as a white solid (275 mg, 65% yield); $R_f=0.55$ in 100% ethyl acetate; mp 85°–88° C. The identity of the product was confirmed as that of (1,2-benzenedimethanethioacetal)-4-[4-(p-chlorophenyl)-4-hydroxypiperidinyl]-4'-fluorobutyrophenone by IR, proton NMR and CI.

EXAMPLE 16

For the synthesis of 4-(4-phenyl)-4- hydroxypiperidinyl)-4'-fluorobutyrophenone (UCSF19), a solution of 165 mg (0.5 mmol) of UCSF11 in 40 mL of methanol plus 64 mg of 10% palladium on charcoal was subjected to hydrogenation on a Parr apparatus for two hours at 25 psi. Purification by column chromatography on alumina (ethyl acetate:hexane 6:4) yielded a white powder, 126 mg (84% yield): mp 94°–96° C. The identity of the product was confirmed as that of 4-(4-phenyl)-4-hydroxypiperidinyl)-4'-fluorobutyrophenone by LSIMS, proton NMR and elemental analysis.

EXAMPLE 17

For the synthesis of 4-[4-(p-chlorophenyl)-3,4-dihydroxypiperidinyl]-4'-fluorobutyrophenone (UCSF20), 696 mg (1.95 mmol) of UCSF11 was added under nitrogen to 7 mL of dry pyridine. To this solution was added a solution of 0.5 g of $OsO_4$ in 5 mL of dry ether. After 3 hours of stirring at room temperature starting material was present according to TLC so the reaction was run overnight. The reaction mixture was then treated with a solution of 1 g of sodium bisulfite in 15 mL of water and 12 mL of pyridine and stirred for 2 hour. The color of the solution remained brownish it did not change to reddish, more sodium bisulfite was added (0.5 g) and further stirred for 2 hours. The resulting suspension was extracted with chloroform and the extract was washed with brine before the solvent was evaporated on a rotary evaporator. After the chloroform had evaporated, n-heptane was added to make an azeotrope with the pyridine. The precipitate which formed was isolated and a portion was purified by preparative TLC on silica gel. NMR analysis showed it to be the desired product. The rest of the material was purified by column chromatography on alumina and ethyl acetate:hexane 6:4 as elution system. The yield of purified material was 95 mg (12%) of a white powder with mp 106° C. The identity of the product was confirmed as that of 4-[4-(p-chlorophenyl)-3,4-dihydroxypiperidinyl]-4'-fluorobutyrophenone by LSIMS, proton NMR and elemental analysis.

EXAMPLE 18

The procedures for preparation and purification of (1,3-benzenedimethanethioacetal)-4-[4-(p-chlorophenyl)-4-hydroxypiperidinyl]-4'-fluorobutyrophenone (UCSF21) were the same as those for preparation of the o-xylyl isomer, except that m-xylene-α,α'-dithiol (200 μL) was used and the reaction was allowed to stir for 11 days. Flash chromatography of the oil that was obtained from the reaction mixture gave 104 mg of a waxy white solid (25% yield); $R_f$=0.55 in 100% ethyl acetate; mp 52°–56° C. The identity of the product was confirmed as that of (1,3-benzenedimethanethioacetal)-4-[4-(p-chlorophenyl)-4-hydroxypiperidinyl]-4'-fluorobutyrophenone by IR, proton NMR and LSIMS, and MS molecular weight determination.

EXAMPLE 19

The procedures for preparation and purification of (1,4-benzenedimethanethioacetal)-4-[4-(p-chlorophenyl)-4-hydroxypiperidinyl]-4'-fluorobutyrophenone (UCSF22) were as reported above for the m-xylyl isomer starting with p-xylene-α,α'-dithiol (199 mg). Flash chromatography of the solid that was obtained from the reaction mixture gave 62 mg of a waxy white material solid (15% yield); $R_f$=0.55 in 100% ethyl acetate; mp 65°–68° C. The identity of the product was confirmed as that of (1,4-benzenedimethanethioacetal)-4-[4-(p-chlorophenyl)-4-hydroxypiperidinyl]-4'-fluorobutyrophenone by IR, proton NMR, LSIMS, and MS molecular weight determination.

EXAMPLE 20

For the synthesis of (1,4-butanethioacetal)-4-[4-(p-chlorophenyl)-4-hydroxypiperidinyl]-4'-fluorobutyrophenone (UCSF23), 1 mL of boron trifluoride etherate was added dropwise to a stirred suspension of haloperidol (300 mg) and 1,4-butanedithiol (175 μl) in 10 mL of methanol. The clear solution was stirred at room temperature in a sealed flask for 5 days. The solution was poured into 30 mL of saturated aqueous NaHCO₃ and the mixture was extracted with 60 mL of diethyl ether, The ether was washed with 30 mL of saturated NaCl solution and was dried over anhydrous sodium sulfate. Removal of the solvent on a rotary evaporator gave a white solid that, dissolved in a minimum of $CH_2Cl_2$, was purified by flash chromatography on 9.8 g of silica gel. The column was eluted with 25% to 50% ethyl acetate in hexane. The thioketal was obtained as an oil and was resubmitted to silica gel chromatography. This gave 50 mg (13% yield) of an oil with a slight olefin contamination; $R_f$=0.49 in 100% ethyl acetate. The identity of the product was confirmed as that of (1,4-butanethioacetal)-4-[4-(p-chlorophenyl)-4-hydroxypipefidinyl]-4'-fiuorobutyrophenone by IR, proton NMR, LSIMS, and MS molecular weight determination.

EXAMPLE 21

For the synthesis of 4-[4-(p-chlorophenyl)-4-hydroxypiperidinyl]-1-[(phenylmethyl)-1-(p-fluorophenyl)-butan-1-ol (UCSF25), a 250 mg sample of haloperidol was dissolved in approximately 20 mL of THF. Five equivalents of benzyl magnesium bromide were added by syringe under an inert atmosphere while the solution was stirring over an ice-water bath. The reaction was slowly allowed to reach room temperature. The reaction was continued for several hours. The extent of reaction was determined by TLC on fluorescent silica gel plates (Artaltech) using ethyl acetate as the eluent. After the reaction was complete, quenching of the excess reagent was accomplished by transferring the mixture to a beaker containing ice-water. The products were extracted into ether and evaporated to dryness. The crude product (light yellow solid) was purified by column chromatography with a pentane-$CH_2Cl_2$-ethyl acetate gradient as eluent. The product was then recrystallized from hexane to yield 210 mg (68% yield) of a white solid with a melting point of 77°–79° C. The identity of the product was confirmed as that of 4-[4-(p-chlorophenyl)-4-hydroxypiperidinyl]-1-[(phenylmethyl]-1-(p-fluorophenyl)-butan-1-ol by IR, proton NMR, and MS molecular weight determination.

EXAMPLE 22

The procedures for preparation and purification of 4-[4-(p-chlorophenyl)-4-hydroxypiperidinyl]-1-phenyl-1-(p-fluorophenyl)-butan-1-ol (UCSF24) were as described for UCSF25 except the reaction was run with phenyl lithium instead of benzyl magnesium bromide. Purification of the crude product by column chromatography with subsequent recrystallization in hexane resulted in a white powder with a melting point of 69°–71° C. The overall yield for the reaction was 73% (220 mg of product were obtained). The identity of the product was confirmed as that of 4-[4-(p-chlorophenyl)-4-hydroxypiperidinyl]-1-phenyl-1-(p-fluorophenyl)-butan-1-ol by IR, proton NMR, and MS molecular weight determination.

EXAMPLE 23

For the synthesis of 4-[4-(p-chlorophenyl)-α-(2-azanaphthyl)-4-hydroxy-1-piperidinylbutan-1-ol (UCSF27), cyclopropyl isoquinolinyl ketone (2.98 g) was dissolved in xylenes (20 mL). 4-Hydroxy-4-phenylpiperidine (6.5 g) was added, along with $K_2CO_3$ (100 mg) and refluxed under argon for four days. The mixture was cooled to room temperature. Ether was added, and the resulting mixture was washed with saturated NaHCO₃(aq) followed by saturated NaCl(aq). The aqueous phases were extracted with ether. These ether layers were combined, then dried over $Na_2SO_4$, and evaporated to a brown oil (7.25 g). This material was dissolved in a minimum of $CH_2CH_2$, and purified on silica-gel column (53.8 g) eluted with a gradient system (25% ethyl acetate in hexanes to 100% ethyl acetate). UCSF27 was obtained in 3.085 g and was recrystallized from $CH_2Cl_2$ hexanes to give 2.55 g of purified material: $R_f$=0.30 in 100% ethyl acetate; mp 89°–91° C. The identity of the product was confirmed as that of 4-[4-(p-chlorophenyl)-α-(2-aza-naphthyl)-4-hydroxy-1-piperidinylbutan-1-ol by IR, proton NMR and CI.

EXAMPLE 24

For the synthesis of (1,2-ethyloxoacetal)-4-(4-phenyl-4-hydroxypiperidinyl)-4'-fluorobutyrophenone (UCSF28), 2-(3-chloropropyl)-2-(4-fluorophenyl)-1,3-dioxolane (600 mg) was added into a flask containing 4-hydroxy-4-phenylpiperidine (1 g) and xylenes (5 mL). This mixture was vigorously refluxed under argon for two days. The mixture was cooled to room temperature. Ether (30 mL) was added, and this mixture was washed with saturated NaCl (30 mL). The aqueous was extracted with ether (30 mL). The ether layers were combined, then dried over Na$_2$SO$_4$, and evaporated to a brown oil (1.466 g). This material was dissolved in a minimum of CH$_2$Cl$_2$, and purified on a silica-gel column (24 g), eluted with a gradient system (25% ethyl acetate in hexanes to 100% ethyl acetate). The UCSF28 (850 mg) thus obtained was recrystallized from CH$_2$Cl$_2$/hexanes/ether to give 54.7 mg of product: R$_f$=0.16 in 100% ethyl acetate; mp 111.0°–111.5° C. The identity of the product was continued as that of (1,2-ethyloxoacetal)-4-(4-phenyl-4-hydroxypiperidinyl)-4'-fluorobutyrophenone by IR, proton NMR, CI and elemental analysis.

EXAMPLE 25

For the synthesis of 4-(4'-phenylbutyl)-1-phenyl-1,4-cyclohexanediol (UCSF29), the precursor 4-(4'-phenylbutyl)-4-hydroxycyclohexanone was made by mixing 103.1 mg (4.3 mmol) of Mg turnings, 15 mL of ether and 1 g (4.7 mmol) of 4-phenylbromobutane in a dry flask under nitrogen and adding 3 drops of 1,2-dibromoethane to initiate the reaction. The reaction was maintained under gentle reflux until all the magnesium was consumed (1 hour) before a solution of 650 mg (4.1 mmol) of ketalcyclohexanone in 10 mL of ether was added while cooling in an ice water bath. After the addition the cooling bath was removed and the reaction was stirred at room temperature. Work-up was done by pouring the reaction mixture to a mixture of water-ice, which was then extracted with ether. The ether was then washed with water and brine. The organic solution was dried over sodium sulfate and evaporated to yield a crude product which shows several spots on TLC. The crude product (1.1 g) was dissolved in 15 mL of acetone, 0.5 mL of water and 201 mg (0.8 mmol) of pyridinium-p-toluenesulfonate, and the resulting mixture was refluxed for 1 hour. The solvent was then evaporated, ether was added to the residue, and the ether solution was washed with 5% sodium bicarbonate, water and brine. Drying over sodium sulfate and solvent evaporation gave a syrupy residue which crystallized upon standing. Recrystallization from ether-hexane yielded 303 mg (29% yield) of white crystals: mp 64°–66° C. The identity of the product was continued as that of 4-(4'-phenylbutyl)-4-hydroxycyclohexanone by IR, proton NMR and EI.

The 4-(4'-phenylbutyl)-4-hydroxycyclohexanone (240 mg, 0.97 mmol) was dissolved in 15 mL of dry THF under nitrogen. The solution was cooled down to 0° C. (ice-water bath) and 1.4 mL (2.5 mmol) of 1.8M phenyllithium was added slowly to maintain the temperature 0°–5° C. After addition the reaction mixture was maintained at 0° C. for 30 minutes. The bath was then removed and stirring was continued. After 1 hour, no starting material was detected by TLC. The reaction mixture was poured onto a mixture of ice-water (80 mL) and extracted with ether (three 50-mL portions). The organic phase was washed with brine and dried over sodium sulfate. Evaporation of the solvent left a residue that was purified by flash chromatography on silica gel with ethyl acetate:hexane 1:1 as the eluting solvent, yielding 201 mg (64%) of a viscous clear liquid. The identity of the product was confirmed as that of 4-(4'-phenylbutyl)-1-phenyl-1,4-cyclohexanediol by IR, proton NMR and LREI.

EXAMPLE 26

For the synthesis of (1,2-ethyloxoacetal)-4-(4-phenyl-4-hydroxypipeddinyl)butyrophenone (UCSF30), 2-(3-chloropropyl)-1-phenyl-1,3-dioxolane (600 mg) was added with the 4-hydroxy-4-phenylpiperidine (1.2 g) in a 50 mL round bottom flask. Xylenes (20 mL) were added, and this mixture was vigorously refluxed under argon for 3 days. The mixture was cooled to room temperature. Ether (30 mL) was added, and this mixture was washed with saturated NaHCO$_3$ (30 mL) and NaCl (30 mL). The aqueous layers were extracted with ether (30 mL). The ether layers were combined, then dried over Na$_2$SO$_4$, and evaporated to a brown oil (1.31 g). This material was dissolved in a minimum of CH$_2$Cl$_2$, and purified on silica-gel column (16 g) with a gradient system (25% ethyl acetate in hexanes to 100% ethyl acetate). The desired UCSF30 was obtained (600.1 mg). A portion was recrystallized from CH$_2$Cl$_2$/hexanes to give a pure sample of UCSF30; R$_f$0.13 in 100% ethyl acetate; mp 101.5°–103.5° C. The identity of the product was confirmed as that of (1,2-ethyloxoacetal)-4-(4-phenyl-4-hydroxypiperidinyl)butyrophenone by IR, proton NMR, CI and elemental analysis.

EXAMPLE 27

For the synthesis of 4-(4-phenyl-4-hydroxypiperidinyl)-4'-fluorobutyrophenone (UCSF31), UCSF28 (795.5 mg) was dissolved in a methanol (20 mL) and acetone (20 mL) mixture. Then p-toluenesulfonic acid (528 mg) was added. Stirring continued in a sealed flask for 2 days (during which, some precipitate had formed). The reaction was poured into saturated NaHCO$_3$ (30 mL), and this mixture was extracted with ether (20 mL). This ether layer was washed with saturated NaCl (30 mL). The aqueous layers were extracted with ether (20 mL), followed by CH$_2$Cl$_2$. The organic layers were combined, then dried over Na$_2$SO$_2$, and evaporated to give a tan solid (636.3 mg). This material was dissolved in a minimum of CH$_2$Cl$_2$, and filtered through a silica-gel column (1 g) with ethyl acetate and CH$_2$CH$_2$. This material was then recrystallized from CH$_2$Cl$_2$/hexanes to give 538 mg of UCSF31; R$_f$=0.11 in 100% ethyl acetate; mp 134.0°–135.0° C. The identity of the product was confirmed as that of 4-(4-phenyl-4-hydroxypiperidinyl)-4'-fluorobutyrophenone by IR, proton NMR, CI and elemental analysis.

EXAMPLE 28

For the synthesis of 4-(4-phenyl-4-hydroxypiperidinyl)-1-phenyl-1-[α-(2-azanaphthyl)]-butan-1-ol (UCSF32), a 250 mg sample of UCSF27 was reacted with phenyl lithium under conditions analogous to those described above. The product was purified by column chromatography and recrystallized from hexane to yield a white solid with mp 64°–66° C. The identity of the product was confirmed as that of 4-(4-phenyl-4-hydroxypiperidinyl)-1-phenyl-1-[α-(2-azanaphthyl)]-butan-1-ol by IR, proton NMR and MS molecular weight determination.

EXAMPLE 29

For the synthesis of 4-[4-(p-chlorophenyl)-4-hydroxypiperidinyl)-1-phenyl-1-(p-phenylphenyl)-butan-1-ol (UCSF33), phenyl diol p-biphenyl haldol was obtained from the reaction of 100 mg (0.23 mmol) of non-recrystallized UCSF36 with phenyl lithium. The starting material was dissolved in about 20 mL of THF. Phenyl lithium (3.5 eq) was added by syringe under an inert atmosphere while the solution was stirring over an ice-water bath. The reaction was allowed to reach room temperature and stirring was continued for two hours. TLC showed complete disappearance of starting material and a product spot with an R$_f$ of 0.67 in 10% methanol in ethyl acetate. The reaction was stopped by its addition to a beaker of ice-water. The product was extracted into ether, dried over sodium sulfate, filtered, and evaporated to dryness. The product was purified by flash chromatography using a gradient from 100% CH$_2$Cl$_2$ to 100% ethyl acetate as eluent to yield a yellow solid. This crude product was recrystallized from hexane to yield a white powder (70 mg, overall yield 59%). The identity of the purified product was confirmed as that of 4-[4-(p-chlorophenyl)-4-hydroxypiperidinyl]-1-phenyl-1-(p-phenylphenyl)-butan-1-ol by IR, proton NMR and CI.

EXAMPLE 30

For the synthesis of 4-(4-phenyl-4-hydroxypiperidinyl)butyrophenone (UCSF34), UCSF30 (505 mg) was dissolved in a mixture of 10 mL of methanol and 10 mL of acetone. Then p-toluenesulfonic acid (302 mg) was added. Stirring continued in a sealed flask for 2 days. The reaction was poured into saturated NaHCO$_3$ (30 mL), and this mixture was extracted with ether (20 mL). This ether layer was washed with saturated NaCl (30 mL). The aqueous layers were extracted with ether (20 mL), followed by CH$_2$Cl$_2$ (20 mL). The organic layers were combined, then dried over Na$_2$SO$_4$, and evaporated to a tan solid. This material was dissolved in a minimum of CH$_2$Cl$_2$, and purified on silica-gel column (6.5 g) with a gradient system (25% ethyl acetate in hexanes to 75% ethyl acetate) to yield 415 mg of product. A portion was recrystallized from CH$_2$Cl$_2$/hexanes to give a pure sample; R$_f$=0.13 in 100% ethyl acetate; mp 128.0°–130.0° C. The identity of the product was confirmed as that of 4-(4-phenyl-4-hydroxypiperidinyl)butyrophenone by IR, proton NMR, CI and elemental analysis.

EXAMPLE 31

For the synthesis of 4-(4-chlorophenyl-α-(4-pyridyl)-4-hydroxy-1-piperidinylbutan-1-ol (UCSF35), p-pyridinyl cyclopropyl ketone (1.48 g) was dissolved in xylenes (5 mL). 4-(4-Chlorophenyl)-4-hydroxypiperidine (4.3 g) was then added, and the mixture was refluxed under argon for three days. A small amount of K$_2$CO$_3$ and additional 4-(4-chlorophenyl)4-hydroxypiperidine (400 mg) were then added, and refluxing was continued for 4 days more. The product mixture was extracted with ether (60 mL) and CH$_2$Cl$_2$ (10 mL), washed with saturated NaCl, then extracted with an ether-CH$_2$Cl$_2$ mixture (80 mL) to give a brown oil (4.92 g). This material was dissolved in a minimum of CH$_2$Cl$_2$, and purified on silica-gel column (30 g) with a gradient system (50% ethyl acetate in hexanes to 100% ethyl acetate to 25% methanol in ethyl acetate). The desired compound, obtained in 1.0 g, was recrystallized from CH$_2$Cl$_2$/hexanes to give 590.6 mg; R$_f$=0.09 in 100% ethyl acetate, 0.18 in 10% methanol in ethyl acetate; mp 96°–99° C. The identity of the product was confirmed as that of 4-(4-chlorophenyl-α-(4-pyridyl)-4-hydroxy-1-piperidinylbutan-1-ol by IR, proton NMR and CI.

EXAMPLE 32

For the synthesis of 4-[4-(p-chlorophenyl)-4-hydroxypiperidinyl]-4'-phenylbutyrophenone (UCSF36), 2 g (a slight excess) of 4-(4 chlorophenyl)-4-hydroxy pipeddine was added by pipet as a suspension in xylene to 1.8 g (8.11 mmol) of p-biphenyl cyclopropyl ketone in approximately 50 mL of xylene. The reaction mixture was heated to reflux for 3 days. The mixture was then cooled to room temperature and a yellow precipitate formed. A portion of the precipitate was recrystallized from methylene chloride to yield about 70 mg of colorless needles identified by IR, proton NMR and CI as 4-[4-(p-chlorophenyD-4hydroxypiperidinyl]-4'-phenylbutyrophenone, with a melting point of 166°–167° C. (decomposed).

EXAMPLE 33

For the synthesis of 1-[4-(4-chlorophenyl)-4-hydroxypipefidinyl]-4-(4-fluorophenyl)-4-pentene (UCSF37), (methyl)triphenylphosphonium bromide (2.3 g) was added to THF (35 mL). The mixture was cooled in a dry ice/ethanol bath under argon before n-butyllithium (in hexanes, 2.5M, 2.8 mL) was slowly added into the reaction flask. Stirring was continued at room temperature for 3 hours to ensure all the butyllithium reacted. This solution was again cooled. Haloperidol (1 g) dissolved in THF (5 mL) was added slowly into the reaction flask. Stirring continued at room temperature for two days, during which time the color went from pale yellow to white. The reaction was quenched by the addition of water (75 mL) and diluted with diethyl ether (75 mL). The layers were partitioned, and the ether layer was washed with saturated NaCl solution. The ether layer was dried over Na$_2$SO$_4$, and evaporated to a golden brown oil (2.22 g). This material was dissolved in a minimum of CH$_2$Cl$_2$, and purified on a silica-gel column (55 g) and eluted with a gradient system (20% ethyl acetate in hexanes to 100% ethyl acetate). The desired compound was obtained pure in 179.5 mg: R$_f$=0.26 in 100% ethyl acetate; mp 103.5°–104.5° C. The identity of the product was confirmed as that of 1-[4-(4-chlorophenyl)-4-hydroxypiperidinyl]-4-(4-fluorophenyl)-4-pentene by IR, proton NMR and LSIMS.

EXAMPLE 34

For the synthesis of 5-[4-(4-chlorophenyl)-4-hydroxypiperidinyl]-2-(4-fluorophenyl)pentan-2-ol-1-methylsulfide (UCSF39), a solution of trimethylsulfonium iodide (2.2 g) in THF (45 mL) was cooled in a dry ice/ethanol bath under argon. Methyllithium (in ether, about 1.4M, 10 mL) was slowly added into the reaction flask. Stirring continued at room temperature for 3 hours total to ensure all methyllithium reacted. The solution was again cooled in the bath, and a white precipitate began to form. The solution was allowed to warm back to room temp, and went back to a yellow cloudy solution, much more cloudy than before. Haloperidol (1.05 g) dissolved in THF (10 mL) was added slowly into the reaction flask. The solution was stirred at room temperature for 15 minutes. The reaction was quenched by the addition of water (60 mL) and diluted with diethyl ether (10 mL). The layers were partitioned, and the ether layer was washed with saturated NaCl (60 mL). The aqueous layers were back-extracted with diethyl ether (60 mL), then with THF (60 mL). The ether layers were combined, dried over Na$_2$SO$_4$, and evaporated oil (1.779 g). The material was dissolved in a minimum of CH$_2$Cl$_2$, and purified on a silica-gel column (45 g), eluted with a gradient system (25% ethyl acetate in hexanes to 100% ethyl acetate). The compound was isolated as a solid (550.0 mg): R$_f$=0.27 in 100% ethyl acetate; mp 54°–56° C. The identity of the product was confirmed as that of 5-[4-(4-chlorophenyl)-4hydroxypiperidinyl]-2-(4-fluorophenyl)pentan-2-ol-1-methylsulfide by IR, proton NMR and

EXAMPLE 35

For the synthesis of 6-[4-(4-chlorophenyl)-4-hydroxypiperidinyl]-3-(4-fluorophenyl)hex-1-en-3-ol (UCSF40), UCSF39 and trimethylsulfonium iodide (2.6 g) were added into THF (45 mL). The mixture was cooled in a dry ice/ethanol bath under argon before methyllithium (in ether, about 1.4M, 18 mL) was slowly added into the reaction flask. Stirring continued at room temperature for 3 hours to ensure all methyllithium had reacted (and the solution went from clear and colorless to yellow). This solution was again cooled in the bath. Haloperidol (1.5 g), dissolved in THF (10 mL), was added slowly into the reaction flask. Stirring continued at room temperature for three days (during which the color went from pale yellow to opaque white). The reaction was quenched by the addition of water (75 mL) and diluted with diethyl ether (75 mL). The layers were partitioned, and the ether layer was washed with saturated NaCl (75 mL). The aqueous layers were back-extracted with diethyl ether (75 mL). The ether layers were combined, dried over $Na_2SO_4$, and evaporated to a golden oil (1.67 g). This material was dissolved in a minimum of $CH_2Cl_2$, and purified on a silica-gel column (51 g), eluted with a gradient system (10% ethyl acetate in hexanes to 100% ethyl acetate). Both UCSF39 (259.3 mg) and UCSF40 (524.3 mg) were isolated. The latter, an oil, had $R_f=0.39$ in 100% ethyl acetate. The identity of the product was confirmed as that of 6-[4-(4-chlorophenyl)-4hydroxypiperidinyl]-3-(4-fluorophenyl)hex-1-en-3-ol by proton NMR and EI.

EXAMPLE 36

For the synthesis of 4-(4'-phenyl-4-pentenyl)-1-(p-chlorophenyl)-1,4-cyclohexanediol (UCSF41), 93 mg of Mg turnings (3.8 mmol) and 700 mg (3.8 mmol) of 5-chloro-2-phenylpentene were added to 10 mL of dry THF. A crystal of iodine was added and no reaction was observed. 1,2-Dibromoethane (0.01 mL) was then added and the reaction mixture was heated with a water bath at 40° C. to initiate the reaction. The water bath was then removed and the reaction was permitted to continue at room temperature overnight, by which time all Mg had been consumed. A solution of 546 mg (3.5 mmol) of 4-ketalcyclohexanone in 10 mL of THF was then added, and the suspension was stirred for 4 hours at room temperature. Product recovery was performed in the same manner as in the preceding example. Flash chromatography on silica gel eluting with ethyl acetate:hexane 2:8 yielded 122 mg (13.5%) of a clear syrup-like liquid. The identity of the product was confirmed as that of 4-(4'-phenyl-4'-pentenyl)-4-hydrox-cyclohexanone by IR, proton NMR and EI.

A solution of 100 mg (0.38 mmol) of the 4-(4'-phenyl-4'-pentenyl)-4-hydroxcyclohexanone obtained above was treated with 0.80 mL (0.80 mmol) of chlorophenyl magnesium bromide 1M at 0° C. The solution was then stirred for 1.5 hours at 25° C. and worked up as described previously for Grignard additions to yield 74 mg (52%) after purification by flash chromatography on silica gel with hexane:ethyl acetate 6:4. Confirming analyses by LREI, IR, and proton NMR established the identity of the product as 4-(4'-phenyl-4-pentenyl)-1-(p-chlorophenyl)-1,4-cyclohexanediol.

EXAMPLE 37

For the synthesis of 1-[4-(4-chlorophenyl-4-hydroxy-N-oxo-piperidinyl]-4-(4-fluorophenyl)-4-pentene (UCSF42), UCSF37 (221 mg) and $H_2O_2$ (500 µL) in methanol (10 mL) and $CH_2Cl_2$ (10 mL) were stirred in a sealed flask for two weeks. The solvent was evaporated and $CH_2Cl_2$ was added. The resulting mixture was stirred for several hours, then filtered to yield a white solid (185 mg total, 80% yield). Proton NMR assignments were verified with decoupling studies to confirm the structure of the product as that of UCSF42: $R_f=0.00$ in 100% ethyl acetate; mp 176°–180° C. (decomposed, browning at approximately 170° C.). The identity of the product was confirmed as that of 1-[4-(4-chlorophenyl-4-hydroxy-N-oxo-piperidinyl]-4-(4-fluorophenyl)-4-pentene by IR, proton NMR and LSIMS.

EXAMPLE 38

This example describes the synthesis of both 4-[4-(p-chlorophenyl)-4-hydroxypiperidinyl]-3-phenyl-4'-methylbutyrophenone (UCSF43) and 4-[4-(p-chlorophenyl)-4-hydroxypiperidinyl]-4-phenyl-4'-methylbutyrophenone (UCSF44).

In a 50 mL round bottom flask, trans-1-(4-methylbenzyl)-2-phenyl-cyclopropane (729 mg, 3.09 mmol, with $R_f=0.62$ in 25% ethyl acetate, from the Alfred Bader Rare Chemical Library) and 4-(4-chlorophenyl)-4-hydroxypiperidine (1.15 g, 5.44 mmol, 1.8 eq) were refluxed in xylenes (5 mL) under argon for 5 days. The mixture was cooled to room temperature. Ether was added; the resulting brown mixture was filtered. The eluate was washed with saturated NaCl (50 mL). The aqueous layers were extracted with ether (30 mL). The ether layers were combined, then dried over $Na_2SO_4$, and evaporated to a brown oil (1.886 g). This material was dissolved in a minimum of $CH_2Cl_2$, and purified on silica-gel column (41.8 g) with a gradient system (5% ethyl acetate to 75% ethyl acetate). Two compounds were isolated in a total amount of 1.054 g (76% yield) in a ratio of 1 to 8.

The identity of the first compound (111.6 mg), $R_f=0.22$ in 25% ethyl acetate, 0.75 in 100% ethyl acetate, mp 116°–118° C., was confirmed as that of 4-[4-(p-chlorophenyl)-4-hydroxyl-peridinyl]-3-phenyl-4'-methylbutyrophenone by IR, proton NMR, $^{13}C$ NMR and LSMIS.

The identity of the second compound (812.9 mg), $R_f=0.14$ in 25% ethyl acetate, 0.44 in 50% ethyl acetate, 0.68 in 100% ethyl acetate, mp 144°–145° C., was similarly confirmed as that of 4-[4-(p-chlorophenyl)-4-hydroxypipedinyl]-4-phenyl-4'-methylbutyrophenone by IR, proton NMR, $^{13}C$ NMR and LSMIS.

EXAMPLE 39

For the synthesis of 2-[4-(4-chlorophenyl)-4-hydroxypiperidinyl]-(N,N-dibenzyl)ethylamine (UCSF46), N-(2-chloroethyl)dibenzylamine hydrochloride (860 mg, 2 eq, $R_f=0.84$ in 100% ethyl acetate for the free base) and 4-(4-chlorophenyl)-4-hydroxypiperidine (300 mg, $R_f=0.00$ in 100% ethyl acetate) with $Na_2CO_3$ (600 mg) in a 50 mL round bottom flask, were combined with 5 mL of xylenes under argon and held at room temperature for 1.5 hours to neutralize the acid, then refluxed for two days. The mixture was cooled to room temperature. Ether was added (50 mL). The ether was washed with saturated $NaHCO_3$ (60 mL), then with saturated NaCl (60 mL). The aqueous layers were extracted with ether (40 mL). The ether layers were combined, then dried over $Na_2SO_4$, and evaporated to a brown oil (1.44 g). This material was dissolved in a minimum of $CH_2Cl_2$, and purified on silica-gel column (29 g) with a gradient system (10% ethyl acetate in hexanes to 100% ethyl acetate). The product was isolated in 80% yield; 557.3 mg: $R_f=0.15$ in 50% ethyl acetate, 0.37 in 100% ethyl acetate; mp 120.0°–121.0° C. The identity of the product was confirmed as that of 2-[4-(4-chlorophenyl)-4-hydroxypiperidinyl]-(N,N-dibenzyl)ethylamine by IR, proton NMR and LSIMS.

EXAMPLE 40

For the synthesis of (3-[4-(4-chlorophenyl)-4-hydroxypiperidinyl)-1-propyl)triphenylsilane (UCSF47), a reaction mixture was prepared in a 50 mL round bottom flask containing (3-bromopropyl)-triphenylsilane (258.4 mg, from A. Bader Rare Chemical Library, $R_f$=0.72 in 50% ethyl acetate)and 4-(4-chlorophenyl)-4-hydroxypiperidine (288.1 mm, 2 eq, $R_f$=0.00 in 100% ethyl acetate) with $Na_2CO_3$ (600 mg, to neutralize the formation of the acid produced). This was stirred with warming in xylenes (5 mL) under argon for one day. The mixture was cooled to room temperature. Ether (30 mL) was added. The ether was washed with saturated $NaHCO_3$ (30 mL), then with saturated NaCl (30 mL). The aqueous layers were back-extracted with ether (20 mL). The ether layers were combined, then dried over $Na_2SO_4$, and evaporated to a whitish solid (800 mg). This material was dissolved in a minimum of $CH_2Cl_2$, and purified on a silica-gel column (13.4 g) with a gradient system (5% ethyl acetate in hexanes to 100% ethyl acetate), resulting in a white solid (138.6 mg, 68% yield), $R_f$=0.26 in 50% ethyl acetate, 0.52 in 100% ethyl acetate; mp 137.0°–138.5° C. The identity of the product was confirmed as that of (3-[4-(4-chlorophenyl)-4-hydroxypiperidinyl)-1-propyl)triphenylsilane by IR, proton NMR and LSIMS.

EXAMPLE 41

For the synthesis of (1,2-ethanethioacetal)-4-[4-(p-chlorophenyl-4-hydroxypipefidinyl]-4-phenyl-4'-methylbutyrophenone (UCSF48), 700 μL of boron trifluoride etherate was added dropwise to a stirred solution of UCSF44 (317.7 mg) and 120 μL of 1,2-ethanedithiol in 10 mL of methanol and 10 mL of $CH_2Cl_2$ chilled in an ice bath. The ice bath was removed, and the solution was stirred at room temperature in a sealed flask for one day. The solution was poured into 40 mL of saturated aqueous $NaHCO_3$ and the mixture was extracted with 40 mL of diethyl ether. The ether layer was washed with 30 mL of saturated aqueous NaCl. The aqueous layers were back-extracted with ether (20 mL). The ether layers were combined, then dried over anhydrous sodium surfate. Solvent removal gave a brown oil that was dissolved in a minimum amount of $CH_2Cl_2$ and purified by flash column chromatography on 16 g of silica gel. The column was eluted with a gradient of 5% to 100% ethyl acetate in hexanes. The thioketal was obtained (185.8 mg) in 52% yield (and recovered starting material in 15%): $R_f$=0.67 in 5% ethyl acetate. The identity of the product was confirmed as that of (1,2-ethanethioacetal)-4-[4-(p-chlorophenyl)-4-hydroxypipefidinyl]-4-phenyl-4'-methylbutyrophenone by IR, proton NMR and LSIMS.

EXAMPLE 42

For the synthesis of 4-[4-(p-fluorophenyl)-4-hydroxypiperidinyl]-2-methyl-4'-fluorobutyrophenone (UCSF50), butyl lithium (900 μL of a 2.5M hexanes solution) was slowly added into a mixture of diisopropyl amine (300 μL in THF (15 mL) cooled to 78° C. This mixture was stirred at room temperature for 15 minutes, then recooled to −78° C. A solution of haloperidol (360 mg) in THF (5 mL) was slowly added to the chilled solution, and stirred for 20 minutes. Methyl iodide (60 μL) was added. The dry ice/acetone bath was removed, and the resulting solution was stirred at room temperature for one hour. Water (50 mL) was added to quench the reaction. This solution was extracted with ether (40 mL), and the ether phase was washed with saturated NaCl (50 mL). The ether layers were combined, then dried over $Na_2SO_4$, and evaporated to give a white solid (937 mg). This material was purified on a silica-gel column (13.6 g) with a gradient system (25% ethyl acetate in hexanes to 100% ethyl acetate). The product was isolated as a solid in 43% yield, 160.8 mg, $R_f$=0.21 in 100% ethyl acetate, mp 115.0°–116.0° C. The identity of the product was confirmed as that of 4-[4-(p-fluorophenyl)-4hydroxypiperidinyl]-2-methyl-4'-fluorobutyrophenone by IR, proton NMR and LSIMS.

EXAMPLE 43

This example describes the synthesis of both 4-(4-(p-chlorophenyl)-4-hydroxypiperidinyl)-2'-phenylbutyrophenone (UCSF51) and 4-(4-(p-chlorophenyl)-4-hydroxypiperidinyl)-3'-phenylbutyrophenone (UCSF52). The ortho and meta biphenyl analogs of halopeddol were prepared from the opening of the cyclopropyl ring of the corresponding biphenyl cyclopropyl ketone (875 mg of the ortho isomer and 500 mg of the meta isomer) by 4-(4 chlorophenyl)4-hydroxy pipeddine by refluxing the two reagents in xylene for 5 days. The reaction was worked up as described for the synthesis of para-biphenyl haloperidol. The products were separated by flash chromatography using a slow gradient from 100% $CH_2Cl_2$ to 100% ethyl acetate to 10% methanol in ethyl acetate as eluent. Pooling of the fractions containing product followed by evaporation of the solvent resulted in an orange liquid for the ortho isomer, and a tan solid for the meta. In ethyl acetate, the $R_f$'s are 0.17 for o-biphenyl haldol, UCSF51, and 0.26 for the meta derivative, UCSF52. Both products were recrystallized from hexane yielding approximately 200 mg (12% yield), and 350 mg (35% yield), of the ortho and meta isomers respectively. A melting point of 96°–97° C. was determined for 4-(4-(p-chlorophenyl)-4-hydroxypiperidinyl)-2'-phenylbutyrophenone, and a melting point of 99°–100° C. was determined for 4-(4-(p-chlorophenyl)-4-hydroxypiperidinyl)-3'-phenylbutyrophenone. Spectral data supported the assigned structures for both products.

EXAMPLE 44

For the synthesis of 3-[4-(4-chlorophenyl)-4-hydroxypiperidinyl]-N-(benzyl)propylamine (UCSF55), a reaction flask was charged with N-(2-chloropropyl)-benzylamine hydrochloride (530 mg, 1.3 eq), 4-(4-chlorophenyl)-4-hydroxypipeddine (420mg), triethylamine (0.5 mL) and $Na_2CO_3$ (1.2 g). Xylenes (5 mL) were stirred in over one hour under argon, and the mixture was refluxed for two days. The resulting brown mixture was then cooled to room temperature, and ether (50 mL) was added. The ether layer was washed with 5% $NaHCO_3$ (40 mL), then with saturated NaCl (45 mL). The aqueous layers were back-extracted with ether (20 mL). The ether layers were combined, then dried over $Na_2SO_4$, and evaporated to a brown oil (937 mg). The oil was purified on a silica-gel column (10.5 g) with a gradient system (50% ethyl acetate in hexanes to 100% ethyl acetate to 25% methanol in ethyl acetate) to give 285 mg (40% yield), $R_f$=0.10 in 100% methanol, 0.04 in 100% ethyl acetate. The identity of the product was confirmed as that of 3-[4-(4-chlorophenyl)-4-hydroxypiperidinyl]-N-(benzyl)propylamine by IR, proton NMR and LSIMS.

EXAMPLE 45

This example describes the synthesis of both 4-(4-(p-chlorophenyl)-4-hydroxypiperidinyl-1-phenyl-1-(2'-phenylphenyl)-butan-1-ol (UCSF56) and 4-(4-(p-chlorophenyl)-4-hydroxypiperidinyl)-1-phenyl-1-(3'-phenylphenyl)- butane 1-ol (UCSF57). The ortho- and meta-isomers of phenyl diol biphenyl haldol were obtained from the reaction of phenyl lithium with UCSF51 and UCSF52 (of Example 43) respectively in a manner analogous to that described in for the formation of UCSF33 (Example 29) above. Recrystallization from hexane of both products gave white powders. The ortho reaction proceeded with 56% yield (75 mg of starting material were used), whereas 80 mg of the meta product were obtained from 110 mg of starting material (61% yield). In ethyl acetate, $R_f$'s of 0.49 and 0.52 were obtained for 4-(4-(p-chlorophenyl)-4-hydroxypipeddinyl)-1-phenyl-1-(2'-phenylphenyl)-butan-1-ol and 4-(4-(p-chlorophenyl)-4-hydroxypiperidinyl)-1-phenyl-1-(3'-phenylphenyl)-butan-1-ol, respectively. Spectral analyses confirmed the structures of the products as those indicated above.

EXAMPLE 46

For the synthesis of 2-[4-(4-chlorophenyl)-4-hydroxypipefidinyl]-N-benzyl-N-(2-methoxy-ethyl)ethylamine (UCSF58), a reaction flask was charged with N-(2-chloroethyl)-N-(2-methoxyethyl)-benzylamine hydrochloride (403 mg, 1.53 mmol), 4-(4-chlorophenyl)-4-hydroxypiperidine (400 mg) and $Na_2CO_3$ (450 mg). Xylenes (10 mL) were refluxed in under argon over two days. The mixture was then cooled to room temperature and diluted with ether (50 mL). The ether dilution was washed with 5% $NaHCO_3$ (50 mL), followed by saturated NaCl (50 mL). The aqueous layers were back-extracted with ether (20 mL). The ether layers were combined, then dried over $Na_2SO_4$, and evaporated to a brown oil (639.1 mg). This material was purified on a silicagel column (16.2 g) with a gradient system (50% ethyl acetate in hexanes to 100% ethyl acetate to 75% methanol in ethyl acetate), resulting in an oil, 140 mg (23% yield), $R_f$=0.04 in 100% ethyl acetate, 0.24 in 100% methanol. The identity of the product was confirmed as that of 2-[4-(4-chlorophenyl)-4-hydroxypiperidinyl]-N-benzyl-N-(2-methoxyethyl)ethylamine by IR, proton NMR and LSIMS.

EXAMPLE 47

For the synthesis of (1,2-ethanedithioacetal)-4-(4-(p-chlorophenyl)-4-hydroxypiperidinyl)-4'-phenylbutyrophenone (UCSF59), 500 µL of $BF_3.OEt_2$ were added dropwise to 150 mg (0.346 mmol) of m-biphenyl haldol and 100 µL of ethane dithiol (1.2 mmol) in dry methanol. The solution was allowed to stir for 2 days. Quenching was accomplished by transferring the reaction mixture into saturated $NaHCO_3$ followed by extraction into ether. The ether layer was washed with saturated NaCl. The aqueous layers were combined and re-extracted with ether. The combined ether layers were dried over $Na_2SO_4$, filtered, and evaporated to dryness. The products were separated by flash chromatography using a slow gradient from 100% $CH_2Cl_2$ to 100% ethyl acetate as eluento The product was purified to a yellow solid, and spectral analyses confirmed its structure as that of (1,2-ethanedithioacetal)-4-(4-(p-chlorophenyl)-4-hydmxypiperidinyl)-4'-phenylbutyrophenone.

EXAMPLE 48

For the synthesis of 3-[4-(4-chlorophenyl)-4-hydroxypiperidinyl]-N-benzyl-N-(2-phenyl-ethyl)-propylamine (UCSF61), a reaction flask was charged with N-(2-chloropropyl)-N-(2-phenylethyl)benzylamine (125 mg, 0.411 mmol), 4-(4-chlorophenyl)-4-hydroxypiperidine (120 mg, 0.561 mmol) and $Na_2CO_3$ (110 mg). Xylenes (6 mL) were refluxed in under argon over two days. The resulting mixture was cooled to room temperature, then diluted with ether (30 mL). The ether layer was washed with saturated $NaHCO_3$ (30 mL) followed by saturated NaCl (30 mL). The aqueous layers were back-extracted with ether (30 mL). The ether layers were combined, then dried over $Na_2SO_4$, and evaporated to a brown oil (240 mg). This material was purified on a silica-gel column (6.2 g) with a gradient system (50% ethyl acetate in hexanes to 100% ethyl acetate), to yield 171 mg of an oil (89% yield), $R_f$=0.11 in 100% ethyl acetate. The identity of the product was continued as that of 3-[4-(4-chlorophenyl)-4-hydroxypiperidinyl]-N-benzyl-N-(2-phenyl-ethyl)-propylamine by proton NMR.

EXAMPLE 49

For the synthesis of 3-(4-(4-chlorophenyl)-4-hydroxypiperidinyl))-N-benzyl-N-((4-phenyl)-benzyl)propylamine (UCSF63), a reaction flask was charged with N-(methyl-p-biphenyl)-N-(2-chloropropyl)benzylamine (255 mg, 0.729 mmol), 4-(4-chlorophenyl)-4-hydroxypiperidine (302 mg, 1.412 mmol) and $Na_2CO_3$ (195 mg). The mixture was refluxed in xylenes (6 mL) under argon for two days, then cooled to room temperature and diluted with ether (50 mL). The ether layer was washed with saturated $NaHCO_3$ (50 mL) followed by saturated NaCl (50 mL). The aqueous layers were back-extracted with ether (40 mL). The ether layers were combined, then dried over $Na_2SO_4$, and evaporated to give a brown oil (513 mg). The oil was purified on a silica-gel column (14.9 g) with a gradient system (25% ethyl acetate in hexanes to 100% ethyl acetate), to yield 275 mg of an oil (72% yield), $R_f$=0.23 in 100% ethyl acetate. The identity of the product was confirmed as that of 3-(4-(4-chlorophenyl)-4-hydroxypipefidinyl))-N-benzyl-N-((4-phenyl)-benzyl)propylamine by proton NMR.

EXAMPLE 50

For the synthesis of 4-(4'-p-fluorophenyl-4'-butanone)-1-p-chlorophenyl-1,4-cyclohexanediol (UCSF65), the Grignard reagent was prepared from 1.16 g (4.75 mmol) of 4-(4'-fluorophenyl)-3-ethyleneketal-1-chlorobutane with Mg turnings (14.25 mmol), 0.1 mL of 1,2-dibromoethane in 20 mL of THF at room temperature as described previously, and allowed to react with 740 mg (407 mmol) of 4-ketalcyclo-hexanone. The crude material after work up was further treated with acetone and pyridinium-p-toluene-sulphonate. Purification by flash chromatography on silica gel and hexane:ethyl acetate 6:4 eluting system produced a product which crystallized. Recrystallization from ether-pentane produced 100 mg (7.5% yield) of white crystals: mp 88°–90° C. The identity of the product was confirmed as that of 4-(4'-p-fluorophenyl-4'-butanone)-4-hydroxy cyclohexanone by IR, proton NMR and EI.

A 93 mg sample of the 4-(4'-p-fluorophenyl-4'-butanone)-4-hydroxy cyclohexanone was treated with 1.65 mL (1.65 mmol) of chlorophenyl magnesium bromide under conditions described above. After purification, the desired product (12 mg) was isolated as a viscous liquid. Spectral analyses confirmed the structure of the product as that of 4-(4'-p-fluorophenyl-4'-butanone)-1-p-chlorophenyl-1,4-cyclohexanediol.

EXAMPLE 51

The synthesis of the epoxide derivative, N-benzyl-4-hydroxy-4-(3,4-epoxy-3-phenyl-1-butyny)piperidine (UCSF 70) was begun with the synthesis of the intermediate N-benzyl-4-ethynyl-4-piperidinol. Lithium acetylide diethylamine complex (1.84 g, 1.8 eq) was suspended in dry THF and the mixture cooled to 0° C. under argon. N-Benzyl-4-piperidinone (1.89 g, 10 mmol) was dissolved in dry THF (5 mL) and added dropwise to the stirred reaction mixture. After stirring overnight the reaction was quenched with saturated ammonium chloride solution (30 mL) and the aqueous was extracted with ethyl acetate (3×100 mL). The combined organic extracts were dried (MgSO$_4$) and evaporated under reduced pressure. Crude NMR indicated approximately 50–60% product, the remaining material being the starting piperidinone. The crude material was purified by flash column chromatography (SiO$_2$, 40–60% ethyl acetate/hexane) to give an oil. The identity of the oil was confirmed as that of the intermediate N-benzyl-4-ethynyl-4-piperidinol by proton NMR and $^{13}$C NMR.

The intermediate (109 mg, 0.506 mmol) was dissolved in dry THF (5 mL) and lithium hexamethyldisilazide (1.012 mL 1M THF solution, 2 eq) was added dropwise to the stirred solution under argon at 0° C. After one hour phenacyl bromide (101 mg, 0.506 mmol) was added and the reaction was allowed to warm to room temperature overnight. It was quenched with saturated ammonium chloride (20 mL) and the aqueous was extracted with ethyl acetate (2×20 mL). The combined organic extracts were dried and evaporated to yield an oil. This was purified initially by flash column chromatography (SiO$_2$, 60% ethyl acetate/hexane) to give the product (105 mg, 62%) contaminated with a small amount of the starting material. The product was further purified by flash column chromatography (SiO$_2$, 3% methanol/dichloromethane) to give pure product, the structure of which was confirmed as that of N-benzyl-4-hydroxy-4-(3,4-epoxy-3-phenyl-1-butynyl by proton NMR and CI.

EXAMPLE 52

The synthesis of the compound identified in Table 1 as UCSF71 was performed using 8-benzyl-6-hydroxymethyl-1,4-dioxa-8-azaspiro[4,5]decane (whose preparation is described by Nagai, et al., *Chem. Pharm. Bull.* 25:1911–1922 (1977)) as the starting material. This starting material was dissolved in dioxane (20 mL), aqueous hydrochloric acid (6N, 10 mL) and acetone (1 mL), and the solution was refluxed overnight. The reaction mixture was then cooled to room temperature, quenched with saturated aqueous sodium bicarbonate, and extracted with ethyl acetate in three portions of 20 mL each. The combined organic extracts were dried over magnesium surfate and evaporated in vacuo. The residue was purified by flash column chromatography (silica gel, 90% ethyl acetate/hexane) to give 144 mg of a solid product (27% yield). The structure of the compound was confirmed as that of UCSF71 by MS, proton NMR and $^{13}$C NMR.

EXAMPLE 53

The synthesis of 4-(4-chlorophenyl)-4-hydroxy-N-(3,4-epoxy-3-phenyl-1-butynyl)piperidine (UCSF84) was begun with the synthesis of the intermediate N-propargyl-4-(4'-chlorophenyl)-4-piperidinol. 4'-Chlorophenyl-4-piperidinol (840 mg, 3.97 mmol) was dissolved in xylene (5 mL) and propargyl bromide (450 μL 80% solution in toluene, 1 eq) was added and the solution stirred at room temperature overnight. The reaction mixture was then filtered through a plug of silica gel which was then washed thoroughly with ethyl acetate (200 mL). Evaporation of the solvent under reduced pressure yielded a pale yellow solid (423 mg, 42.7%), whose identity was confirmed as that of N-propargyl-4-(4'-chlorophenyl)-4-piperidinol by proton NMR and $^{13}$C NMR.

N-Propargyl-4-(4'-chlorophenyl)-4-piperidinol (95 mg, 0.38 mmol) was dissolved in dry THF (4 mL) and cooled to 0° C. under argon. Lithium hexamethyldisilazide (0.84 mL 1M THF solution, 2.2 eq) was added dropwise and the solution stirred at 0° C. for 15 minutes. It was then transferred via cannula to a suspension of cerium trichloride (200 mg, 0.8 mmol) in THF (4 mL) at −78° C. under argon. (This suspension had previously been stirred at room temperature for 1 hour.) After stirring the mixture for 1 hour at −78° C., phenacyl bromide (112 mg, 1.5 eq) was added and the reaction allowed to warm to room temperature. After 4 hours the reaction was quenched with saturated ammonium chloride solution and the aqueous was extracted with ethyl acetate (3×20 mL). The combined organic extracts were dried and evaporated to yield an oil. This was dissolved in methanol and potassium carbonate (140 mg, 1 mmol) was added and the mixture stirred at room temperature for 4 hours. The solvent was then removed under reduced pressure and the residue partitioned between ethyl acetate (20 mL) and brine (20 mL). The organic layer was separated, dried and evaporated to give an oil which was purified by flash column chromatography (SiO$_2$, 60% ethyl acetate/hexane) to give the product plus an equimolar amount of the starting alkyne. The identity of the product was confirmed as that of 4-(4-chlorophenyl)-4-hydroxy-N-(3,4-epoxy-3-phenyl-1-butyny)piperidine by proton NMR.

EXAMPLE 54

The synthesis of 4-(4'-(4"-chlorophenyl)-4'-hydroxypiperidinyl)-1-phenylbut-2-yn-1-one (UCSF86) was performed as follows.

Lithium hexamethyl disilazide (2 mL, 1.0M in THF, 2 mmol) was added dropwise at 0° C. under argon to a solution of N-propargylpiperidine (250 mg, 1 mmol) in dry THF (5 mL). After stirring the reaction mixture at 0° C. for 10 minutes, a solution of N-methoxy-N-methylbenzamide (164 mg, 1.05 mmol) in THF (3 mL) was added. Stirring was continued for 2 hours as the solution was allowed to warm to room temperature. The reaction was then quenched with saturated ammonium chloride solution (10 mL) and diluted with ethyl acetate (30 mL). The organic layer was separated, washed with brine (20 mL), dried, and concentrated under vacuum to give 4"-(4'-(4"-chlorophenyl)-4'-hydroxypiperidinyl)-1-phenylbut-2-yn-1-one as a solid (363 mg, 102%). The material was further purified by flash column chromatography (SiO$_2$, 70% ethyl acetate/hexane) and recrystallized from dichloromethane/ether/hexane for analysis: mp 138°–139° C. The identity of the product was confirmed as that of 4-(4'-(4"-chlorophenyl)-4'-hydroxypiperidinyl)-1-phenylbut-2-yn-1-one by IR, proton NMR, $^{13}$C NMR, and elemental analysis, with mass spectrometric determination of the molecular weight.

EXAMPLE 55

The synthesis of 4-(4'-(4""-chlorophenyl)-4'-hydroxypiperidinyl)-1-m-biphenylbut-2-ynol-one (UCSF142) was performed as follows.

Lithium hexamethyldisilazide (1.52 mL, 1.0M in THF, 1.52 mmol) was added dropwise under argon at 0° C. to a solution of N-propargylpiperidine (188 mg, 0.76 mmol) in dry THF (5 mL). After stirring the reaction mixture for 10 min at 0° C., a solution of amide (182 mg, 0.76 mmol) in THF was added. Stirring was continued for 2 hours as the solution was allowed to warm to room temperature. The reaction was quenched with saturated ammonium chloride solution (10 mL) and was then diluted with ethyl acetate (30 ml). The organic layer was separated, washed with brine (20 mL), dried, and concentrated. The residue was purified by flash column chromatography (SiO$_2$, 40% ethyl acetate/hexane) to give 4-(4'-(4''-chlorophenyl)-4'-hydroxypiperidinyl)-1-m-biphenylbut-2-yn-1-one as a solid (146 mg, 45%) that was recrystallized from dichloromethane/ether/hexane for analysis: mp 130.5°–131.5° C. (decomp.). The identity of the product was confirmed as that of 4-(4'-(4''-chlorophenyl-4'-hydroxypiperidinyl)-1-m-biphenylbut-2-yn-1-one by IR, proton NMR, $^{13}$C NMR, and elemental analysis, with mass spectrometric determination of the molecular weight.

EXAMPLE 56

The synthesis of 4-(4'-(4''-chlorophenyl)-4'-hydroxypiperidinyl)-1-p-biphenylbut-2-yn-1-one (UCSF231) was performed as follows.

The intermediate N-methoxy-N-methyl-p-biphenylcarboxamide was first formed. Pyridine (4 mL, 5 equivalents) and N,O-dimethylhydroxylamine hydrochloride (980 mg, 10 mmol) were added to a solution of p-biphenylcarbonyl chloride (2.16 g, 10 mmol) in dry dichloromethane (10 mL). The solution was stirred for 2 hours at room temperature and then diluted with ethyl acetate (20 mL), washed sequentially with 1N HCl (2×20 mL), saturated sodium bicarbonate (20 mL), and brine (20 mL). It was then dried over magnesium surfate and evaporated under reduced pressure to give N-methoxy-N-methyl-p-biphenylcarboxamide as a solid (1.78 g, 74%). The solid was recrystallized from ethyl acetate/hexane for analysis: mp 77°–78° C. The identity of the solid was confirmed as that of N-methoxy-N-methyl-p-biphenylcarboxamide by IR, proton NMR, $^{13}$C NMR and elemental analysis, with mass spectrometric determination of the molecular weight.

N-propargylpiperidine (252 mg, 1 mmol) was dissolved in dry THF (10 mL) at room temperature under argon and lithium hexamethyldisilazide (2.5 mL, 1.0M in THF, 2.5 mmol) was added dropwise. After stirring the reaction mixture for 20 minutes, N-methoxy-N-methyl-p-biphenylcarboxamide (410 mg, 1.7 mmol) was added. The solution was then heated at reflux for 1 hour. After cooling to room temperature, the reaction was quenched with saturated ammonium chloride solution (10 mL) and diluted with ethyl acetate (30 mL). The organic layer was separated, washed with brine (20 mL), dried, and evaporated to dryness. The residue was purified by flash column chromatography (SiO$_2$, 2% isopropanol/dichloromethane). The fractions containing product were rechromatographed (SiO$_2$, 40% ethyl acetate/hexane) to give 4-(4'-(4-chlorophenyl)-4'-hydroxypiperidinyl)-1-p-biphenylbut-2-yn-1-one as a solid (285 mg, 66%). The solid was recrystallized from dichloromethane/hexane for analysis: mp 168°–169° C. (decomp.). The identity of the product was confirmed as that of 4-(4'-(4''-chlorophenyl)-4'-hydroxypiperidinyl)-1-p-biphenylbut-2-yn-1-one by IR, proton NMR, $^{13}$C NMR and elemental analysis.

EXAMPLE 57

The synthesis of 4-(4'-(4''-chlorophenyl)-4'-hydroxy-1-oxo-piperidinyl)-1-phenylbut-2-en-1-one (UCSF115) was performed as follows, through the intermediate 4-(4'-(4''-chlorophenyl)-4'-hydroxypiperidinyl)-1-phenyl-2-phenylselenylbutan-1-one.

Lithium hexamethyldisilazide (1M, 0.665 mmol) was added at −78° C. to a solution of haloperidol (100 mg, 0.266 mmol) in THF (5 mL) and the mixture was stirred at room temperature for 2 hours before it was cooled to −78° C. and a solution of phenylselenyl chloride (57.5 mg, 0.3 mmol) in THF (3 mL) was added. The reaction mixture was stirred at room temperature for 2 hours and then poured into water and extracted with ethyl acetate. The extract was dried over magnesium sulfate. 4-(4'-(4''-Chlorophenyl)-4'-hydroxy-1-oxo-piperidinyl)-1-phenylbut-2-en-1-one was obtained as a colorless oil (101 mg, 73.5%) by column chromatography (silica gel, ethyl acetate). The identity of the oil was confirmed as that of the intermediate 4-(4'-(4''-chlorophenyl)-4'-hydroxypiperidinyl)-1-phenyl-2-phenylselenylbutan-1-one by proton NMR, $^{13}$C NMR and CI.

Hydrogen peroxide (30%, 0.15 mL, approximately 1.3 mmol) was added to a solution of the intermediate (85 mg, 0.164 mmol in THF (1.5 mL) and acetic acid (60 mL) at 0° C. The mixture was stirred at 0° C. for 2 hr and then at 25° C. for 2 hours before saturated sodium bicarbonate was added. The precipitate that formed was collected by filtration and dried under vacuum. 4-(4'-(4''-Chlorophenyl)-4'-hydroxy-1-oxo-piperidinyl)-1-phenylbut-2-en-1-one was thus obtained as a white solid (42 mg, 65.7%): mp 135° C. (decomp.). The identity of the product was confirmed as that of 4-(4'-(4''-chlorophenyl)-4'-hydroxy-1-oxo-piperidinyl)-1-phenylbut-2-en-1-one by IR, proton NMR, $^{13}$C NMR, CI, LSIMS, and elemental analysis.

EXAMPLE 58

The synthesis of 4-(4'-(4''-chlorophenyl)-4'-hydroxypiperidinyl)-1-phenylbut-2-en-1-one (UCSF191) was performed as follows, again using 4-(4'-(4''-chlorophenyl)-4'-hydroxypiperidinyl)-1-phenyl-2-phenylselenylbutan-1-one as an intermediate.

meta-Chloroperbenzoic acid (19 mg, 80–90%, approximately 0.1 mmol) was added at 0° C. to a solution of the intermediate (52 mg, 0.1 mmol) in dichloromethane (4 mL). The solution was stirred at this temperature for 6 hours, before aqueous sodium bicarbonate and 10 mL of CH$_2$Cl$_2$ were added and the organic phase was separated and dried over MgSO$_4$. After solvent removal, the residue was purified by column chromatography (silica gel, ethyl acetate/hexane=7/3) to yield a colorless oil (16 mg, 42.8%). The identity of the product was confirmed as that of 4-(4'-(4''-chlorophenyl)-4'-hydroxypiperidinyl)-1-phenylbut-2-en-1-one by IR, proton NMR, $^{13}$C NMR and EI, with MS determination of the molecular weight.

EXAMPLE 59

The synthesis of 4-(4'-(4''-chlorophenyl)-4'-hydroxypiperidinyl)-3-(2'-hydroxyethylthio)- 1-phenyl-2-buten-1-one (UCSF178) was performed as follows.

The acetylenic ketone 4-(4'-(4''-chlorophenyl)-4'-hydroxypiperidinyl)-1-phenylbut-2-yn-1-one (UCSF86) (50 mg, 0.14 mmol) was dissolved in methanol (1 mL) with β-mercaptoethanol (10 mL, 0.14 mmol) and the reaction was stirred overnight at room temperature. The mixture was then concentrated to dryness and the residue purified by flash column chromatography (SiO$_2$, 60% ethyl acetate/hexane) to give (39 mg, 63.9%) as a pale yellow solid which was recrystallized from dichloromethane/ether/hexane for analysis as 4-(4'-(4''-chlorophenyl)-4'-hydroxypiperidinyl)-3-(2'-hydroxyethylthio)-1-phenyl-2-buten-1-one: mp 122.5°–123.5° C. The identity of the product was confirmed as that of 4-(4'-(4"-chlorophenyl)-4'-hydroxypiperidinyl)-3-(2'-hydroxyethylthio)-1-phenyl-2-buten-1-one by IR, proton NMR, $^{13}$C NMR, EI, and elemental analysis.

EXAMPLE 60

In this example, HIV-1 protease was assayed against the decapeptide, Ala-Thr-Leu-Asn-Phe-Pro-Ile-Ser-Pro-Trp (SEQ ID No.: 1), corresponding to the HIV-1 C-terminal autoprocessing site (where the underlined residues are the cleavage site). The decapeptide was synthesized by conventional solid-state methods. Reactions were carried out in 0.1 mL 50 mM sodium acetate buffer, pH 5.5, containing 5 mM DTr, 1 mM EDTA, 5% DMSO, 250 mM peptide substrate, and varying concentrations of NaCl (1M, 0.5M, or 0.2M). HIV-1 protease ($2\times10^{-5}$ mg/mL for a final concentration of approximately 10 nM) was added to initiate the reaction in assay buffer containing 1M NaCl. The reaction was stopped after 1 hour at 37° C. by addition of 50 mL cold 1% trifluoroacetic acid in 50% acetonitrile on ice. Under these assay conditions, the $K_M$ for the decapeptide substrate is 2.5 mM (±0.44), $V_{max}$ is 23.9 mmol/min/mg (±) and $k_{cat}$ is 514 min$^{-1}$ Conditions were adjusted so that 25% of the substrate was hydrolyzed during the incubation. Based on the hydrolysis rate of HIV-1 protease in 1M NaCl buffer, the enzyme activity is reduced to 66% in the presence of 0.5 NaCl and 25% in the presence of 0.2M NaCl. In order to get the desired amount of substrate hydrolysis under the low salt conditions, the enzyme concentration was doubled and/or the incubation times were increased. Reaction products were separated by reverse-phase HPLC using a Pecosphere 0.46× 3.3 cm $C_{18}$ column (Perkin Elmer) with a gradient of 10–50% acetonitrile in 0.1% TFA. Samples were applied by means of a Rainin Al-1 autosampler. Absorbance was monitored at 280 nm during the 8.5 minute program. Conversion of the decapeptide to two penta-peptides was quantitated by integration of the peak areas and comparison to product standard curves.

Figure 2:
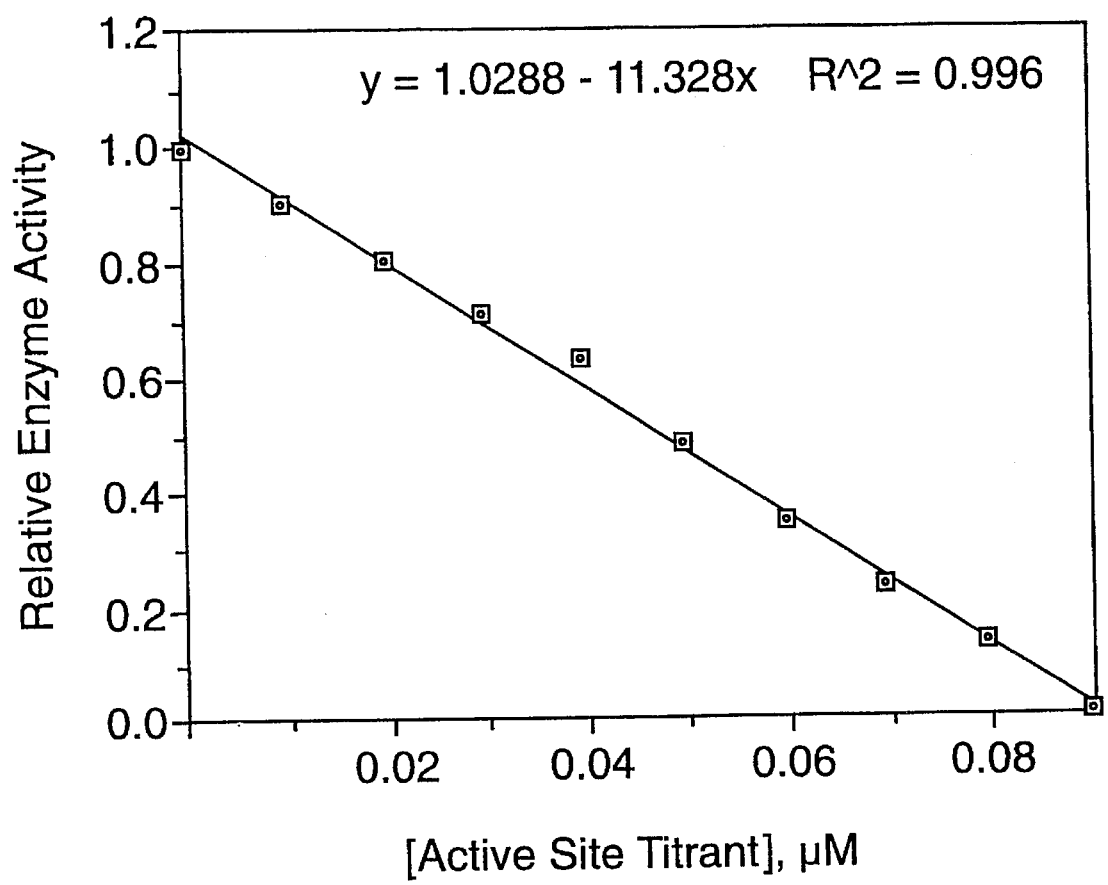
FIG. 2 is a graph showing the active site titration of HIV-1 protease using a decapeptide substrate.

FIG. 2 is a graph showing the active site titration of HIV-1 protease using the decapeptide substrate. The X-intercept= [HIV-1 protease]=0.091 µM. Since the enzyme was diluted 1:50 in the assay, the concentration of the stock enzyme was 4.5 µM. This corresponds to a concentration of 0.098 mg/mL (HIV-1 protease MW is 21,582 g/mole).

EXAMPLE 61

This example describes a determination of the sensitivity of an HIV-1 protease inhibition assay as a function of salt concentration. The enzyme and substrate were prepared as described above. A stock solution of UCSF 1 (haloperidol) at 20 mM was prepared in DMSO. Compound was added to buffer solutions containing additional DMSO to give a final concentration of 5%. Control reaction mixtures contained 5% DMSO only. Enzymes were preincubated with inhibitor for 5 minutes at 25° C., followed by addition of substrate to initiate the reaction.

Figure 3:
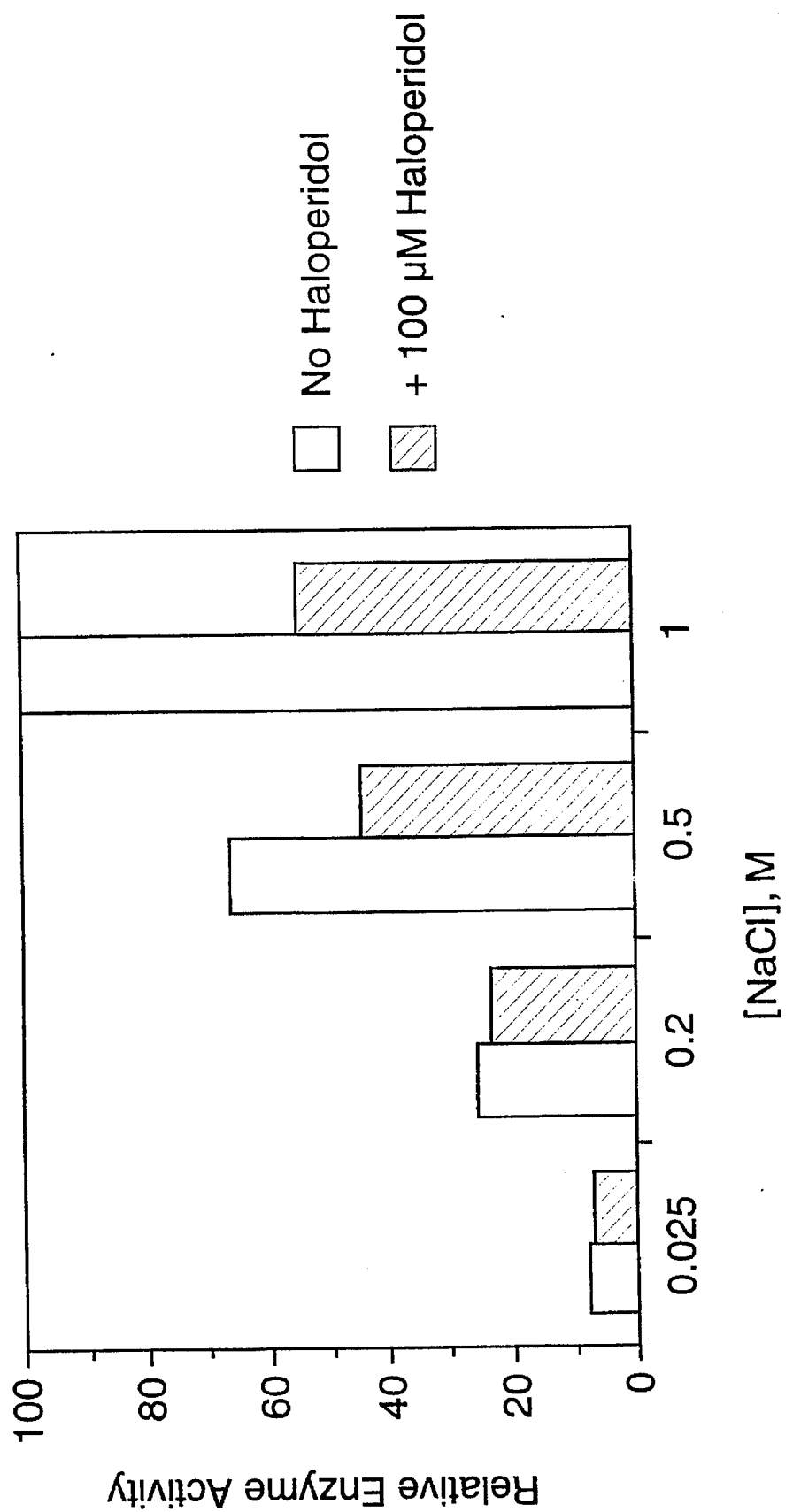
FIG. 3 is a bar graph showing the sensitivity of an HIV-1 protease inhibition assay as a function of salt concentration.

FIG. 3 is a bar graph showing the results of the assay under four different salt concentrations in the presence of 100 µM UCSF 1. The sensitivity of the inhibition assay increased with the salt concentration. At 1M NaCl, UCSF 1 inhibited the protease approximately 50%.

Figure 4:
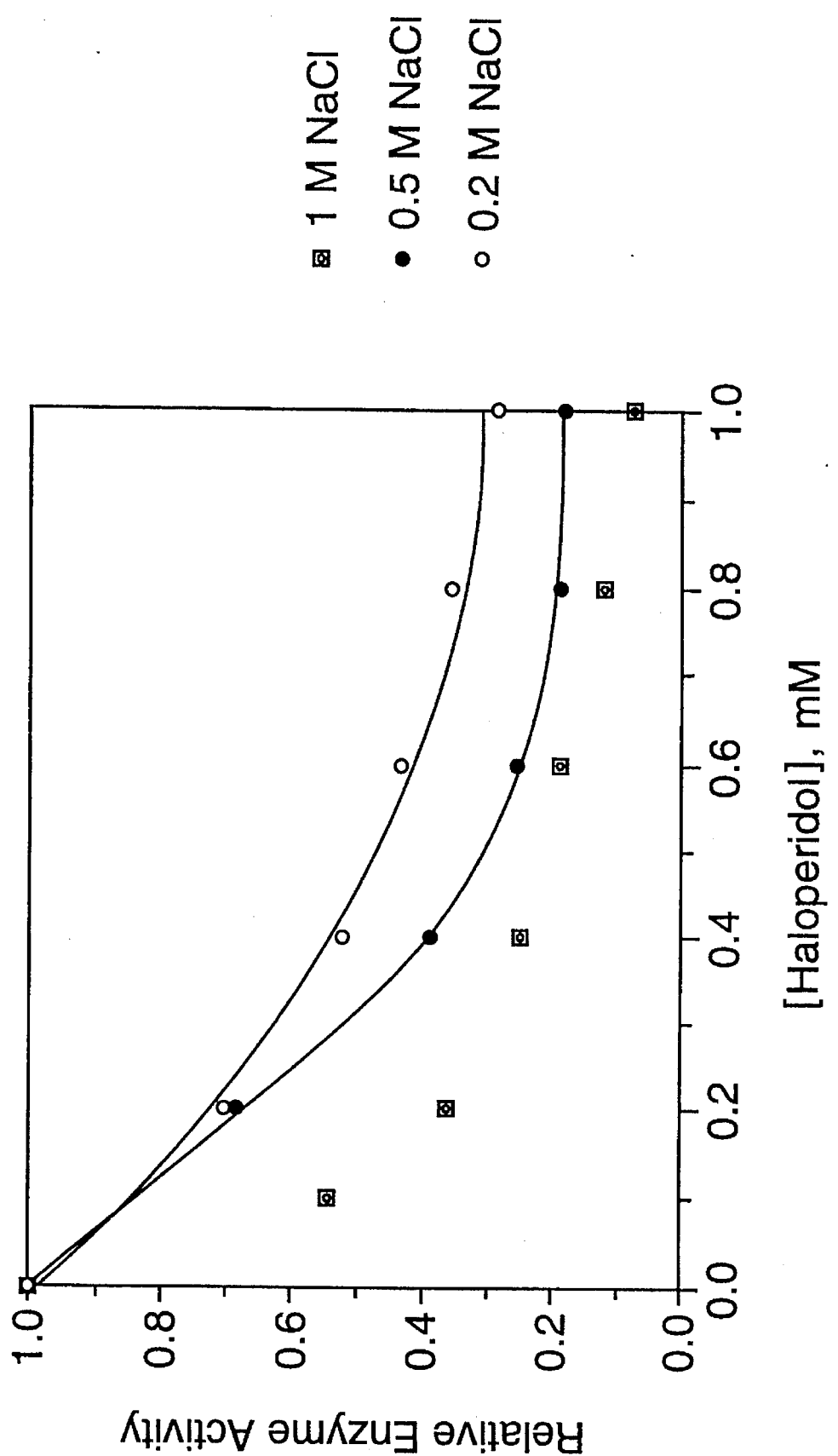
FIG. 4 graphically shows the inhibition of HIV-1 protease with haloperidol.

A second assay was performed using three salt concentrations and increased concentrations of UCSF 1o FIG. 4 graphically shows the results. Inhibition is seen with 0.2 mM UCSF 1 at all salt concentrations. Again, the greater sensitivity is seen at 1M NaCl; at this salt concentration, the enzyme is inhibited more than 60% at 0.2 mM haloperidol.

EXAMPLE 62

Figure 5:
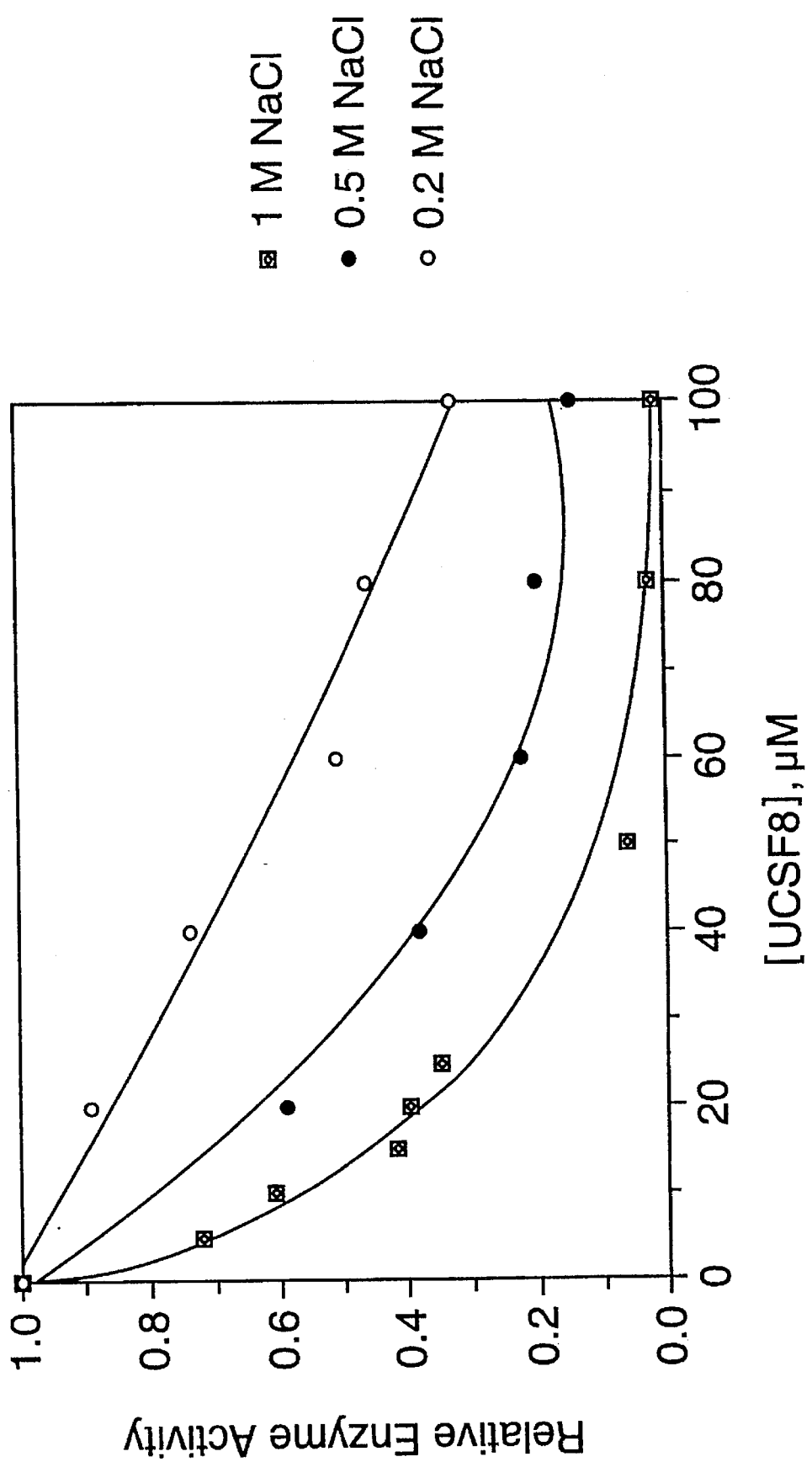
FIG. 5 graphically shows the inhibition of HIV-1 protease with a further protease inhibitor within the scope of this invention.

The second assay performed in Example 61 (above) was used to evaluate additional compounds of the present invention. FIG. 5 graphically shows the inhibition of HIV-1 protease with the compound UCSF8. (The synthesis of this compound is described in Example 8, above). Using this compound, 50% inhibition is achieved at a much lower inhibitor concentration relative to haloperidol (compare FIGS. 4 and 5).

Figure 6:
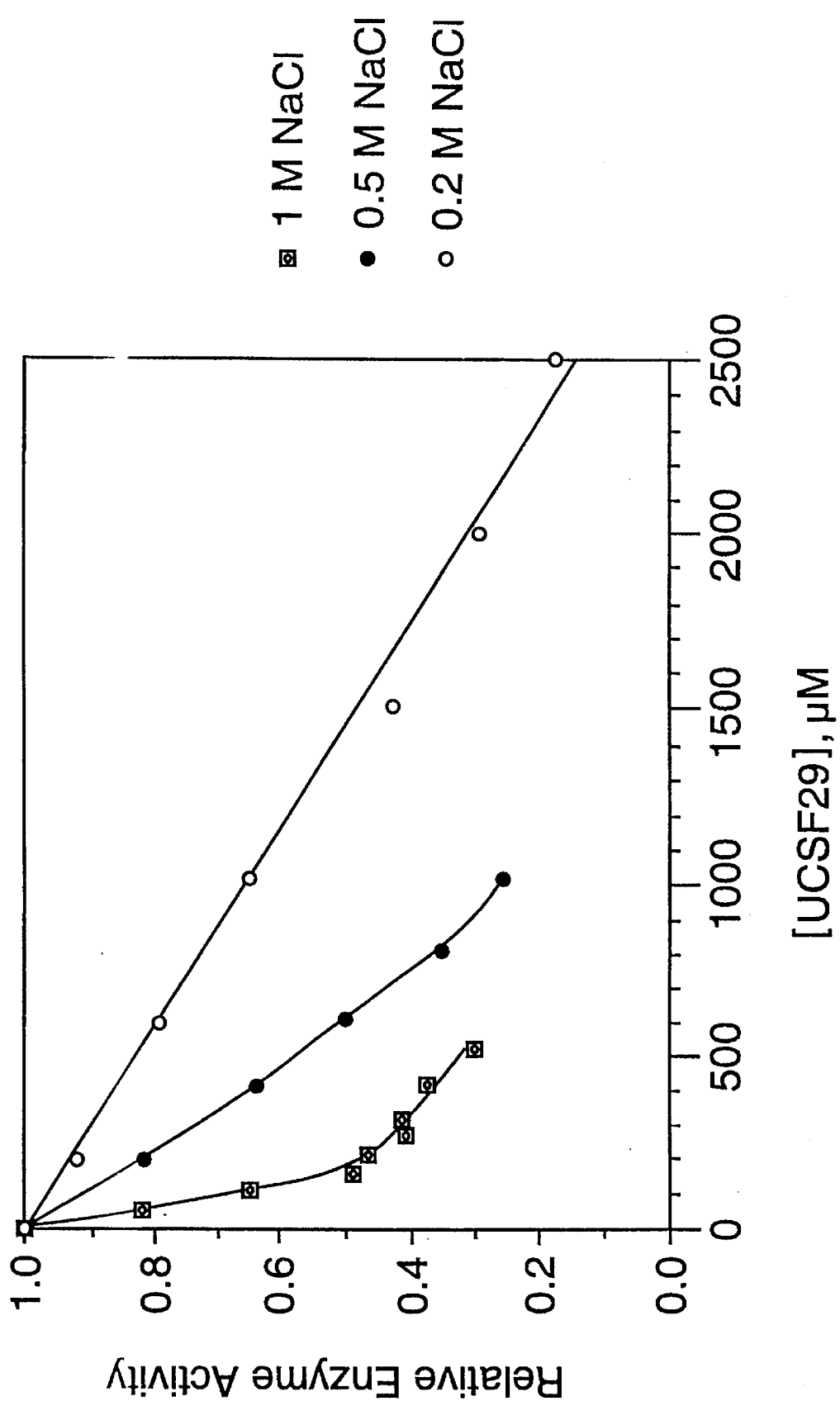
FIG. 6 graphically shows the inhibition of HIV-1 protease with a further protease inhibitor within the scope of this invention.

FIG. 6 shows the inhibition of HIV-1 protease with the cyclohexanol derivative UCSF29. (The synthesis of this compound is described in Example 25, above). Inhibition of HIV-1 protease with this compound is not unlike that for haloperidol.

Figure 7:
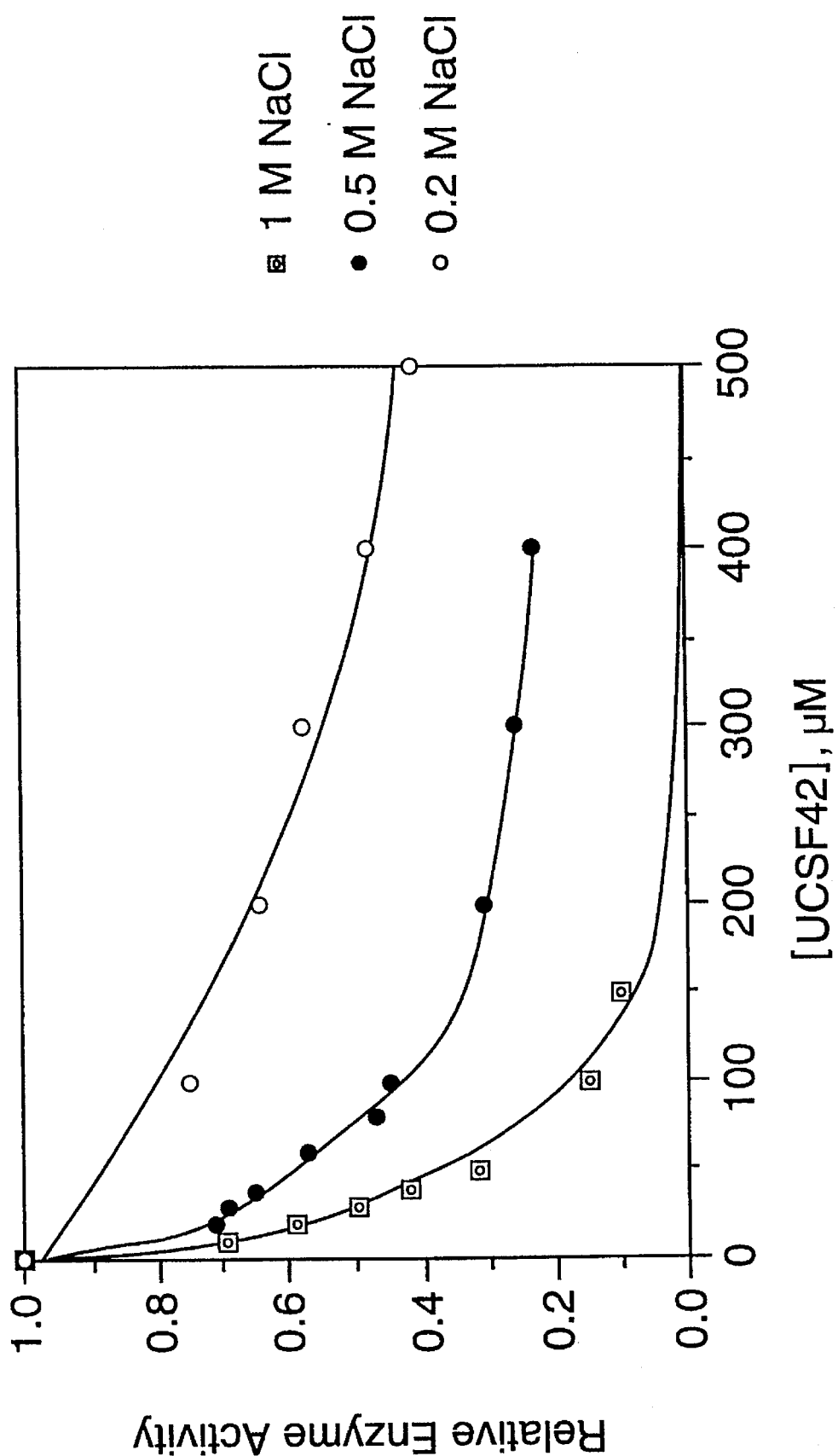
FIG. 7 graphically shows the inhibition of HIV-1 protease with a further protease inhibitor within the scope of this invention.

FIG. 7 graphically shows the inhibition of HIV-1 protease with the compound UCSF42. (The synthesis of this compound is described in Example 37, above). This compound is a better inhibitor than haloperidol but not as potent an inhibitor as UCSF8.

Figure 8:
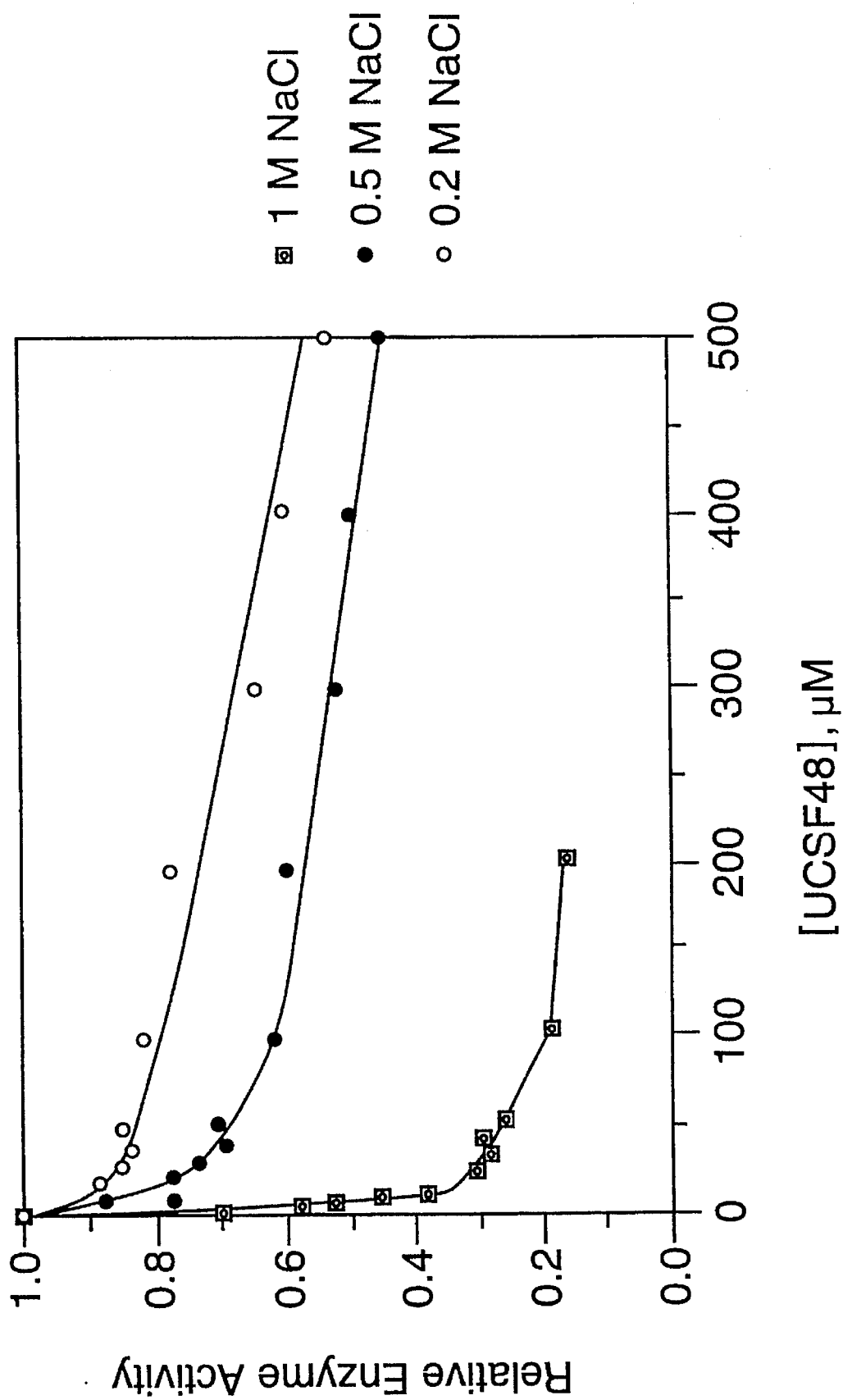
FIG. 8 graphically shows the inhibition of HIV-1 protease with a further protease inhibitor within the scope of this invention.

FIG. 8 graphically shows the inhibition of HIV-1 protease with the compound UCSF48. (The synthesis of this compound is described in Example 41, above). This compound is a slightly better inhibitor than USCF42 at 1M NaCl. Very little inhibition is observed at the lower salt concentrations.

EXAMPLE 63

Example 62 describes the inhibition of HIV-1 protease by haloperidol. In this example, both HIV-1 and HIV-2 protease are examined in the inhibition assay using the octapeptide Ser-Gln-Asn-Tyr-Pro-Ile-Val-Gln (SEQ ID No.: 6), corresponding to the HIV-1 matrix-capsid cleavage site (underlined residues indicate the point of cleavage). Reactions were carrier out in 0.1 mL volumes in 0.1M sodium acetate buffer, pH 4.7, containing 4 mM EDTA, 1M NaCl. The concentration of the peptide substrate was 250 µM. The protease ($3\times10^{-4}$ mg/mL for a final concentration of approximately 15 nM) was added to initiate the reaction. The reaction was stopped after 1 hour at 37° C.

Figure 9:
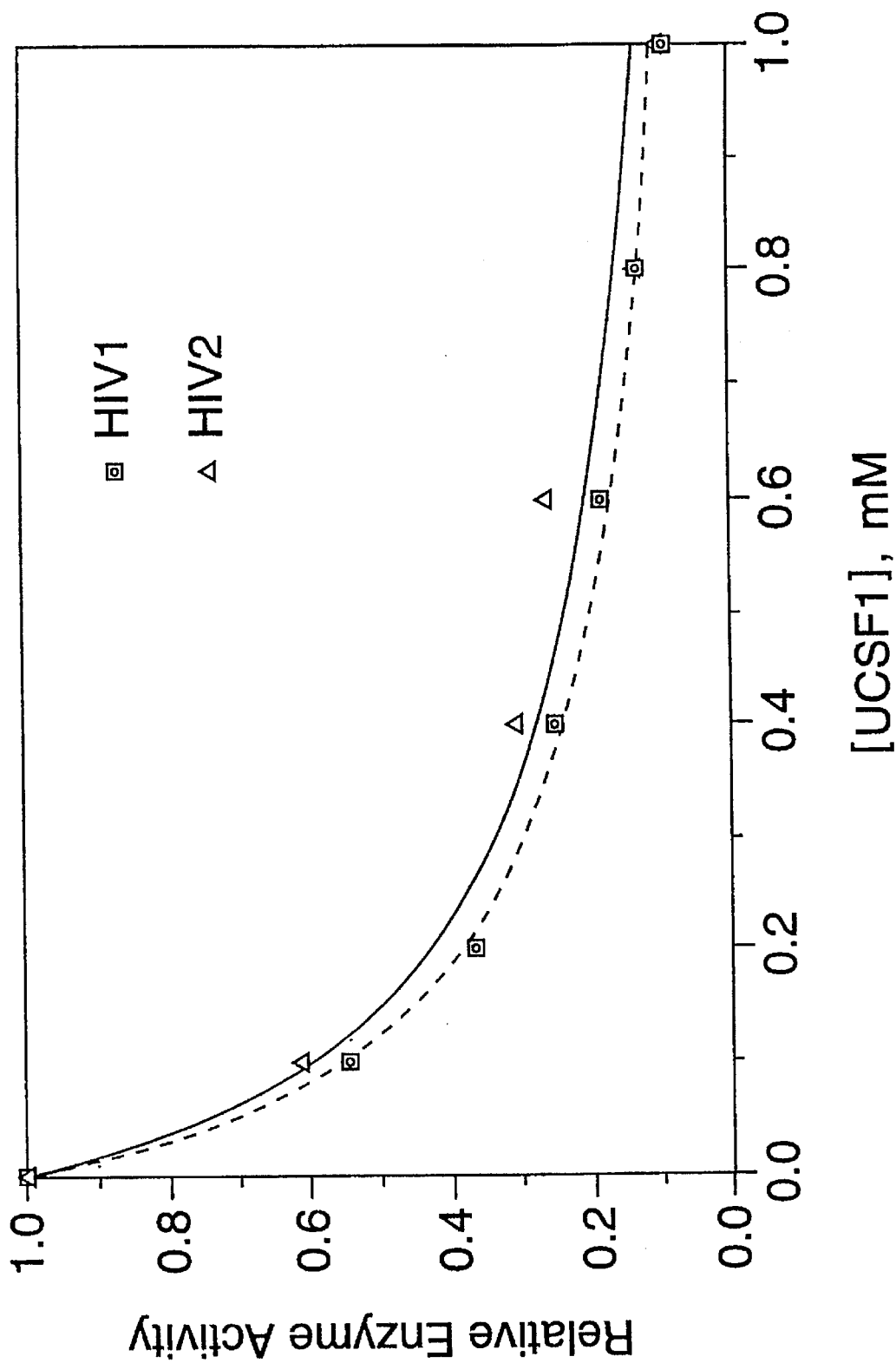
FIG. 9 graphically compares the inhibition of HIV-1 and HIV-2 proteases by haloperidol.

The results are shown in FIG. 9. Both proteases are inhibited by the compound and show nearly identical inhibition curves.

EXAMPLE 64

In this example, the inhibition of HIV-1 protease is performed with the compound UCSF84, to show that this compound, which is an epoxide, blocks hydrolysis of the substrate by the protease in an irreversible fashion. To illustrate this, the behavior of this compound is compared with that of haloperidol, a non-epoxide compound.

As noted earlier, epoxides undergo acid catalyzed hydrolysis. Therefore, the inhibition assay involved a pre-incubation step where the binding of the test compounds was done under conditions that favor the reaction with the protease. After preincubation, the enzyme-inhibitor solution was diluted and assayed for activity. Specifically, HIV-1 PR (100 µg, 400 µL final volume) was preincubated in the presence of 100 µM UCSF84, 100 µM of haloperidol or no inhibitor at 25° C. in 50 mM HEPES buffer (pH 8.0) containing 1M NaCl, 1 mM EDTA, 1 mM DTT and 5% DMSO. At various times, aliquots were removed and assayed for activity. HIV-1 PR was assayed against the fluorescent substrate ABZ-Thr-Ile-NLe-Phe(p-NO$_2$)-Gln-Arg-NH$_2$. (SEQ ID No.: 7) The enzyme was assayed at pH 6.5 in the absence of NaCl as described by Toth, M. V., et al., *Int. J. Peptide Protein Res.* 36:544–550 (1990). To confirm the reversible nature of the inhibition, after two hours of preincubation the samples were buffer exchanged using microconcentrators, then assayed. After buffer exchange and dilution, the calculated concentration of UCSF84 and haloperidol was less than 2 nM.

Figure 10:
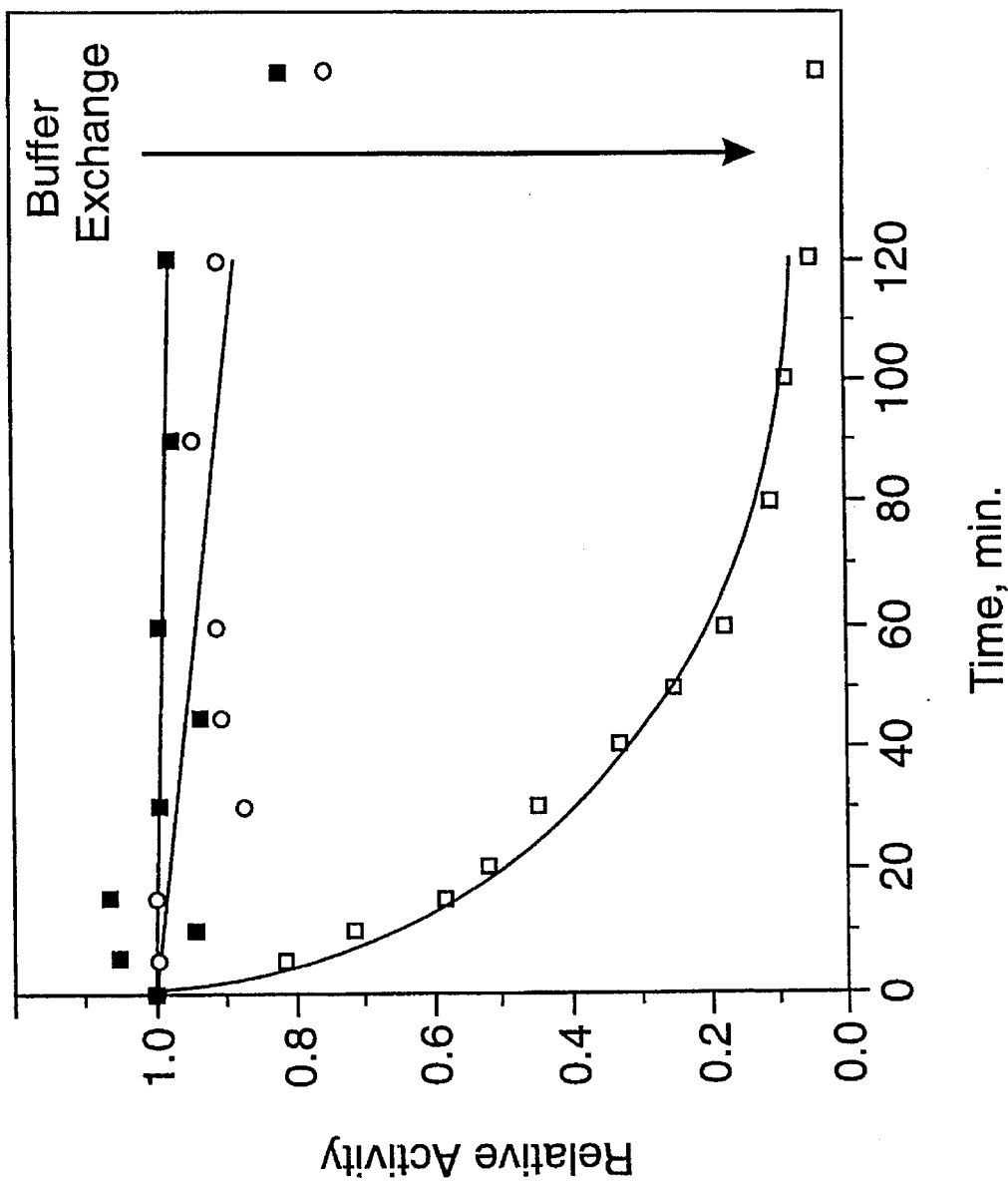
FIG. 10 graphically shows the irreversible binding character of one of the protease inhibitors of the invention in comparison with haloperolidol.

The results of the activity determinations are shown in FIG. 10, where the circles represent the test performed with no inhibitor, the filled squares represent the test performed with haloperidol, and the open squares represent the test performed with the peroxide compound UCSF84. The curve representing the test with UCSF84 shows that the protease remained inactive after dilution and assay as well as after buffer exchange, indicating an irreversible modification of the enzyme. In contrast, the curve representing the test with haloperidol, when compared with corresponding values from the curve in FIG. 10 representing the enzyme activity without either dilution or buffer exchange, indicates that dilution restored the protease activity, and that the activity essentially remained upon buffer exchange. This indicates that inhibition of the enzyme by haloperidol was reversible. The remaining curve indicates that preincubation of the enzyme in the presence of DMSO had no effect on the activity of the enzyme or on the recovery of activity after buffer exchange.

EXAMPLE 65

This example describes the inhibition of polyprotein processing in bacteria with compounds in accordance with this invention. FIG. 11a schematically shows the autoprocessing of HIV-1 protease.

*E. coli* strain D1210 harboring plasmid pSOD/PR179 (see above) was grown at 37° C. in Luria broth containing ampicillin (100 µg/mL). Cultures were grown to OD$_{650}$=0.4 at which time IPTG was added to a final concentration of 200 µM for induction and 5-mL samples of the cultures were removed. Compounds of this invention were dissolved in DMSO to 50 mg/mL. The appropriate volumes of these stock solutions were added within 5 minutes of induction to achieve a final concentration of 500 µM. The cultures were returned to the orbital shaker at 37° C. and 1-mL samples were collected at 15 and 120 minutes. The OD$_{650}$ of each culture was determined and equivalent concentrations of cells (0.2 unit at OD$_{650}$) were pelleted by centrifugation. The cell pellets were resuspended in 30 µL of 1×Laemmli sample buffer, heated at 95° C. for 10 minutes, and passed repeatedly through a syringe needle to shear the chromosomal DNA, and the sample was clarified by centrifugation. The supernatant was then loaded onto a 12.5–17.5% gradient polyacrylamide gel containing SDS and subjected to electrophoresis. The gels were immunoblotted and probed with antibodies to the HIV-1 protease as described above.

Electrophoresis was performed after fifteen minutes of autoprocessing of the proteins in the presence of the inhibitors. The gel, which is shown in FIG. 11b, includes six lanes representing, respectively: (1) DMSO treatment (control); (2) untreated proteins; (3) markers obtained from BRL; (4) cerulenin; (5) UCSF1; and (6) UCSF2. Comparison of lane (5) with the other lanes shows a marked increase in the intensity of the bands representing the 35-kDa and 38-kDa intermediates, indicating that protein processing was being inhibited by UCSF1. No such increase is observed in the cerulenin lane, indicating that no detectable inhibition by cerulenin was observed during this interval.

Electrophoresis was also performed on the proteins after 120 minutes exposure to the inhibitors, and the gel with the same six lanes as the fifteen-minute gel is shown in FIG. 11c. The gel indicates protein processing inhibition by both UCSF1 and cerulenin, as evidenced by increases in the intensity of the 35-kDa and 38-kDa bands. An increase in the band representing an intermediate in the vicinity of the 29-kDa marker is observed in the UCSF2 lane. No concomitant decrease is observed in the mature 11-kDa protease band for any inhibitor. This is due to the high levels of expression and processing of the mature protease by this expression system.

For the next two examples, the following materials and methods were used.

Cells lines and vectors. COS-7 and HeLa/T4 cells were maintained in DME H21 media supplemented with 10% dialyzed fetal calf serum (Gibco, Long Island, N.Y.) and antibiotics (100 U/mL penicillin G, 100 µg/mL streptomycin sulfate). Plasmids HIV-gpt (guanidyl phosphate ribosyltransferase) and HXB2-env were kindly provided by K. Page and D. Littman (University of California, San Francisco).

MTT cell viability assay. This is a quantitative colorimetric assay for mammalian cell survival and proliferation. Cells were seeded in 96 well plates and grown to near 50% confluency. A serial dilution (1 to 500 µM) of each compound was then prepared in culture media and added (250 µL/well) in duplicate. All culture media was adjusted to a final concentration of 1.0% DMSO (volume basis). The cells were allowed to grow for either 4 hours or 24 hours. The culture media were then removed, and the cells were washed with phosphate buffered saline (PBS) before 50 µL of MTT solution (1 mg/mL in PBS) was added. After incubating for 4 hours at 37° C., the reaction was quenched by adding 160 µL of acidified isopropanol and mixing to dissolve purple crystals. The absorbance was determined within 30 minutes at 570 nm on an ELISA plate reader. LD$_{50}$ values for each compound were then determined from a plot of the average of the observed absorbance versus the concentration of the inhibitor.

Production of virus. Virus was generated by co-transfection of plasmid DNA HIV-gpt and HXB2-env into COS-7 cells by the calcium phosphate procedure with the following modifications. Twenty micrograms of each plasmid was added to 10 cm dishes of cells at 50% confluency in the presence of 100 µM chloroquine. Following overnight incubation, the culture medium was replaced. Virus production was detectable within 12 hours and peaked between 48 and 65 hours post-transfection.

Drug treatment. The compounds were added 48 hours post-transfection, at the peak of virus production, and the incubation was restricted to a 4-hour period. Due to their low solubility in aqueous solutions, concentrated stock solutions (generally 50 mM) were prepared in neat DMSO. Culture media were adjusted to the desired concentration of these compounds just prior to the addition of the media to cells. To avoid precipitation, the compounds were aliquoted first to a tube in sufficient DMSO to yield a 1.0% final concentration, and subsequently the culture medium was added quickly and vortexed. The culture medium was collected after 4 hours of incubation of the cells with each of the compounds. This culture supernatant is the source of virus for measurement of infectivity as well as levels of p24 and other capsid proteins.

Infectivity measurements. HeLa/T4 cells were seeded at 2.5×10$^5$ cells/culture well. A 500 µL aliquot of culture media containing the virus to be titered was then added (using dilutions of 1:2, 1:5, and 1:20). The virus was then allowed to be absorbed for 45 minutes at 37° C. The supernatant was aspirated and 1.5 mL of fresh media were added to the culture overnight. Selective media containing 50 µg/mL mycophenolic acid (CalBiochem), 14 µg/mL hypoxanthine and 250 µg/mL xanthine were then added and the selection allowed to take place for 12–14 days during which cells expressing the gpt gene survived and formed colonies. The colonies were then stained with 0.5% crystal violet and 1% formaldehyde in a 1:1 ethanol/PBS solution. The colonies were counted and the average was determined from duplicate wells. The reduction in infectivity was calculated as a percentage of colonies from treated versus untreated cells in duplicate wells.

p24 Core antigen ELISA assay. An ELISA kit purchased from NEN/Dupont was used to determine the amount of p24 present in culture media or virus preparations. This capture assay uses a monoclonal antibody that preferentially binds p24 while it reacts with larger capsid protein precursors to a very limited extent. The assay was carded out using the manufacturer's indications. Samples were pre-treated with 1% Triton to inactivate the virus.

Virus isolation by ultracentrifugation. The culture medium was filtered through a 0.45 µm syringe filter and was then centrifuged to remove any precipitate. The medium was then spun through a cushion of 20% sucrose in PBS in an SW41 Beckman rotor for 1.5 hours at 35K and 4° C. The pelleted material was collected.

EXAMPLE 66

In this example, a series of compounds which inhibited the HIV protease in vitro were selected for testing in an in vivo cell culture viral assay. An HIV vector system designed to produce replication-defective virions was used to measure the effect of these compounds on capsid polyprotein processing as well as on viral infectivity in vivo. The advantage of this assay is that the virions are noncytopathic.

Figure 12:
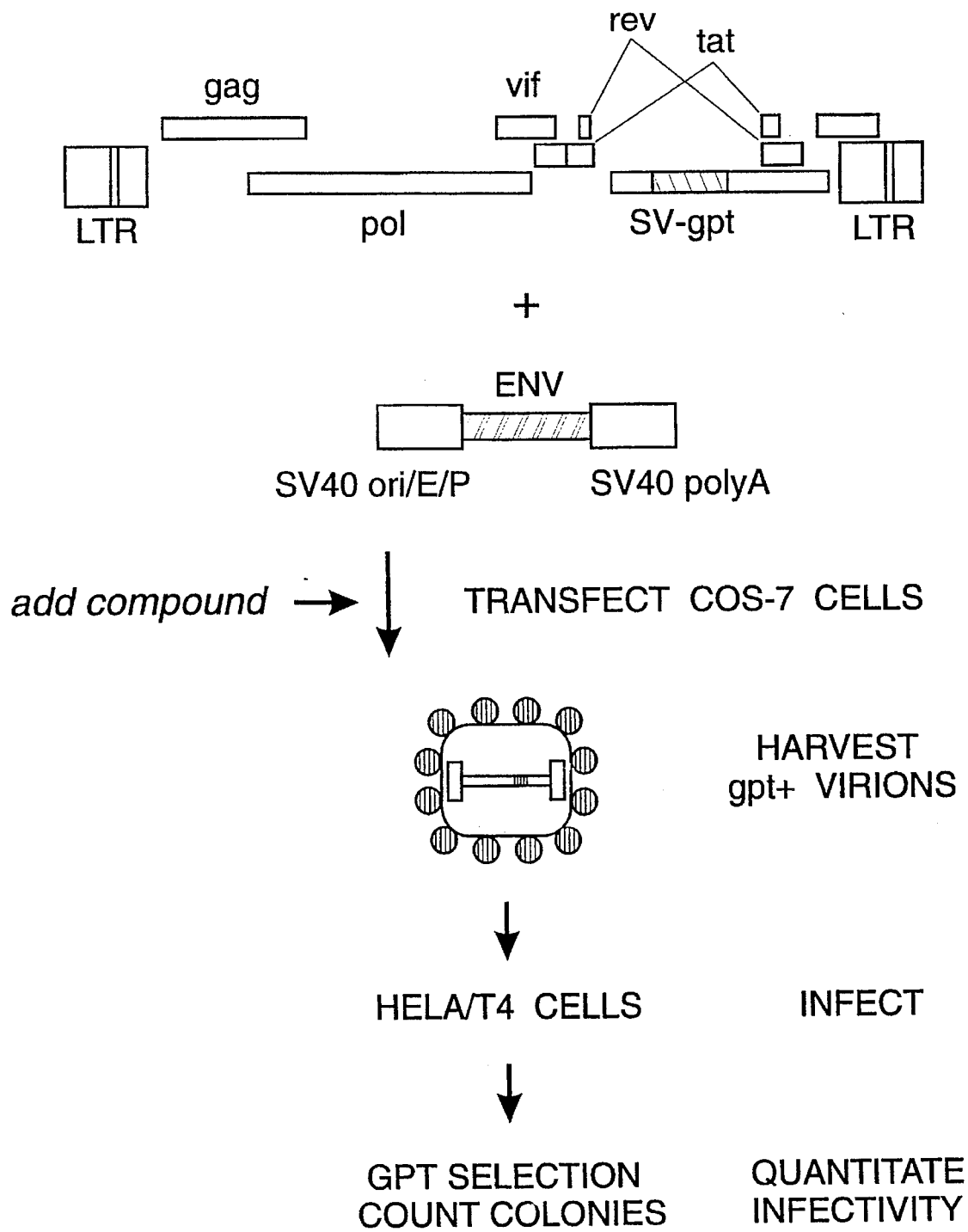
FIG. 12 schematically shows an in vivo assay for measuring inhibition of viral infectivity and processing.

Virions are produced by co-transfection of COS-7 cells with two expression vectors as illustrated in FIG. 12. One SV40-based vector consists of the HIV proviral genome where the gp 160 sequences were replaced by the guanidyl phosphate ribosyltransferase (gpt) gene, while the other vector contains the gp 160 sequences. Since the virions produced are capable of infecting CD4 positive cells, the number of infectious particles can be quantitated by placing the infected cells under selective pressure and counting drug-resistant colonies. A compound able to inhibit the HIV protease specifically would exert its effect during virus assembly and processing. To measure this effect, the transfected cells were treated with various compounds for short periods of time and the culture supernatant was collected to measure infectious particles as well as levels of capsid protein processing. The concentrations chosen for the in vivo inhibition trials were based on the $IC_{50}$ values obtained in vitro and the effect of the compounds on cell viability. The length of time the cells could be exposed to the compounds was limited by their toxicity.

HeLa/T4 cells were seeded and allowed to grow in 6 well plates until approximately 25% confluency ($2.5 \times 10^5$ cells/well). At this time, the media from the cells was aspirated and 500 µL culture media containing virus to be titered was added. (It may be desirable to try different dilutions of virus samples if a high titer is expected). The mixture was incubated, allowing the virus to be absorbed for 30 to 60 minutes at 37° C. Thereafter, 1.0 mL media was added and the mixture was cultured overnight. At this time, selective media containing 50 µg/mL mycophenolic acid (CalBiochem), 14 µg/mL hypothanthine and 250 µg/mL xanthine was added. Selection is allowed to take place for 12–14 days (changing media every 3 days to remove dead cells) and surviving cells are allowed to form colonies.

To stain the colonies, they were first washed with 1 mL PBS, then 0.5 mL of crystal violet solution was added (0.5% crystal violet in 50% ethanol, 50% PBS and 1% formaldehyde). The mixture was incubated 1 minute and then the colonies were rinsed with PBS. The colonies were counted, taking an average for 2–3 wells. The reduction in infectivity was calculated as a percentage of colonies from treated versus untreated cells (see Table 5).

TABLE 5

| | | 4-Hour Treatment of Transfected COS-7 Cells | | | |
|---|---|---|---|---|---|
| Compound Code No. | Concentration (µM) | Hela/T4 Infection % Colony Reduction | MTT Assay (4 h): % Non-viable Cells | $LD_{50}$ (µM) | % p24 Relative to Untreated |
| UCSF1 | 20 | 40 | 38 | 400 | 44 |
| UCSF1 | 500 | 64 | 55 | 400 | 51 |
| UCSF8 | 20 | 85 | 55 | 45 | 62 |
| UCSF29 | 250 | 100 | 80 | 180 | 35 |
| UCSF42 | 75 | 92 | 0 | 300 | 45 |
| cerulenin | 100 | 77 | 0 | 900 | 36 |
| U75875 | 1 | 81 | 0 | 45 | 25 |
| 0.5% DMSO | | 0 | 0 | NA | 100 |

The compounds UCSF1, 8, 29 and 42 show a significant colony reduction. Cerulenin and the compound U75875 have both been shown effective as HIV protease inhibitors in the literature and are useful controls.

EXAMPLE 67

In this example, protein expression was measured using a stable transformed cell line (COSA6) expressing the gpt genes. The cells were grown under selection to approximately 75% confluency and incubated with inhibitor compounds. Viral capsids were purified by filtering culture supernatants through 0.2 or 0.45 µm syringe filters (adjusting to 0.5% formaldehyde to inactivate the virus and spinning for 10 minutes at 3K to remove any precipitate). Seven mL of culture supernatant were layered over a cushion consisting of 75 µL of 60% sucrose in PBS overlayed with 4 mL of 20% sucrose in PBS. The sample was spun in an SW41 Beckarian rotor for 1.5 hours at 35K and 4° C. To collect the virus which bands at the interface of the 20 and 60% sucrose solutions, suction was applied at the top of the tube to remove all but the bottom 0.5 mL.

Figure 13:
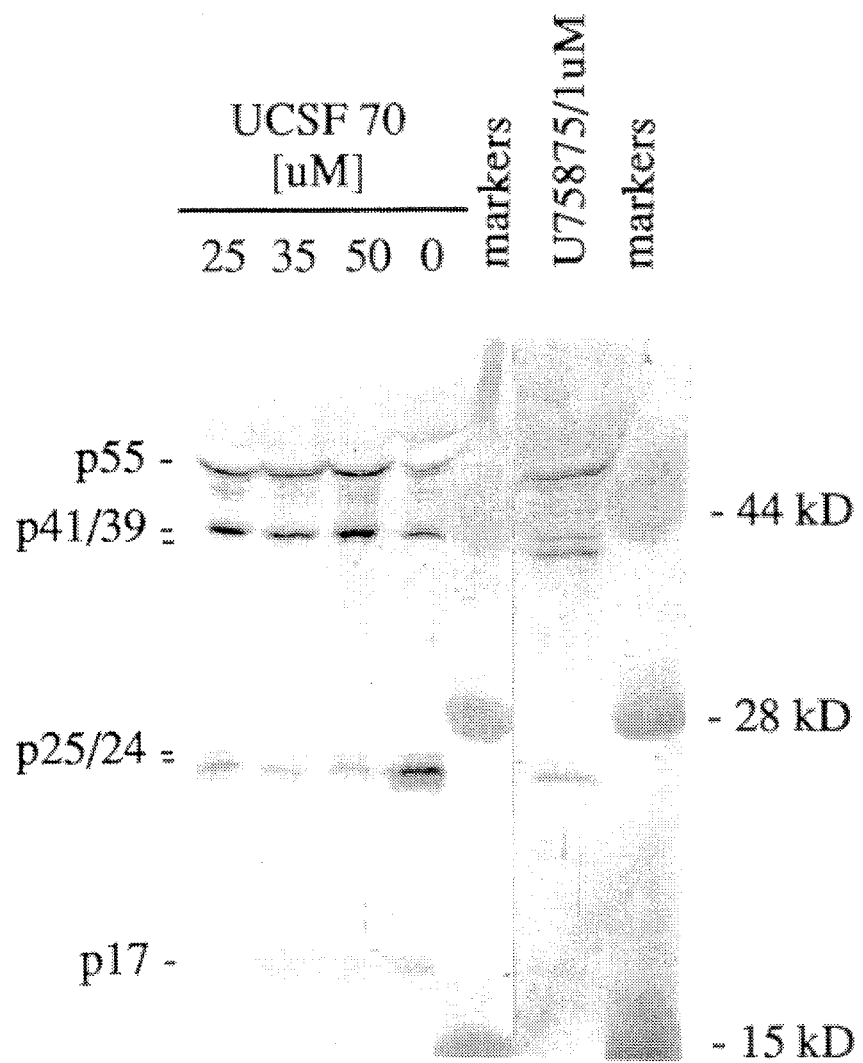
FIG. 13 is a Western blot of polyprotein processing in an HIV-infected cell in the presence of an inhibitor within the scope of the invention.

Polyprotein processing was measured by Western blot using an antibody that reacts with HIV-1 p24 capsid and its precursors p55 and p41/39. The Western blot, which is shown in FIG. 13, included two marker lanes, one lane of an untreated (DMSO treated) control, and one lane of a sample from cells treated with the peptidomimetic inhibitor U75875 at a concentration of 1 µM. The remaining lanes represent UCSF70 at concentrations of 25, 35 and 50 µM. All lanes were examined for indications of the ability of the inhibitors to reduce the expression of p24 and cause an increase in detectable p55 and p41/39 capsid precursors. The U75875 lane confirmed the effect of this known HIV protease inhibitor by showing a reduction in the amount of p24 reacting with the antibody. A similar inhibition pattern was observed at increasing concentrations of UCSF70 in comparison with the untreated sample.

EXAMPLE 68

This example illustrates the use of the compounds of the present invention in labelling the protease by virtue of the increase in molecular weight due to the covalent binding. The increase in molecular weight is detected by mass spectrometry.

HIV-1 PR (100 μg) was incubated with UCSF142 at 25° C. in 50 mM HEPES at pH 8.0, 1M NaCl, 1 mM EDTA, 500 μM DTT, and 5% DMSO to achieve full inhibition of the enzyme. Once full inhibition was achieved, the enzyme was isolated by reverse phase HPLC on a $C_3$-Zorbax Protein Plus column (4.6 mm×25 cm), using a 100-minute linear gradient from 5 to 65% acetonitrile in 0.1% TFA. The flow rate was 1 mL/min and the eluent was monitored at 220 nm. The two major components of the isolated sample were concentrated under vacuum, dissolved in a small volume of 50% acetonitrile and 1% acetic acid, and their molecular weights determined by electrospray mass spectrometry. The spectra were recorded on a VG Electrospray. Mass Spectrometer Model Bio-Q.

Figure 14A:
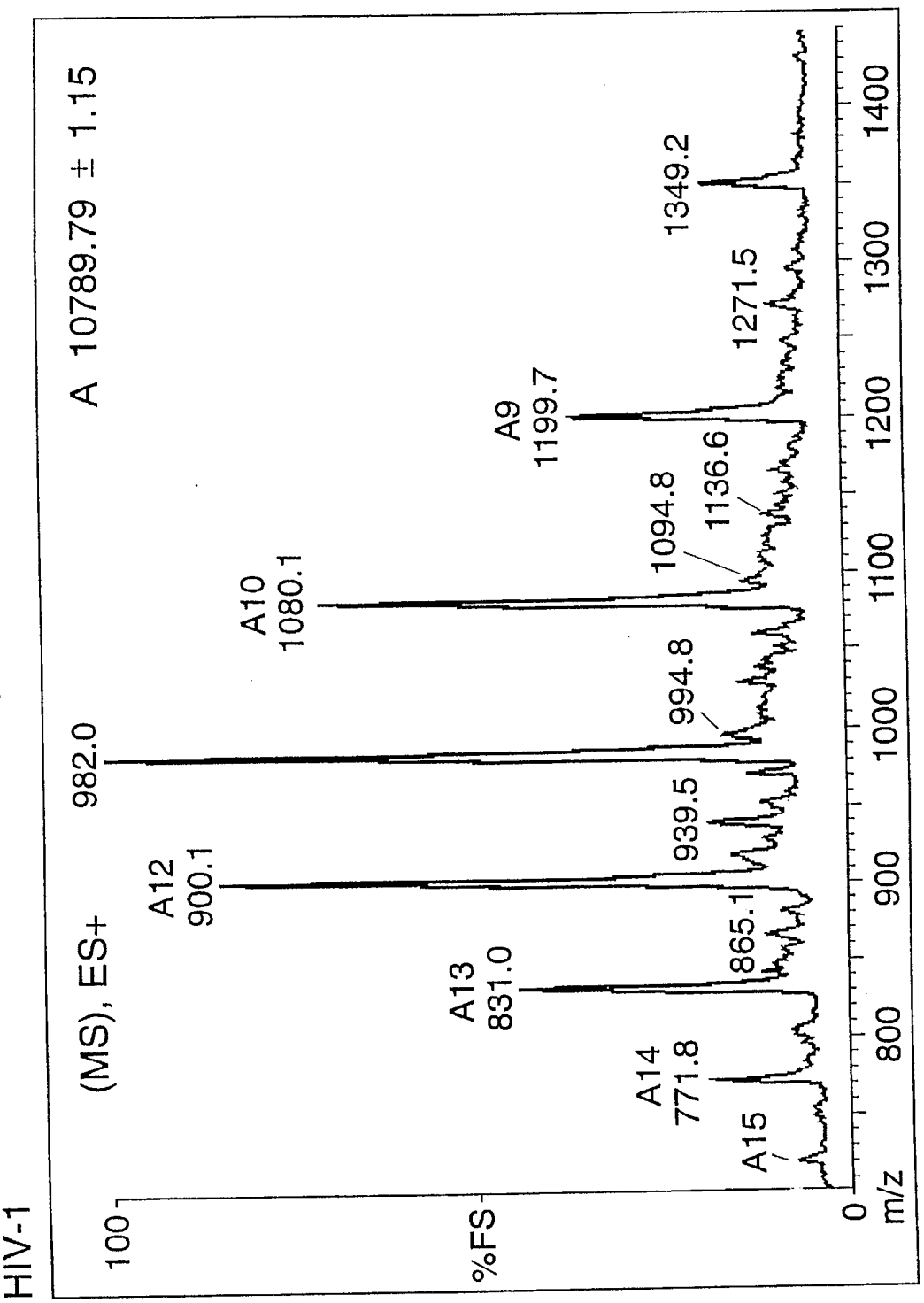
FIGS. 14a and 14b are electrospray mass spectra showing molecular weights of HIV-1 protease, both free and bound to a protease inhibitor in accordance with the present invention.
Figure 14B:
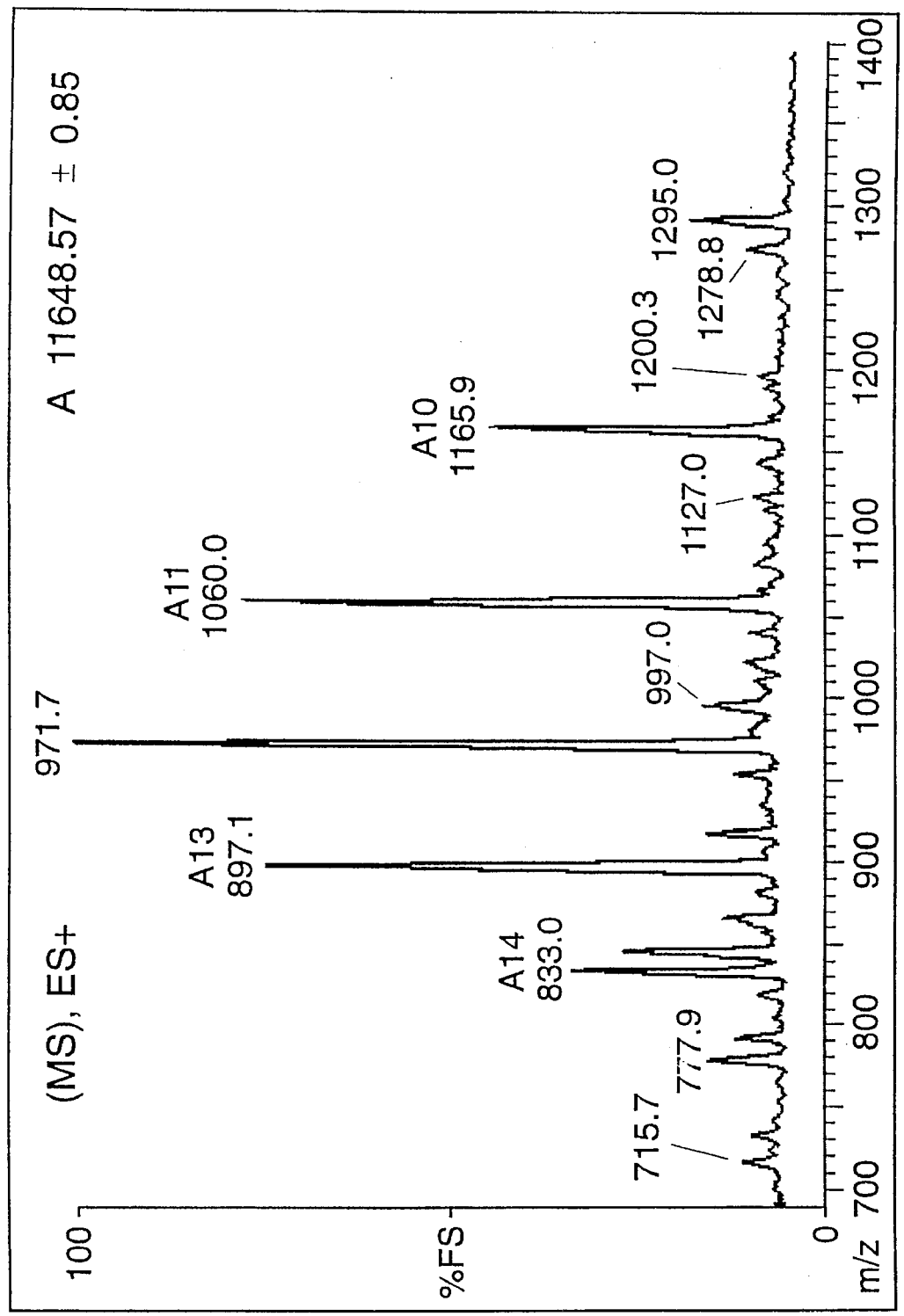

The results of the experiment are shown in FIGS. 14A and 14B, which show the molecular weight of the two major components isolated after labeling. FIG. 14a shows a molecular weight of 10,790 that corresponds to the non-modified HIV-1 protease. FIG. 14b shows a molecular weight of 11,649. This molecular weight corresponds to the HIV-1 protease plus two molecules of UCSF142, which has a molecular weight of 430.

EXAMPLE 69

This example illustrates a radio-labelled analog of a compound of the present invention for use as a topological and mechanistic probe of retroviral proteases.

The compound UCSF84 was synthesized using materials which incorporate the radiolabel $^{14}C$ into its structure. HIV-1 PR and the variant protease HIV-1 PR C95M, both at final concentrations of 1.6 μM, were incubated in the presence of radio-labelled UCSF84 (200 μM). The variant protease HIV-1 PR C95M is characterized by a methionine in place of the cysteine residue at position 95 of HIV-1 PR. The enzymes were incubated for one hour at 25° C. in 50 mM HEPES, pH 8.0, 1M NaCl, 1 mM EDTA, 500 μM DTT and 5% DMSO.

A protection experiment was performed to show that UCSF84 binds to the active site of HIV-1 PR. The experiment involved the use of the Asp25 specific irreversible inhibitor 1,2-epoxy-3-(p-nitrophenoxy)-propane (EPNP) and the transition state analog inhibitor Val-Ser-Asn-Ler-ψ [CH(OH)CH$_2$]-Val-Ile-Val (SEQ ID No.: 8) (U-85548), which are known to bind to the active site of HIV-1 PR. HIV-1 PR and HIV-1 PR C95M, each at final concentrations of 1.6 μM, were separately incubated in the presence of radio-labelled UCSF84 (200 μM) for one hour at 25° C. in 50 mM HEPES pH 8.0, 1M NaCl, 1 mM EDTA, 500 μM DTT, and 5% DMSO. In some cases, the enzymes were first preincubated in the presence of U-85548 at 10 μM final concentration or EPNP at 10 μM final concentration for one hour. Following preincubation of the enzymes with the protective reagents, radiolabelled UCSF84 was added. The extent of radioactivity bound to the enzyme was quantitated by separating the reaction mixtures on SDS/PAGE followed by autoradiography of the protease bands. The results are shown in FIG. 15, Panel A, where HIV-1 PR is represented by the blank bars and HIV-1 PR C95M is represented by the shaded bars.

The experiment was repeated with HIV-2 PR, using 3.2 μM final concentration, incubated in the presence of radio-labelled UCSF84 and EPNP, with the result indicated in Panel B of the Figure.

The results indicate that EPNP blocks approximately 50% of the radioactivity incorporation to HIV-1 PR, and U-85548 blocks approximately 65% of the radioactive incorporation. Attempts to label the same amount of HIV-1 PR C95M with $^{14}C$-UCSF84 resulted in only about 50% incorporation of radioactivity relative to HIV-1 PR, and this amount of incorporation was sharply reduced by preincubation of the enzyme with either EPNP or U-85548. This indicates that UCSF84 reacts with both the active site of the HIV-1 protease and with a cysteine residue at position 95. This is consistent with the stoichiometry of two inhibitors per HIV-1 protease observed in the preceding example. The experiment with HIV-2 PR shows almost complete elimination of radioactivity incorporation as a result of preincubation with EPNP.

EXAMPLE 70

This example illustrates the use of compounds UCSF70, UCSF84, UCSF86, UCSF142, UCSF231, UCSF115, UCSF191, and UCSF178 in an in vitro assay of HIV-1 and HIV-2 protease inhibition.

Recombinant HIV-1 PR Q7K, an HIV-1 PR variant that has the same kinetic parameters of HIV-1 PR but an increased resistance to autoproteolysis, was used. See Rose, et al., *J. Biol. Chem.* 268:11939 (1993). Recombinant HIV-1 PR Q7K was expressed in *E. coli* strain X90 using the pT2HIV2/115 vector. The enzymes were purified to homogeneity, as judged by a single band on a silver strained SDS polyacrylamide gel, using a combination of ion-exchange chromatography and affinity chromatography on pepstatin-A agarose. Concentrations of active HIV-1 and HIV-2 enzymes were determined by active site titration using the peptidomimetic inhibitor U-85548 (see Example 69).

The irreversible inactivation of HIV proteases by the inhibitors of the present invention was quantified by preincubating HIV-1 Q7K PR (at a final concentration of 15 μg/mL) and HIV-2 PR (at a final concentration of 30 μg/mL) at 25° C. in 50 mM HEPES at pH 8.0, 1M NaCl, 1 mM EDTA, 500 μM DTT and 5% DMSO in the presence of 10 μM to 1 μM of each inhibitor. Baseline measurements were performed using 5% DMSO in the absence of inhibitors. At various times, aliquots were removed and assayed for activity. HIV proteases were assayed against the fluorescent substrate ABZ-Thr-Ile-NLe-Phe(p-NO$_2$)-Gin-Arg-NH$_2$. (SEQ ID No.: 1) The enzymes were assayed at pH 5.4 in 1M NaCl, 1 mM EDTA, and 1 mM DTr. For the calculation of the rates of inactivation, kinetic data were fitted to a pseudo-first order equation according to the formula $$Ln(v/v_o) = -k_{obs} \times t.$$

From a double reciprocal plot of inactivation rates ($k_{obs}$) vs. inhibitor concentrations the $k_{inact}$ (the inhibitor concentration resulting in half-maximal inactivation) and the $V_{inact}$ (the maximum inactivation rate) were calculated.

The results are shown in Table 6. The kinetic parameters of the specific irreversible inhibitor EPNP are included in the table for comparison.

TABLE 6

Inhibition of HIV-1 and HIV-2 Proteases

| Compound | $k_{inact}$ (µM) | | $V_{inact\ (min)}^{-1} \times 10^3$ | |
|---|---|---|---|---|
| Code No. | HIV-1 | HIV-2 | HIV-1 | HIV-2 |
| UCSF70 | 406.7 ± 61.6 | NI[a] | 159.6 ± 21.2 | NI |
| UCSF84 | 520.9 ± 56.6 | 282.5 ± 9.3 | 202.5 ± 21.8 | 14.6 ± 0.4 |
| UCSF86 | 62.4 ± 3.1 | 131.1 ± 4.4 | 378.7 ± 18.8 | 7.6 ± 0.2 |
| UCSF142 | 10.7 ± 1.3 | 8.6 ± 1.0 | 56.6 ± 1.9 | 9.7 ± 0.3 |
| UCSF115 | 144 ± 14.8 | 115.6 ± 4.7 | 54.0 ± 3.8 | 5.2 ± 0.2 |
| UCSF178 | 231.9 ± 10.8 | 120.3 ± 9.9 | 19.6 ± 0.7 | 4.6 ± 0.5 |
| UCSF231 | 385.3 ± 58.0 | NI | 93.1 ± 13.1 | NI |
| UCSF191 | 57.2 ± 7.1 | 156.3 ± 2.3 | 231.9 ± 18.8 | 12.1 ± 0.1 |
| EPNP | 9900 ± 1000 | 6700 ± 600 | 60.0 ± 5.6 | 48.2 ± 3.7 |

[a]"NI": no detectable irreversible inhibition

The data show that the irreversible inhibitors follow pseudo-first order kinetics and that the inactivation of HIV-1 and HIV-2 proteases by these inhibitors is saturable. The inhibitors show an improved affinity for HIV-1 and HIV-2 proteases when compared with EPNP. The values of $k_{inact}$ for UCSF70 and UCSF84 are 20-fold lower than those of EPN. The addition of a phenol ting to the structure, as in UCSF142, produces a 1000-fold decrease in $k_{inact}$ value. The maximum rates of inactivation in HIV-1 protease are about two orders of magnitude higher than those on HIV-2 protease. The rates of inhibition on HIV-2 protease are closer to the values of inhibition observed with EPNP on both HIV proteases. However, the maximum rates of inactivation for UCSF142 and UCSF15 in HIV-1 protease are similar to the EPNP values.

EXAMPLE 71

This example presents test results from an assay of HIV-1 and HIV-2 protease inhibition using compounds UCSF70, UCSF84, UCSF86, UCSF142, UCSF231, UCSF15, UCSF191, and UCSF178.

An HIV vector system designed to produce replication-defective virions was used to measure the effect of inhibitors on capsid polyprotein processing as well as on viral infectivity. Virions were produced by co-transfection of COS-7 cells with two expression vectors. One SV40-based vector consists of the HIV proviral genome in which the gp160 sequences were replaced by the guanidyl phosphate ribosyltransferase (gpt) gene. The other vector contains the gp160 sequences. Since the virions produced are capable of infecting CD4 positive cells, the number of infectious particles can be quantitated by placing infected cells under selective pressure and counting drug-resistant colonies. A compound able to inhibit the HIV-1 protease would specifically exert its effect during virus assembly and processing. To measure this effect, the transfected cells were treated with various inhibitors for short periods of time and the culture supernatant was collected to measure infectious particles as well as levels of capsid protein processing. The concentrations chosen for the ex vivo inhibition trials were based on the $IC_{50}$ values obtained in vitro and the effects of the compounds on cell viability. The length of time the cells could be exposed to the compounds was limited by their cellular toxicity.

The cytotoxic effect of the inhibitors was determined using the MTT stain viability assay. The $LD_{50}$ values, defined as the concentrations that reduce viability by 50%, were determined for all the compounds after 4-hour or 24-hour incubation periods, and are listed in Table 7.

TABLE 7

Activity of the Irreversible HIV-1 Protease Inhibitors

| Compound | $LD_{50}$ (4 h) | $LD_{50}$ (24 h) | Reduction of p24 $IC_{50}$ (µM) |
|---|---|---|---|
| UCSF70 | 70 | 35 | 25 |
| UCSF84 | 120 | 50 | 50 |
| UCSF86 | 15 | <10 | NT[a] |
| UCSF142 | 35 | <5 | NT |
| UCSF231 | <5 | <5 | NT |
| UCSF115 | 250 | 200 | 75 |
| UCSF178 | >250 | 75 | NT |

[a]"NT": not tested

Due to the toxicity of most of the compounds, the incubation periods for viral assays were restricted to 4 hours. Following incubation of virus-producing cells with various concentrations of the test compounds, the virus particles were isolated by ultracentrifugation. These particles were disrupted using Triton X-100 and the amount of p24 capsid protein was quantitated by ELISA. The effects on p24 levels reported in Table 8 were obtained at drug concentrations that had no effect on cell viability.

The foregoing is offered primarily for purposes of illustration. It will be readily apparent to those skilled in the art that the procedures, proportions, formulations, methods of administration and other parameters of the invention may be further modified or substituted in various ways without departing from the spirit and scope of the invention.

---

What is claimed is:

1. A method for detecting the presence of retroviral proteases in a biological sample, said method comprising:

(a) combining said sample with a compound having the formula

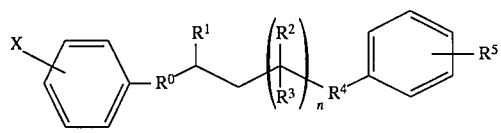

in which:

$R^0$ is

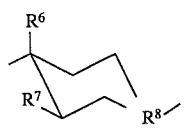

in which:
$R^6$ is OH;
$R^7$ is H; and
$R^8$ is a member selected from the group consisting of N, and C—OH;
$R^1$ is a member selected from the group consisting of H and Ph;

$R^2$ is a member selected from the group consisting of H and $CH_3$;

$R^3$ is H;

$R^4$ is a member selected from the group consisting of $CH_2$, $C=CH_2$, CHOH, $C=O$, $C=N-OH$, $C=N-NH_2$, $C=N-NH-C_2H_5OH$, $C(OH)-Ph$, $C(OH)-CH_2SCH_3$, $C(OH)-CH=CH_2$,

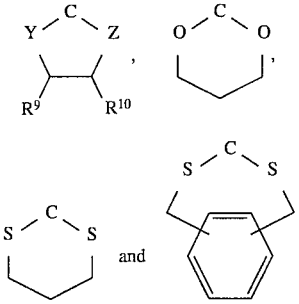

in which:
  Y and Z are members independently selected from the group consisting of O and S; and
  $R^9$ and $R^{10}$ are members independently selected from the group consisting of H and $C_1-C_3$ alkyl;

$R^5$ is a member selected from the group consisting of H, halogen and phenyl;

X is a member selected from the group consisting of H and halogen; and n is zero or 1;

where Hal is halogen and Ph is phenyl;

or a radiolabeled analog of said compound; and (b) detecting the presence of complexes formed by the binding of said compound to said retroviral proteases as a measure of the presence of said retroviral proteases in said biological sample.

2. A method in accordance with claim 1 in which:
$R^1$ is H;
$R^2$ is H; and
n is 1.

3. A method in accordance with claim 1 in which:
$R^1$ is H;
$R^2$ is H;
$R^3$ is H;
$R^4$ is a member selected from the group consisting of $C(OH)-Ph$,

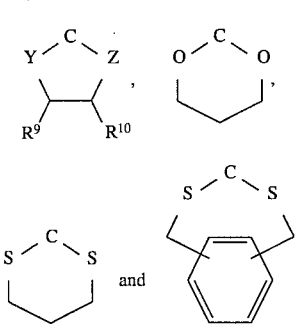

$R^8$ is N; and
n is 1.

4. A method in accordance with claim 3 in which Z and Y are either both O or both S.

5. A method in accordance with claim 3 in which Z and Y are both S.

6. A method in accordance with claim 3 in which:
$R^4$ is

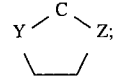

Z and Y are both S;
$R^5$ is p-fluoro;
X is p-chloro; and
n is 1.

7. A method in accordance with claim 1 in which X is p-chloro.

8. A method in accordance with claim 1 in which $R^5$ is p-fluoro.

9. A method in accordance with claim 1 in which:
$R^1$ is H;
$R^2$ is H;
$R^4$ is $C=O$;
$R^8$ is N;
X is p-chloro;
$R^5$ is p-fluoro; and
n is 1.

10. A method in accordance with claim 1 in which:
$R^1$ is H;
$R^2$ is H;
$R^4$ is $C=O$;
$R^8$ is N;
X is H;
$R^5$ is H; and
n is 1.

11. A method for detecting the presence of retroviral proteases in a biological sample, said method comprising:

(a) combining said sample with a compound having the formula

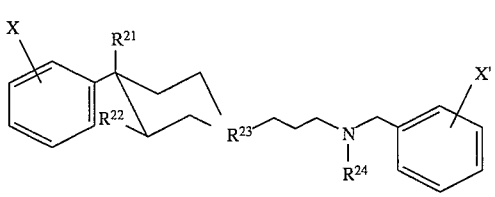

in which:
  $R^{21}$ is a member selected from the group consisting of H, OH, $CH_2OH$ and $OC(O)CH_3$;
  $R^{22}$ is a member selected from the group consisting of H and OH;
  $R^{23}$ is a member selected from the group consisting of N, $N^+-O^-$, $N^+(Hal^-)-CH_3$, $N^+(Hal^-)-CH_2CH_2Ph$ and $C-OH$;
  $R^{24}$ is a member selected from the group consisting of H, $C_1-C_3$ alkyl, $C_2-C_4$ alkoxyalkyl, phenyl-($C_1-C_3$ alkyl), and phenyl-($C_1-C_3$ alkyl)-carbonyl;
  X is a member selected from the group consisting of H and halogen; and
  X' is a member selected from the group consisting of H and phenyl;

where Hal is halogen and Ph is phenyl;

or a radiolabeled analog of said compound; and (b) detecting the presence of complexes formed by the binding of said compound to said retroviral proteases as a measure of the presence of said retroviral proteases in said biological sample.

12. A method in accordance with claim 11 in which:

$R^{21}$ is OH;

$R^{22}$ is H;

$R^{23}$ is N; and

X is p-chloro.

13. A method in accordance with claim 12 in which $R^{24}$ is a member selected from the group consisting of $C_2$–$C_4$ alkoxyalkyl, phenyl-($C_1$–$C_3$ alkyl), and phenyl-($C_1$–$C_3$ alkyl)-carbonyl.

14. A method in accordance with claim 12 in which $R^{24}$ is a member selected from the group consisting of phenyl-($C_1$–$C_3$ alkyl), and phenyl-($C_1$–$C_3$ alkyl)-carbonyl.

15. A method for detecting the presence of retroviral proteases in a biological sample, said method comprising:

(a) combining said sample with a compound having the formula in which:

$R^{41}$ is a member selected from the group consisting of H and OH;

$R^{42}$ is a member selected from the group consisting of C=O and in which Y and Z are members independently selected from the group consisting of O and S; and X and X' are members independently selected from the group consisting of H and halogen;

or a radiolabeled analog of said compound; and (b) detecting the presence of complexes formed by the binding of said compound to said retroviral proteases as a measure of the presence of said retroviral proteases in said biological sample.

16. A method in accordance with claim 15 in which:

$R^{41}$ is OH;

X is p-chloro; and

X' is p-fluoro.

17. A method in accordance with claim 16 in which Y and Z are each S.

18. A method for detecting the presence of retroviral proteases in a biological sample, said method comprising:

(a) combining said sample with a compound having the formula in which:

$R^{51}$ is a member selected from the group consisting of H and OH;

$R^{52}$ is a member selected from the group consisting of C=O and C(OH)—Ph, in which Ph is phenyl; and X is a member selected from the group consisting of H and halogen;

or a radiolabeled analog of said compound; and (b) detecting the presence of complexes formed by the binding of said compound to said retroviral proteases as a measure of the presence of said retroviral proteases in said biological sample.

19. A method in accordance with claim 18 in which:

$R^{51}$ is OH; and

X is H.

20. A method in accordance with claim 19 in which $R^{52}$ is C(OH)—Ph.

21. A method for detecting the presence of retroviral proteases in a biological sample, said method comprising:

(a) combining said sample with a compound having the formula in which:

$R^{61}$ is a member selected from the group consisting of H and OH;

$R^{62}$ is a member selected from the group consisting of H, $C_1$–$C_6$ alkyl, $C_3$–$C_6$ alkenyl, $C_3$–$C_6$ alkynyl, hydroxy-($C_1$–$C_6$ alkyl), hydroxy-($C_3$–$C_6$ alkenyl), and hydroxy-($C_3$–$C_6$ alkynyl); and X is a member selected from the group consisting of H and halogen;

or a radiolabeled analog of said compound; and (b) detecting the presence of complexes formed by the binding of said compound to said retroviral proteases as a measure of the presence of said retroviral proteases in said biological sample.

22. A method in accordance with claim 21 in which:

$R^{61}$ is OH; and

X is p-chloro.

23. A method in accordance with claim 22 in which $R^{62}$ is a member selected from the group consisting of H, $CH_2CH_2CH_2CH=CH_2$, and $CH_2C\equiv CCH_2OH$.

24. A method for detecting the presence of retroviral proteases in a biological sample, said method comprising:

(a) combining said sample with a compound having the formula or a radiolabeled analog of said compound; and (b) detecting the presence of complexes formed by the binding of said compound to said retroviral proteases as a measure of the presence of said retroviral proteases in said biological sample.

25. A method for detecting the presence of retroviral proteases in a biological sample, said method comprising:

(a) combining said sample with a compound having the formula

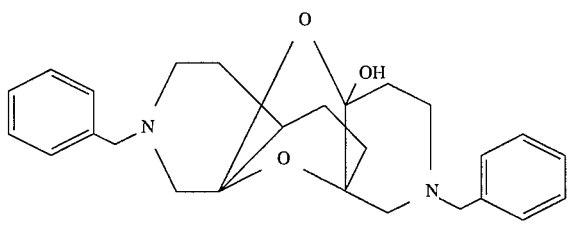

or a radiolabeled analog of said compound; and (b) detecting the presence of complexes formed by the binding of said compound to said retroviral proteases as a measure of the presence of said retroviral proteases in said biological sample.

26. A method for inhibiting protein processing by retroviral proteases in living cells, said method comprising exposing said cells to an effective amount of a compound having the formula

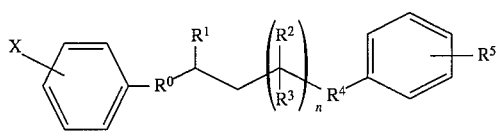

in which:

$R^0$ is

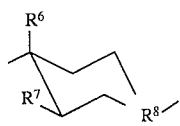

in which:

$R^6$ is OH;

$R^7$ is H; and $R^8$ is a member selected from the group consisting of N, and C—OH;

$R^1$ is a member selected from the group consisting of H and Ph;

$R^2$ is a member selected from the group consisting of H and $CH_3$;

$R^3$ is H;

$R^4$ is a member selected from the group consisting of $CH_2$, $C=CH_2$, CHOH, $C=O$, $C=N$—OH, $C=N$—$NH_2$, $C=N$—NH—$C_2H_5OH$, C(OH)—Ph, C(OH)—$CH_2SCH_3$, C(OH)—$CH=CH_2$,

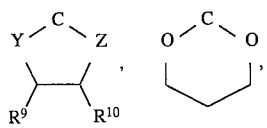

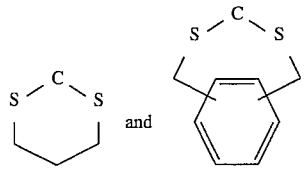

in which:

Y and Z are members independently selected from the group consisting of O and S; and $R^9$ and $R^{10}$ are members independently selected from the group consisting of H and $C_1$–$C_3$ alkyl;

$R^5$ is a member selected from the group consisting of H, halogen and phenyl;

X is a member selected from the group consisting of H and halogen; and n is zero or 1; where Hal is halogen and Ph is phenyl.

27. A method in accordance with claim 26 in which:

$R^1$ is H;

$R^2$ is H; and n is 1.

28. A method in accordance with claim 26 in which:

$R^1$ is H;

$R^2$ is H;

$R^3$ is H;

$R^4$ is a member selected from the group consisting of C(OH)—Ph,

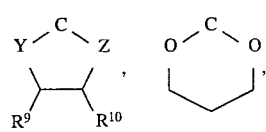

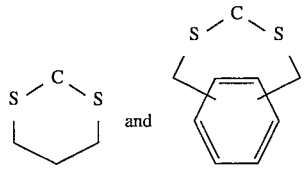

$R^8$ is N; and n is 1.

29. A method in accordance with claim 28 in which Z and Y are either both O or both S.

30. A method in accordance with claim 28 in which Z and Y are both S.

31. A method in accordance with claim 28 in which:

$R^4$ is

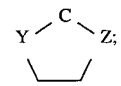

Z and Y are both S;

$R^5$ is p-fluoro;

X is p-chloro; and n is 1.

32. A method in accordance with claim 26 in which X is p-chloro.

33. A method in accordance with claim 26 in which $R^5$ is p-fluoro.

34. A method in accordance with claim 26 in which:

$R^1$ is H;
$R^2$ is H;
$R^4$ is C=O;
$R^8$ is N;
X is p-chloro;
$R^5$ is p-fluoro; and
n is 1.

35. A method in accordance with claim 26 in which:
$R^1$ is H;
$R^2$ is H;
$R^4$ is C=O;
$R^8$ is N;
X is H;
$R^5$ is H; and
n is 1.

36. A method for inhibiting protein processing by retroviral proteases in living cells, said method comprising exposing said cells to an effective amount of a compound having the formula

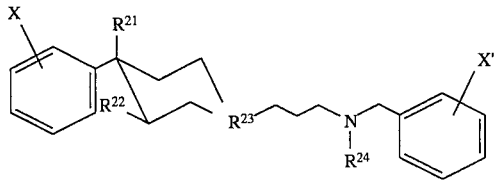

in which:

$R^{21}$ is a member selected from the group consisting of H, OH, $CH_2OH$ and $OC(O)CH_3$;

$R^{22}$ is a member selected from the group consisting of H and OH;

$R^{23}$ is a member selected from the group consisting of N, $N^+$—$O^-$, $N^+(Hal^-)$—$CH_3$, $N^+(Hal^-)$—$CH_2CH_2Ph$ and C—OH;

$R^{24}$ is a member selected from the group consisting of H, $C_1$–$C_3$ alkyl, $C_2$–$C_4$ alkoxyalkyl, phenyl-($C_1$–$C_3$ alkyl), and phenyl-($C_1$–$C_3$ alkyl)-carbonyl;

X is a member selected from the group consisting of H and halogen; and

X' is a member selected from the group consisting of H and phenyl;

where Hal is halogen and Ph is phenyl.

37. A method in accordance with claim 36 in which:
$R^{21}$ is OH;
$R^{22}$ is H;
$R^{23}$ is N; and
X is p-chloro.

38. A method in accordance with claim 37 in which $R^{24}$ is a member selected from the group consisting of $C_2$–$C_4$ alkoxyalkyl, phenyl-($C_1$–$C_3$ alkyl), and phenyl-($C_1$–$C_3$ alkyl)-carbonyl.

39. A method in accordance with claim 37 in which $R^{24}$ is a member selected from the group consisting of phenyl-($C_1$–$C_3$ alkyl), and phenyl-($C_1$–$C_3$ alkyl)-carbonyl.

40. A method for inhibiting protein processing by retroviral proteases in living cells, said method comprising exposing said cells to an effective amount of a compound having the formula

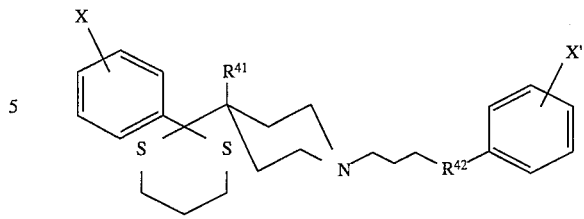

in which:

$R^{41}$ is a member selected from the group consisting of H and OH;

$R^{42}$ is a member selected from the group consisting of C=O and

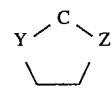

in which Y and Z are members independently selected from the group consisting of O and S; and X and X' are members independently selected from the group consisting of H and halogen.

41. A method in accordance with claim 40 in which:
$R^{41}$ is OH;
X is p-chloro; and
X' is p-fluoro.

42. A method in accordance with claim 40 in which Y and Z are each S.

43. A method for inhibiting protein processing by retroviral proteases in living cells, said method comprising exposing said cells to an effective amount of a compound having the formula

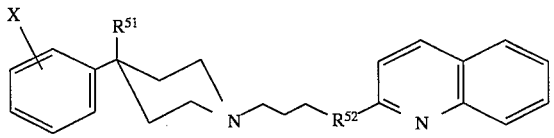

in which:

$R^{51}$ is a member selected from the group consisting of H and OH;

$R^{52}$ is a member selected from the group consisting of C=O and C(OH)—Ph, in which Ph is phenyl; and X is a member selected from the group consisting of H and halogen.

44. A method in accordance with claim 43 in which:
$R^{51}$ is OH; and
X is H.

45. A method in accordance with claim 44 in which $R^{52}$ is C(OH)—Ph.

46. A method for inhibiting protein processing by retroviral proteases in living cells, said method comprising exposing said cells to an effective amount of a compound having the formula

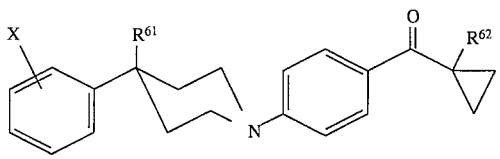

in which:
- $R^{61}$ is a member selected from the group consisting of H and OH;
- $R^{62}$ is a member selected from the group consisting of H, $C_1$–$C_6$ alkyl, $C_3$–$C_6$ alkenyl, $C_3$–$C_6$ alkynyl, hydroxy-($C_1$–$C_6$ alkyl), hydroxy-($C_3$–$C_6$ alkenyl), and hydroxy-($C_3$–$C_6$ alkynyl); and
- X is a member selected from the group consisting of H and halogen.

47. A method in accordance with claim 46 in which:
- $R^{61}$ is OH; and
- X is p-chloro.

48. A method in accordance with claim 47 in which $R^{62}$ is a member selected from the group consisting of H, $CH_2CH_2CH_2CH{=}CH_2$, and $CH_2C{\equiv}CCH_2OH$.

49. A method for inhibiting protein processing by retroviral proteases in living cells, said method comprising exposing said cells to an effective amount of a compound having the formula

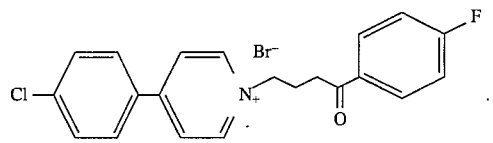

50. A method for inhibiting protein processing by retroviral proteases in living cells, said method comprising exposing said cells to an effective amount of a compound having the formula

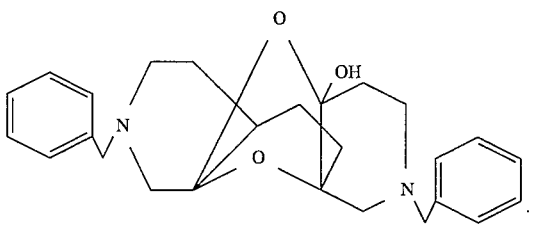

51. A method for detecting the presence of retroviral proteases in a biological sample, said method comprising:
(a) combining said sample with a compound having the formula

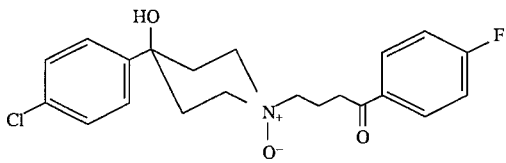

or a radiolabeled analog of said compound; and
(b) detecting the presence of complexes formed by the binding of said compound to said retroviral proteases as a measure of the presence of said retroviral proteases in said biological sample.

52. A method for detecting the presence of retroviral proteases in a biological sample, said method comprising:

(a) combining said sample with a compound having the formula

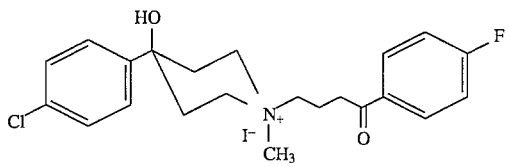

or a radiolabeled analog of said compound; and
(b) detecting the presence of complexes formed by the binding of said compound to said retroviral proteases as a measure of the presence of said retroviral proteases in said biological sample.

53. A method for detecting the presence of retroviral proteases in a biological sample, said method comprising:
(a) combining said sample with a compound having the formula

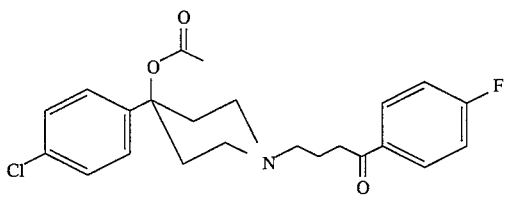

or a radiolabeled analog of said compound; and
(b) detecting the presence of complexes formed by the binding of said compound to said retroviral proteases as a measure of the presence of said retroviral proteases in said biological sample.

54. A method for detecting the presence of retroviral proteases in a biological sample, said method comprising:
(a) combining said sample with a compound having the formula

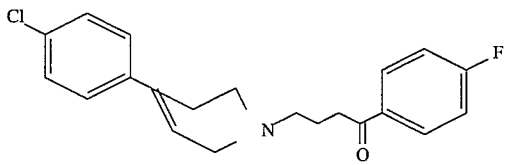

or a radiolabeled analog of said compound; and
(b) detecting the presence of complexes formed by the binding of said compound to said retroviral proteases as a measure of the presence of said retroviral proteases in said biological sample.

55. A method for detecting the presence of retroviral proteases in a biological sample, said method comprising:
(a) combining said sample with a compound having the formula

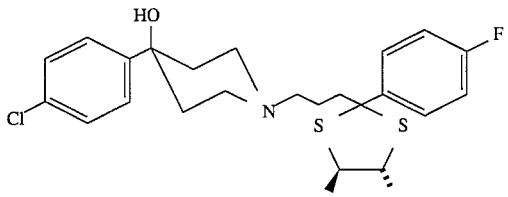

or a radiolabeled analog of said compound; and
(b) detecting the presence of complexes formed by the binding of said compound to said retroviral proteases as a measure of the presence of said retroviral proteases in said biological sample.

56. A method for detecting the presence of retroviral proteases in a biological sample, said method comprising:

(a) combining said sample with a compound having the formula

[Structure: 4-chlorophenyl-4-hydroxypiperidine with N+ bearing benzyl group and 3-(4-fluorophenyl)-3-oxopropyl group, Br- counterion]

or a radiolabeled analog of said compound; and (b) detecting the presence of complexes formed by the binding of said compound to said retroviral proteases as a measure of the presence of said retroviral proteases in said biological sample.

57. A method for detecting the presence of retroviral proteases in a biological sample, said method comprising:

(a) combining said sample with a compound having the formula

[Structure: 4-phenylpiperidine (with H) N-substituted with 3-(4-fluorophenyl)-3-oxopropyl]

or a radiolabeled analog of said compound; and (b) detecting the presence of complexes formed by the binding of said compound to said retroviral proteases as a measure of the presence of said retroviral proteases in said biological sample.

58. A method for detecting the presence of retroviral proteases in a biological sample, said method comprising:

(a) combining said sample with a compound having the formula

[Structure: 4-(4-chlorophenyl)-4-hydroxypiperidine N-substituted with ethyl-dithiolane bearing 4-fluorophenyl]

or a radiolabeled analog of said compound; and (b) detecting the presence of complexes formed by the binding of said compound to said retroviral proteases as a measure of the presence of said retroviral proteases in said biological sample.

59. A method for detecting the presence of retroviral proteases in a biological sample, said method comprising:

(a) combining said sample with a compound having the formula

[Structure: 4-phenyl-4-hydroxypiperidine N-substituted with 3-(4-pyridyl)-3-oxopropyl]

or a radiolabeled analog of said compound; and (b) detecting the presence of complexes formed by the binding of said compound to said retroviral proteases as a measure of the presence of said retroviral proteases in said biological sample.

60. A method for detecting the presence of retroviral proteases in a biological sample, said method comprising:

(a) combining said sample with a compound having the formula

[Structure: 4-(4-chlorophenyl)-4-hydroxypiperidine N-oxide with propyl-(4-fluorophenyl)-CH2 group]

or a radiolabeled analog of said compound; and (b) detecting the presence of complexes formed by the binding of said compound to said retroviral proteases as a measure of the presence of said retroviral proteases in said biological sample.

61. A method for detecting the presence of retroviral proteases in a biological sample, said method comprising:

(a) combining said sample with a compound having the formula

[Structure: 4-(4-chlorophenyl)-4-hydroxypiperidine N-substituted with 2-phenyl-3-(4-methylphenyl)-3-oxopropyl]

or a radiolabeled analog of said compound; and (b) detecting the presence of complexes formed by the binding of said compound to said retroviral proteases as a measure of the presence of said retroviral proteases in said biological sample.

62. A method for detecting the presence of retroviral proteases in a biological sample, said method comprising:

(a) combining said sample with a compound having the formula

[Structure: 4-(4-chlorophenyl)-4-hydroxypiperidine N-substituted with 2-phenyl-3-(4-methylphenyl)-3-oxopropyl variant]

or a radiolabeled analog of said compound; and (b) detecting the presence of complexes formed by the binding of said compound to said retroviral proteases as a measure of the presence of said retroviral proteases in said biological sample.

63. A method for detecting the presence of retroviral proteases in a biological sample, said method comprising:
(a) combining said sample with a compound having the formula

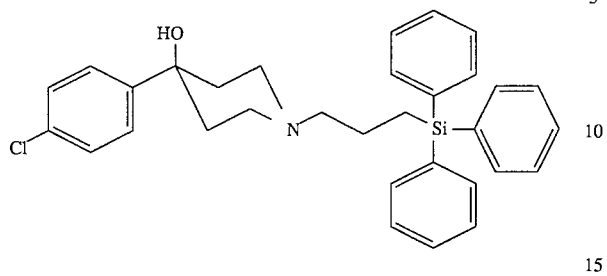

or a radiolabeled analog of said compound; and
(b) detecting the presence of complexes formed by the binding of said compound to said retroviral proteases as a measure of the presence of said retrovital proteases in said biological sample.

64. A method for detecting the presence of retroviral proteases in a biological sample, said method comprising:
(a) combining said sample with a compound having the formula

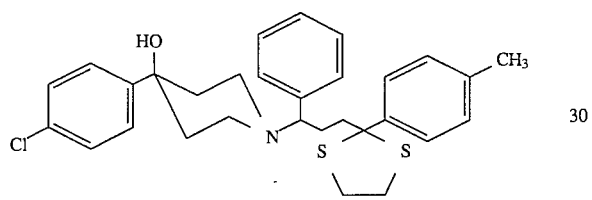

or a radiolabeled analog of said compound; and
(b) detecting the presence of complexes formed by the binding of said compound to said retroviral proteases as a measure of the presence of said retroviral proteases in said biological sample.

65. A method for detecting the presence of retrovital proteases in a biological sample, said method comprising:
(a) combining said sample with a compound having the formula

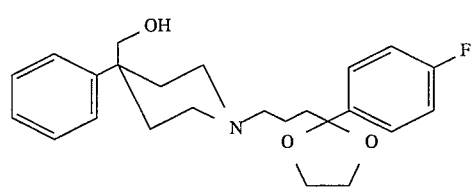

or a radiolabeled analog of said compound; and
(b) detecting the presence of complexes formed by the binding of said compound to said retroviral proteases as a measure of the presence of said retroviral proteases in said biological sample.

66. A method for detecting the presence of retroviral proteases in a biological sample, said method comprising:
(a) combining said sample with a compound having the formula

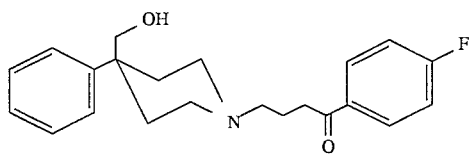

or a radiolabeled analog of said compound; and
(b) detecting the presence of complexes formed by the binding of said compound to said retroviral proteases as a measure of the presence of said retroviral proteases in said biological sample.

67. A method for detecting the presence of retroviral proteases in a biological sample, said method comprising:
(a) combining said sample with a compound having the formula

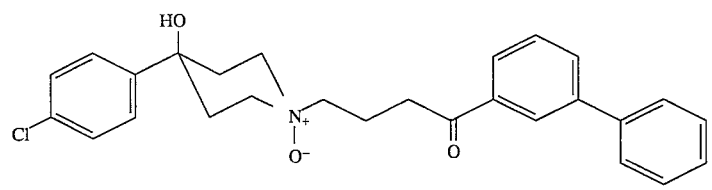

or a radiolabeled analog of said compound; and
(b) detecting the presence of complexes formed by the binding of said compound to said retrovital proteases as a measure of the presence of said retroviral proteases in said biological sample.

68. A method for detecting the presence of retroviral proteases in a biological sample, said method comprising:
(a) combining said sample with a compound having the formula

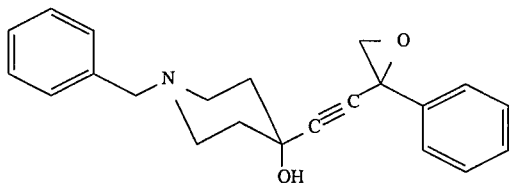

or a radiolabeled analog of said compound; and (b) detecting the presence of complexes formed by the binding of said compound to said retrovital proteases as a measure of the presence of said retroviral proteases in said biological sample.

69. A method for detecting the presence of retroviral proteases in a biological sample, said method comprising:

(a) combining said sample with a compound having the formula

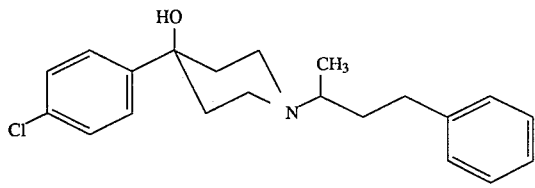

or a radiolabeled analog of said compound; and (b) detecting the presence of complexes formed by the binding of said compound to said retroviral proteases as a measure of the presence of said retroviral proteases in said biological sample.

70. A method for detecting the presence of retroviral proteases in a biological sample, said method comprising:

(a) combining said sample with a compound having the formula

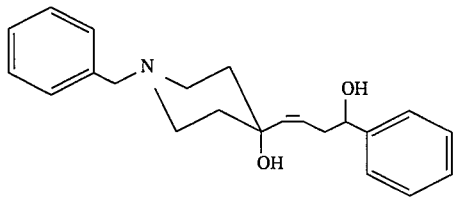

or a radiolabeled analog of said compound; and (b) detecting the presence of complexes formed by the binding of said compound to said retroviral proteases as a measure of the presence of said retroviral proteases in said biological sample.

71. A method for detecting the presence of retroviral proteases in a biological sample, said method comprising:

(a) combining said sample with a compound having the formula

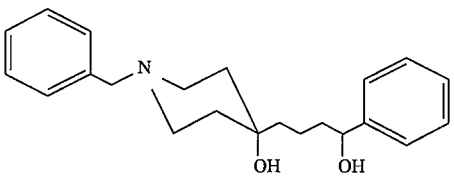

or a radiolabeled analog of said compound; and (b) detecting the presence of complexes formed by the binding of said compound to said retroviral proteases as a measure of the presence of said retroviral proteases in said biological sample.

72. A method for detecting the presence of retroviral proteases in a biological sample, said method comprising:

(a) combining said sample with a compound having the formula

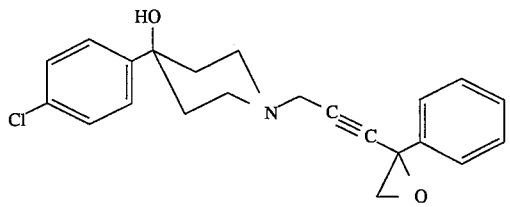

or a radiolabeled analog of said compound; and (b) detecting the presence of complexes formed by the binding of said compound to said retroviral proteases as a measure of the presence of said retroviral proteases in said biological sample.

73. A method for detecting the presence of retroviral proteases in a biological sample, said method comprising:

(a) combining said sample with a compound having the formula

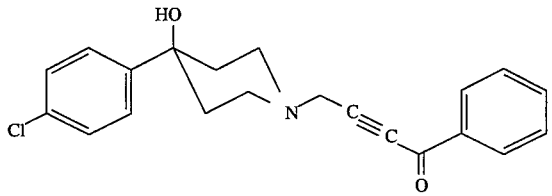

or a radiolabeled analog of said compound; and (b) detecting the presence of complexes formed by the binding of said compound to said retroviral proteases as a measure of the presence of said retroviral proteases in said biological sample.

74. A method for detecting the presence of retroviral proteases in a biological sample, said method comprising:

(a) combining said sample with a compound having the formula

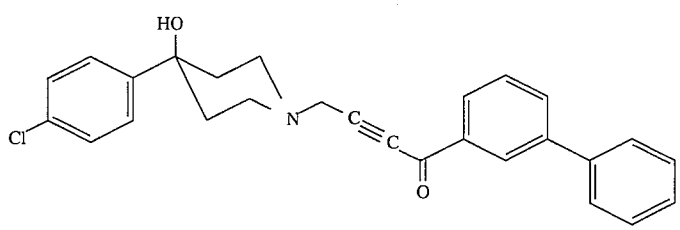

or a radiolabeled analog of said compound; and (b) detecting the presence of complexes formed by the binding of said compound to said retroviral proteases as a measure of the presence of said retroviral proteases in said biological sample.

75. A method for detecting the presence of retroviral proteases in a biological sample, said method comprising:

(a) combining said sample with a compound having the formula

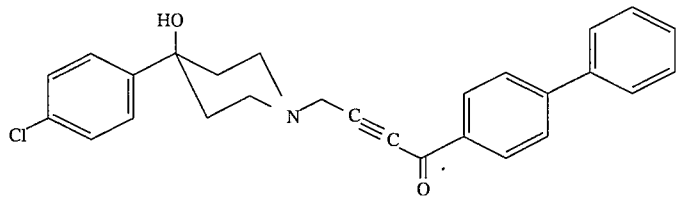

or a radiolabeled analog of said compound; and (b) detecting the presence of complexes formed by the binding of said compound to said retroviral proteases as a measure of the presence of said retroviral proteases in said biological sample.

76. A method for detecting the presence of retroviral proteases in a biological sample, said method comprising:

(a) combining said sample with a compound having the formula

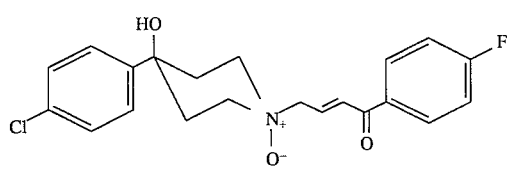

or a radiolabeled analog of said compound; and (b) detecting the presence of complexes formed by the binding of said compound to said retroviral proteases as a measure of the presence of said retroviral proteases in said biological sample.

77. A method for detecting the presence of retroviral proteases in a biological sample, said method comprising:

(a) combining said sample with a compound having the formula

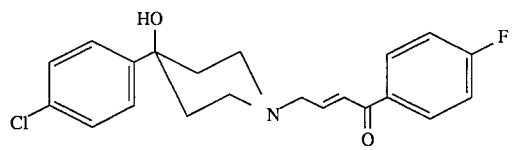

or a radiolabeled analog of said compound; and (b) detecting the presence of complexes formed by the binding of said compound to said retroviral proteases as a measure of the presence of said retroviral proteases in said biological sample.

78. A method for detecting the presence of retroviral proteases in a biological sample, said method comprising:

(a) combining said sample with a compound having the formula

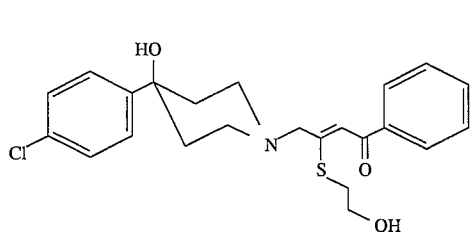

or a radiolabeled analog of said compound; and (b) detecting the presence of complexes formed by the binding of said compound to said retroviral proteases as a measure of the presence of said retroviral proteases in said biological sample.

79. A method for inhibiting protein processing by retroviral proteases in living cells, said method comprising exposing said cells to an effective amount of a compound having the formula

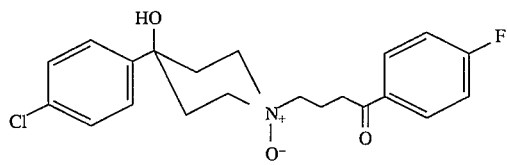

80. A method for inhibiting protein processing by retroviral proteases in living cells, said method comprising exposing said cells to an effective amount of a compound having the formula

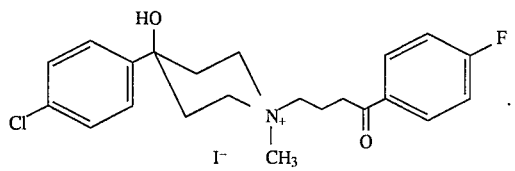

81. A method for inhibiting protein processing by retroviral proteases in living cells, said method comprising exposing said cells to an effective amount of a compound having the formula

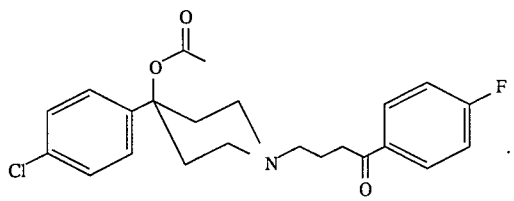

82. A method for inhibiting protein processing by retroviral proteases in living cells, said method comprising exposing said cells to an effective amount of a compound having the formula

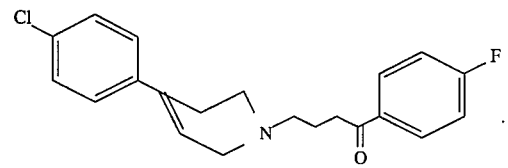

83. A method for inhibiting protein processing by retroviral proteases in living cells, said method comprising exposing said cells to an effective amount of a compound having the formula

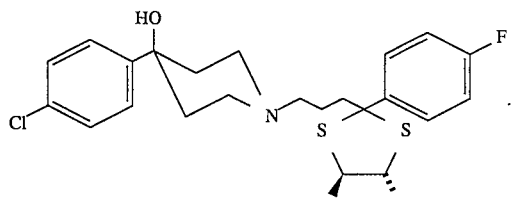

84. A method for inhibiting protein processing by retroviral proteases in living cells, said method comprising exposing said cells to an effective amount of a compound having the formula

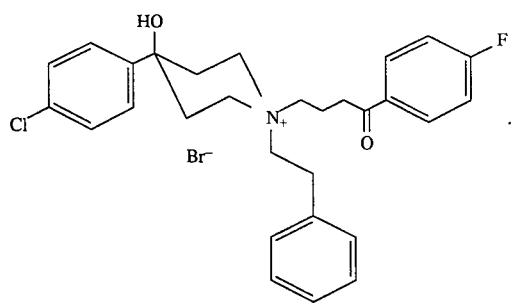

85. A method for inhibiting protein processing by retroviral proteases in living cells, said method comprising exposing said cells to an effective amount of a compound having the formula

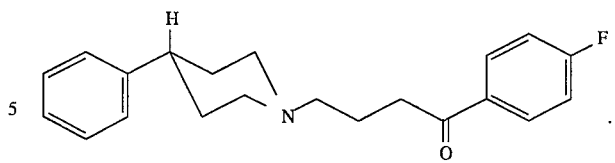

86. A method for inhibiting protein processing by retroviral proteases in living cells, said method comprising exposing said cells to an effective amount of a compound having the formula

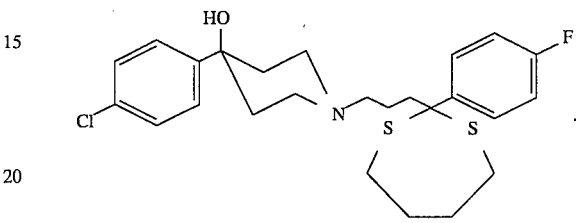

87. A method for inhibiting protein processing by retroviral proteases in living cells, said method comprising exposing said cells to an effective amount of a compound having the formula

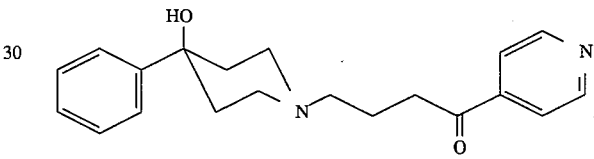

88. A method for inhibiting protein processing by retroviral proteases in living cells, said method comprising exposing said cells to an effective amount of a compound having the formula

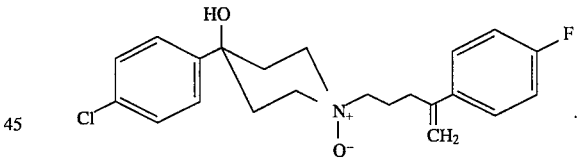

89. A method for inhibiting protein processing by retroviral proteases in living cells, said method comprising exposing said cells to an effective amount of a compound having the formula

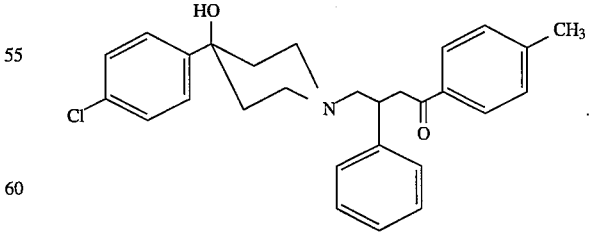

90. A method for inhibiting protein processing by retroviral proteases in living cells, said method comprising exposing said cells to an effective amount of a compound having the formula

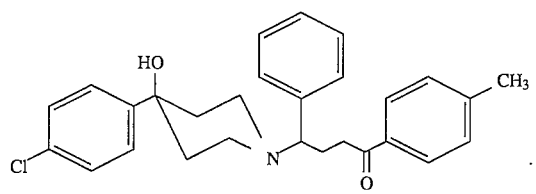

91. A method for inhibiting protein processing by retroviral proteases in living cells, said method comprising exposing said cells to an effective amount of a compound having the formula

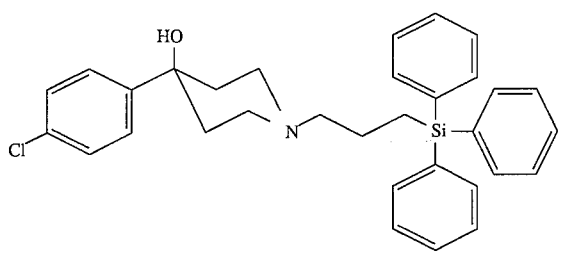

92. A method for inhibiting protein processing by retroviral proteases in living cells, said method comprising exposing said cells to an effective amount of a compound having the formula

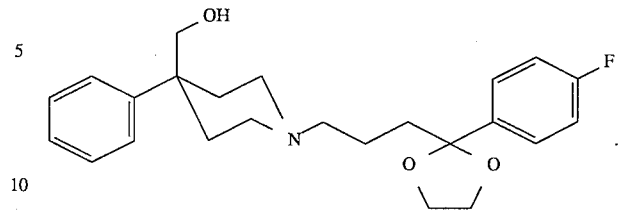

94. A method for inhibiting protein processing by retroviral proteases in living cells, said method comprising exposing said cells to an effective amount of a compound having the formula

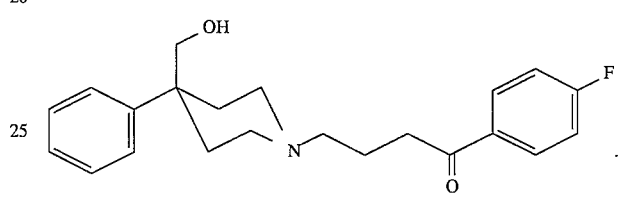

95. A method for inhibiting protein processing by retroviral proteases in living cells, said method comprising exposing said cells to an effective amount of a compound having the formula

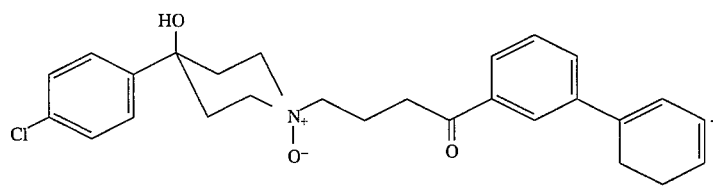

96. A method for inhibiting protein processing by retroviral proteases in living cells, said method comprising exposing said cells to an effective amount of a compound having the formula

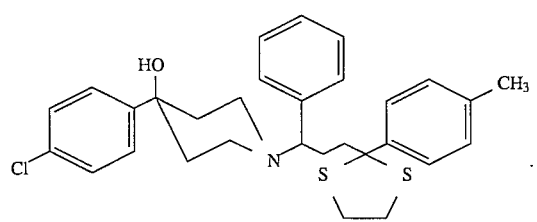

93. A method for inhibiting protein processing by retroviral proteases in living cells, said method comprising exposing said cells to an effective amount of a compound having the formula

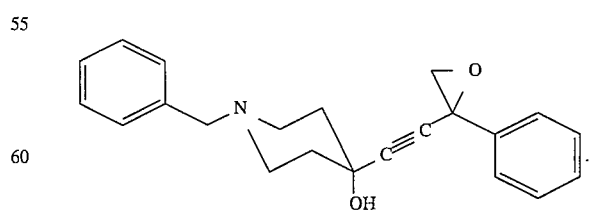

97. A method for inhibiting protein processing by retroviral proteases in living cells, said method comprising exposing said cells to an effective amount of a compound having the formula

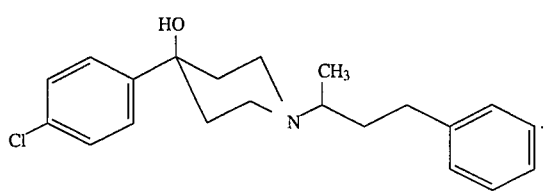

98. A method for inhibiting protein processing by retroviral proteases in living cells, said method comprising exposing said cells to an effective amount of a compound having the formula

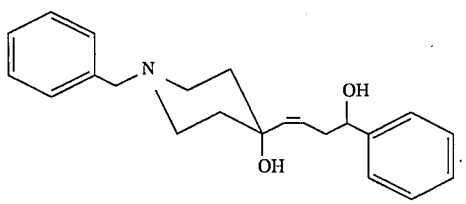

99. A method for inhibiting protein processing by retroviral proteases in living cells, said method comprising exposing said cells to an effective amount of a compound having the formula

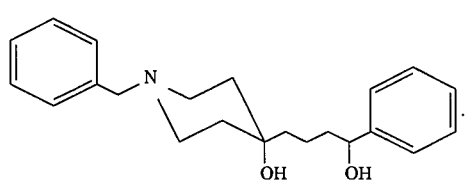

100. A method for inhibiting protein processing by retroviral proteases in living cells, said method comprising exposing said cells to an effective amount of a compound having the formula

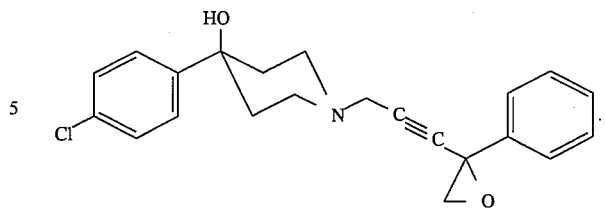

101. A method for inhibiting protein processing by retroviral proteases in living cells, said method comprising exposing said cells to an effective amount of a compound having the formula

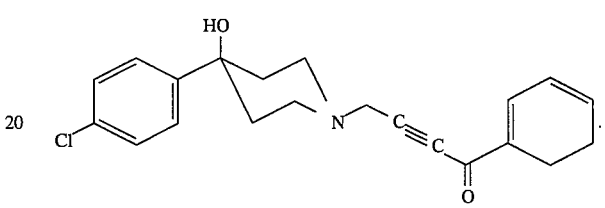

102. A method for inhibiting protein processing by retroviral proteases in living cells, said method comprising exposing said cells to an effective amount of a compound having the formula

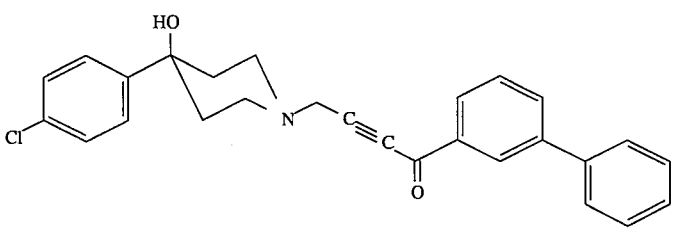

103. A method for inhibiting protein processing by retroviral proteases in living cells, said method comprising exposing said cells to an effective amount of a compound having the formula

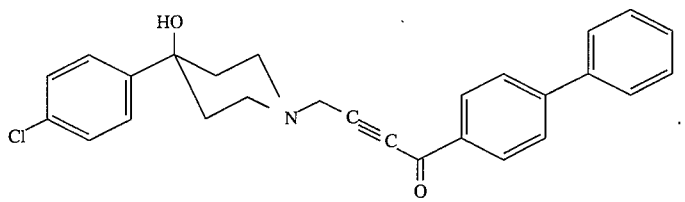

104. A method for inhibiting protein processing by retroviral proteases in living cells, said method comprising exposing said cells to an effective amount of a compound having the formula

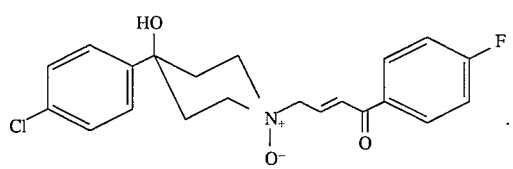

105. A method for inhibiting protein processing by retroviral proteases in living cells, said method comprising exposing said cells to an effective amount of a compound having the formula

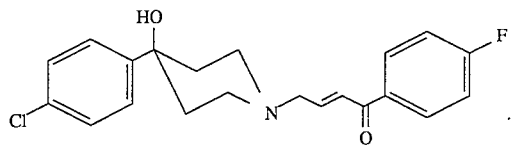

106. A method for inhibiting protein processing by retroviral proteases in living cells, said method comprising exposing said cells to an effective amount of a compound having the formula

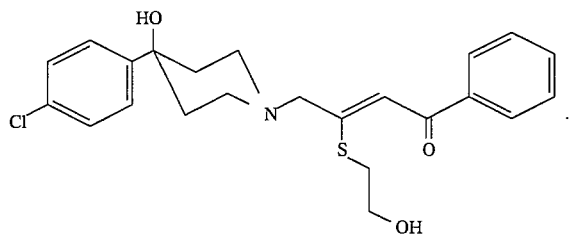

\* \* \* \* \*

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear (i i) MOLECULE TYPE: peptide (i i i) HYPOTHETICAL: NO (x i) SEQUENCE DESCRIPTION: SEQ ID NO:1:

```
Ala  Thr  Leu  Asn  Phe  Pro  Ile  Ser  Pro  Trp
1                   5                        10
```

(2) INFORMATION FOR SEQ ID NO:2:

(i) SEQUENCE CHARACTERISTICS:
    (A) LENGTH: 5 amino acids
    (B) TYPE: amino acid
    (C) STRANDEDNESS:
    (D) TOPOLOGY: linear (i i) MOLECULE TYPE: peptide (i i i) HYPOTHETICAL: NO (x i) SEQUENCE DESCRIPTION: SEQ ID NO:2:

```
Met  Ala  Phe  Arg  Glu
1                   5
```

(2) INFORMATION FOR SEQ ID NO:3:

(i) SEQUENCE CHARACTERISTICS:
    (A) LENGTH: 9 amino acids
    (B) TYPE: amino acid
    (C) STRANDEDNESS:
    (D) TOPOLOGY: linear (i i) MOLECULE TYPE: peptide (i i i) HYPOTHETICAL: NO (i x) FEATURE:
    (A) NAME/KEY: Modified-site
    (B) LOCATION: 6
    (D) OTHER INFORMATION: /product="OTHER"
        / note="Xaa =-[CH(OH)CH-2]- in a pseudo peptidyl bond,
        expressed as -psi[CH(OH)CH-2]-"

(x i) SEQUENCE DESCRIPTION: SEQ ID NO:3:

```
Val  Ser  Gln  Asn  Leu  Xaa  Val  Ile  Val
1                   5
```

(2) INFORMATION FOR SEQ ID NO:4:

(i) SEQUENCE CHARACTERISTICS:
    (A) LENGTH: 4 amino acids
    (B) TYPE: amino acid
    (C) STRANDEDNESS:
    (D) TOPOLOGY: linear (i i) MOLECULE TYPE: peptide (i i i) HYPOTHETICAL: NO (x i) SEQUENCE DESCRIPTION: SEQ ID NO:4:

```
Leu  Val  Tyr  Ser
1
```

(2) INFORMATION FOR SEQ ID NO:5:

(i) SEQUENCE CHARACTERISTICS:
    (A) LENGTH: 10 amino acids
    (B) TYPE: amino acid
    (C) STRANDEDNESS:
    (D) TOPOLOGY: linear (i i) MOLECULE TYPE: peptide ( i i i ) HYPOTHETICAL: NO ( x i ) SEQUENCE DESCRIPTION: SEQ ID NO:5:

Asp Arg Val Tyr Ile His Pro Phe His Leu
1               5                   10

( 2 ) INFORMATION FOR SEQ ID NO:6:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( x i ) SEQUENCE DESCRIPTION: SEQ ID NO:6:

Ser Gln Asn Tyr Pro Ile Val Gln
1               5

( 2 ) INFORMATION FOR SEQ ID NO:7:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( i x ) FEATURE:
        ( A ) NAME/KEY: Modified-site
        ( B ) LOCATION: 1
        ( D ) OTHER INFORMATION: /product="OTHER"
        / note="Xaa =ABZ-Thr, N-(4-aminobenzoyl)-L-threonine"

( i x ) FEATURE:
        ( A ) NAME/KEY: Modified-site
        ( B ) LOCATION: 3
        ( D ) OTHER INFORMATION: /product="Nle"

( i x ) FEATURE:
        ( A ) NAME/KEY: Modified-site
        ( B ) LOCATION: 4
        ( D ) OTHER INFORMATION: /product="OTHER"
        / note="Xaa =Phe(p-NO-2), para-nitro-phenylalanine"

( x i ) SEQUENCE DESCRIPTION: SEQ ID NO:7:

Xaa Ile Xaa Xaa Gln Arg
1               5

( 2 ) INFORMATION FOR SEQ ID NO:8:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( i x ) FEATURE:
        ( A ) NAME/KEY: Modified-site
        ( B ) LOCATION: 5
        ( D ) OTHER INFORMATION: /product="OTHER"
        / note="Xaa =-[CH(OH)CH-2]- in a pseudo peptidyl bond,
        expressed as -psi[CH(OH)CH-2]-"

(xi) SEQUENCE DESCRIPTION: SEQ ID NO:8:

Val Ser Asn Leu Xaa Val Ile Val
1               5

(2) INFORMATION FOR SEQ ID NO:9:

(i) SEQUENCE CHARACTERISTICS:
   (A) LENGTH: 16 base pairs
   (B) TYPE: nucleic acid
   (C) STRANDEDNESS: single
   (D) TOPOLOGY: linear (ii) MOLECULE TYPE: DNA (iii) HYPOTHETICAL: NO (xi) SEQUENCE DESCRIPTION: SEQ ID NO:9:

CATGGCTTTC AGAGAA                                                                 16

(2) INFORMATION FOR SEQ ID NO:10:

(i) SEQUENCE CHARACTERISTICS:
   (A) LENGTH: 16 base pairs
   (B) TYPE: nucleic acid
   (C) STRANDEDNESS: single
   (D) TOPOLOGY: linear (ii) MOLECULE TYPE: DNA (iii) HYPOTHETICAL: NO (xi) SEQUENCE DESCRIPTION: SEQ ID NO:10:

CGAAAGTCTC TTCTAG                                                                 16

(2) INFORMATION FOR SEQ ID NO:11:

(i) SEQUENCE CHARACTERISTICS:
   (A) LENGTH: 10 base pairs
   (B) TYPE: nucleic acid
   (C) STRANDEDNESS: single
   (D) TOPOLOGY: linear (ii) MOLECULE TYPE: DNA (iii) HYPOTHETICAL: NO (xi) SEQUENCE DESCRIPTION: SEQ ID NO:11:

GGTATCAGCT                                                                        10